US008008488B2

(12) United States Patent
Geneste et al.

(10) Patent No.: US 8,008,488 B2
(45) Date of Patent: Aug. 30, 2011

(54) PYRIMIDIN-2-ONE COMPOUNDS AND THEIR USE AS DOPAMINE $D_3$ RECEPTOR LIGANDS

(75) Inventors: Hervé Geneste, Neuhofen (DE); Andreas Kling, Mannheim (DE); Wilfried Braje, Rinteln (DE); Andreas Haupt, Schwetzingen (DE); Liliane Unger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 882 days.

(21) Appl. No.: 10/548,931

(22) PCT Filed: Mar. 12, 2004

(86) PCT No.: PCT/EP2004/002609
§ 371 (c)(1),
(2), (4) Date: May 2, 2006

(87) PCT Pub. No.: WO2004/080981
PCT Pub. Date: Sep. 23, 2004

(65) Prior Publication Data
US 2006/0235004 A1    Oct. 19, 2006

(30) Foreign Application Priority Data

Mar. 13, 2003    (DE) .................................. 103 11 065

(51) Int. Cl.
| | | |
|---|---|---|
| *C07D 403/06* | (2006.01) | |
| *C07D 403/14* | (2006.01) | |
| *C07D 401/06* | (2006.01) | |
| *C07D 401/14* | (2006.01) | |
| *A61K 31/505* | (2006.01) | |
| *A61K 31/506* | (2006.01) | |
| *A61P 25/16* | (2006.01) | |
| *A61P 25/18* | (2006.01) | |
| *A61P 25/24* | (2006.01) | |
| *A61P 25/22* | (2006.01) | |
| *A61P 25/30* | (2006.01) | |

(52) U.S. Cl. ........ 544/315; 544/316; 544/180; 514/269; 514/241; 514/252.13; 514/211.01; 514/211.08; 540/484; 540/569

(58) Field of Classification Search .................. 544/315, 544/316, 180; 514/269, 241, 245, 252.13; 514/211.01, 211.08; 540/484, 569
See application file for complete search history.

(56) References Cited

U.S. PATENT DOCUMENTS 5,859,014 A * 1/1999 Bantle et al. ............. 514/252.11
6,342,604 B1 * 1/2002 Hellendahl et al. ............ 544/300

FOREIGN PATENT DOCUMENTS

| EP | 0 748 800 A2 | 12/1996 |
|---|---|---|
| WO | WO/96/02519 A1 | 2/1996 |
| WO | WO 03/002543 | 1/2003 |

OTHER PUBLICATIONS

Strange, PG., et al., Trends in Pharmacological Sciences, vol. 29, No. 6, 314-321, 2008.*
Joyce et al., Drug Discovery Today, vol. 10, No. 13, 917-925, 2005.*
J. C. Schwartz et al., "The Dopamine D3 Receptor as a Target for Antipsychotics" Novel Antipsychotic Drugs New York 1992, pp. 135-144.
J. N. Joyce et al., "Dopamine $D_3$ Receptor as a Therapeutic Target for Antipsychotic and Antiparkinsonian Drugs" Pharmacology & Therapeutics 2001, vol. 90, pp. 231-259.
P. Sokoloff et al. "Molecular Cloning and Characterization of a Novel Dopamine Receptor ($D_3$) as a Target Neuroleptics" Nature Sep. 1990, vol. 347, pp. 146-151.
C. Burkhardt M.D. et al. "Neuroleptic Medications Inhibit Complex I of the Electron Transport chain" American Neurological Association 1993, pp. 512-517.
I. Maurer "Inhibition of Complex I by Neuroleptics in Normal Human Brain Cortex Parallels the Extrapyramidal Toxicity of Neuroleptics" Molecular and Cellular Biochemistry, Netherlands 1997, vol. 174, pp. 255-259.
S. Balijepalli et al. "Protein Thiol Oxidation by Haloperidol Results in Inhibition of Mitochondrial Complex I in Brain Regions: Comparison with Atypical Antipsychotics" Neurochemistry International 2001, vol. 38, pp. 425-435.
J. L. Mokrosz et al. "A search for New Trazodone-Like Antidepressants: Synthesis and Preliminary Receptor Binding Studies" Institute of Pharmacology, Polish Academy of Sciences Poland Feb. 1995, pp. 623-625.
F. J. Lopez et al. "Synthesis, Pharmacology and Pharmacokinetics of 3-(4-Aryl-piperazin-lylalkyl)-uracils as Uroselective Antagonists" Bioorganic & Medicinal Chemistry Letters 2003, vol. 13, pp. 1873-1878.
"2,4 (1H, 3H)-Pyrimidinedione, 3, 5-dimethyl1-1-[(4-phenyl-l-piperazinyl)butyl]-" Ambinter Screening Library, Jan. 2004.

* cited by examiner

*Primary Examiner* — Venkataraman Balasubramanian
(74) *Attorney, Agent, or Firm* — Lisa V. Mueller; Polsinelli Shughart PC

(57) ABSTRACT

The invention relates to pyrimidin 2-one compounds of general formula (I), in addition to the derivatives and tautomers of (I) and the physiologically acceptable salts of said compounds. In said formula, A represents linear or branched $C_3$-$C_6$ alkene, which can have a double bond or triple bond and/or a group Z, which is not adjacent to the nitrogen atom of the pyrimidinone ring and is selected from O, S, C(O), $NR^3$, C(O)$NR^3$, $NR^3$C(O), OC(O) and C(O)O; B represents a group of the formula (II), in which X stands for $CH_2$ or N and Y stands for $CH_2$ or $CH_2CH_2$, or X—Y can also jointly represent C=CH, C=CH—$CH_2$ or CH—CH=CH; $R^1$ and $R^2$ are defined as cited in the description and the claims; and Ar represents an optionally substituted aromatic group. The invention also relates to a pharmaceutical agent, containing at least one compound (I) and the tautomers, derivatives and/or acid addition salts of said compound, optionally together with physiologically acceptable carriers and/or auxiliary agents. The invention also relates to the use of compounds of formula (I), and their tautomers, derivatives and pharmacologically acceptable acid addition salts for producing a pharmaceutical agent for treating diseases which respond to the influence of dopamine $D_3$ receptor ligands.

20 Claims, No Drawings

PYRIMIDIN-2-ONE COMPOUNDS AND THEIR USE AS DOPAMINE $D_3$ RECEPTOR LIGANDS

CROSS REFERENCE TO RELATED APPLICATIONS

This application is a Section 371 application of PCT Application No. WO 2004/080981, filed Mar. 12, 2004, which claims the priority of German Patent Application No. DE 10311065.8, filed Mar. 13, 2003.

The present invention relates to novel pyrimidin-2-one compounds. These compounds have valuable therapeutic properties and are suitable in particular for the treatment of disorders which respond to modulation of the dopamine $D_3$ receptor.

Neurons receive their information inter alia via G protein-coupled receptors. There are numerous substances which exert their effect via these receptors. One of these is dopamine. Confirmed findings about the presence of dopamine and its physiological function as neurotransmitter have been published. Disturbances in the dopaminergic transmitter system result in disorders of the central nervous system which include, for example, schizophrenia, depression or Parkinson's disease. These and other disorders are treated with medicaments which interact with the dopamine receptors.

Until 1990, two subtypes of dopamine receptors were clearly defined pharmacologically, namely the $D_1$ and $D_2$ receptors. More recently, a third subtype has been found, namely the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-259 "The Dopamine $D_3$-Receptor as a Therapeutic Target for Antipsychotic and Antiparkinsonian Drugs").

Dopamine receptors are now divided into two families. Firstly the $D_2$ group consisting of $D_2$, $D_3$ and $D_4$ receptors, and secondly the $D_1$ group consisting of $D_1$ and $D_5$ receptors. Whereas $D_1$ and $D_2$ receptors are widespread, the expression of $D_3$ receptors by contrast appears to be regioselective. Thus, these receptors are preferentially found in the limbic system, the projecting regions of the mesolimbic dopamine system, especially in the nucleus accumbens, but also in other regions such as amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Pyrimidine compounds having dopamine $D_3$ receptor affinity are disclosed in DE 10131543 and WO 96/02519. Some of these compounds have high affinities for the $D_3$ receptor. They are therefore proposed for the treatment of disorders of the central nervous system.

There have been various reports that neuroleptics may lead to inhibition of mitochondrial respiration. It has been shown that such an inhibition is the cause of the neurotoxic effect of neuroleptics and of the irreversible extrapyramidal side effects which are observed on prolonged administration of neuroleptics (see C. Burkhardt et al, Annals of Neurology, Vol 33 (1993) 512-517; I. Maurer et al, Molecular and Cellular Biochemistry 174 (1997) 225-229; S. Balijepalli et al, Neurochemistry International 38 (2001) 425-435). It is therefore desirable to have selective dopamine $D_3$ receptor ligands which moreover have only a slight or no inhibitory effect on mitochondrial respiration.

The compounds ought in addition to show little plasma protein binding. The advantage of little plasma protein binding is that the compounds show better tolerability because the plasma level is more uniform and uncontrolled release of the active ingredient from plasma protein binding, for example as the result of increased physical activity or because of interactions with other medicaments, is avoided.

The invention is therefore based on the object of providing compounds which act as selective dopamine $D_3$ receptor ligands. These compounds ought additionally to lead to inhibition of mitochondrial respiration only at high dosages or not at all. The compounds ought in addition to show little plasma protein binding.

This object is achieved by pyrimidin-2-one compounds of the general formula I

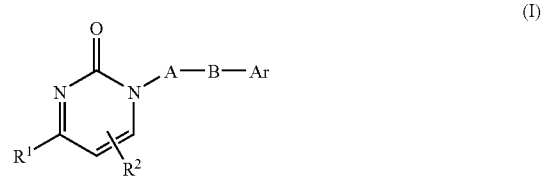

in which
A is linear or branched C3-C6-alkylene which may have a double bond or a triple bond and/or a group Z which is not adjacent to the nitrogen atom of the pyrimidinone ring and is selected from O, S, C(O), $NR^3$, $C(O)NR^3$, $NR^3C(O)$, OC(O) and C(O)O
B is a radical of the formula:

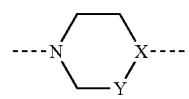

in which X is $CH_2$ or N, and Y is $CH_2$ or $CH_2CH_2$, or X—Y together may also be C=CH, C=CH—$CH_2$ or CH—CH=CH, —
$R^1$, $R^2$ are independently of one another hydrogen, CN, $NO_2$, halogen, $OR^{3a}$, $NR^4R^5$, $C(O)NR^4R^5$, O—$C(O)NR^4R^5$, $SR^6$, $SOR^6$, $SO_2R^6$, $SO_2NR^4R^5$, $COOR^7$, O—$C(O)R^8$, $COR^8$, $C_1$-$C_6$-alkyl, $C_1$-$C_6$-haloalkyl, $C_2$-$C_6$-alkenyl, $C_2$-$C_6$-alkynyl, $C_2$-$C_6$-haloalkenyl, $C_3$-$C_6$-cycloalkyl,
5- or 6-membered heterocyclyl having 1, 2 or 3 heteroatoms selected from O, S and N, which may be substituted by one or two radicals which are selected independently of one another from $C_1$-$C_4$-alkyl, $C_1$-$C_4$-alkoxy, $NR^4R^5$, CN, OH, $C_1$-$C_2$-fluoroalkyl or halogen,
phenyl which may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen,
$C_1$-$C_6$-alkyl which is substituted by a radical selected from $OR^{3b}$, $NR^4R^5$, $C(O)NR^4R^5$, O—$C(O)NR^4R^5$, $SR^5$, $SOR^6$, $SO_2R^6$, $SO_2NR^4R^5$, $COOR^7$, O—$C(O)R^8$, $COR^8$, $C_3$-$C_6$-cycloalkyl, 5- or 6-membered heterocyclyl having 1, 2 or 3 heteroatoms selected from O, S and N, and phenyl, where phenyl and heterocyclyl in turn may be substituted by one or two radicals which are selected independently of one another from $C_1$-$C_4$-alkyl, $C_1$-$C_4$-alkoxy, $NR^4R^5$, CN, OH, $C_1$-$C_2$-fluoroalkyl or halogen, $C_2$-$C_6$-alkenyl which is substituted by a radical selected from $OR^3$, $NR^4R^5$, $C(O)NR^4R^5$, O—$C(O)NR^4R^5$, $SR^6$, $SOR^6$, $SO_2R^6$, $SO_2NR^4R^5$, $COOR^7$, O—$C(O)R^8$, $COR^8$, $C_3$-$C_6$-cycloalkyl, 5- or 6-membered heterocyclyl having 1, 2 or 3 heteroatoms selected from O, S and N, and phenyl, where phenyl and heterocyclyl in turn may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen, Ar is an aromatic radical which is selected from phenyl, pyridyl, pyrimidinyl and triazinyl, where the aromatic radical may have 1, 2 or 3 substituents which are selected independently of one another from $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_3$-$C_6$-cycloalkyl, $C_5$-$C_{10}$-bicycloalkyl, $C_6$-$C_{10}$-tricycloalkyl, where the last three groups mentioned may optionally be substituted by halogen or $C_1$-$C_4$-alkyl, or halogen, CN, $OR^{3c}$, $NR^4R^5$, $NO_2$, $SR^6$, $SO_2R^6$, $SO_2NR^4R^5$, $COOR^7$, $COR^8$, 5- or 6-membered heterocyclyl having 1, 2 or 3 heteroatoms selected from O, S and N, and phenyl, where phenyl and heterocyclyl optionally have one or two substituents which are selected independently of one another from $C_1$-$C_4$-alkyl, $C_1$-$C_4$-alkoxy, $NR^4R^5$, CN, $C_1$-$C_2$-fluoroalkyl and halogen, and where 2 substituents bonded to adjacent C atoms of the aromatic radical may together be $C_3$- or $C_4$-alkylene, or may together with the C atoms to which they are bonded be a fused-on, unsaturated 5 or 6-membered carbocycle or a 5- or 6-membered heterocycle having 1 or 2 nitrogen atoms as ring members, $R^3$, $R^{3a}$, $R^{3b}$, $R^{3c}$, $R^{3d}$, $R^4$, $R^5$, $R^6$, $R^7$ and $R^8$ are independently of one another H, $C_1$-$C_6$-alkyl which is optionally substituted by OH, $C_1$-$C_4$-alkoxy or phenyl, or $C_1$-$C_6$-haloalkyl or phenyl, where $R^5$ may also be a group $COR^9$ where $R^9$ is hydrogen, $C_1$-$C_4$-alkyl or phenyl which is optionally substituted by one or two radicals which are selected independently of one another from $C_1$-$C_4$-alkyl, $C_1$-$C_4$-alkoxy, $NR^4R^5$, CN, $C_1$-$C_2$-fluoroalkyl or halogen, where $R^4$ with $R^5$ may also form together with the nitrogen atom to which they are bonded a 4-, 5- or 6-membered saturated or unsaturated heterocycle which may optionally have a further heteroatom selected from O, S and $NR^{10}$ as ring member, where $R^{10}$ is hydrogen or $C_1$-$C_4$-alkyl, and where the heterocycle may optionally carry 1, 2, 3 or 4 $C_1$-$C_4$-alkyl groups, and the derivatives and tautomers of the formulae Ia or Ib

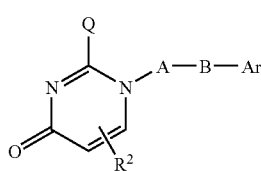

(Ia)

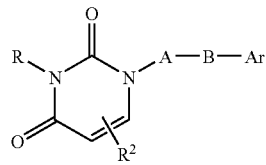

(Ib)

in which R is hydrogen or $C_1$-$C_4$-alkyl, and Q is halogen or a group $OR^{3d}$, and A, B, Ar and $R^2$ have the aforementioned meanings, and by the physiologically tolerated salts of these compounds.

The present invention therefore relates to pyrimidine compounds of the general formula I and to the derivatives and tantomers of the formulae Ia and Ib, and the physiologically acceptable salts thereof.

The present compound additionally relates to a pharmaceutical composition comprising at least one compound of the formulae I, Ia and/or Ib and/or the physiologically acceptable acid addition salts thereof and, where appropriate, one or more physiologically acceptable carriers.

The present invention also relates to the use of a pyrimidinone compound of the formula I, of the derivatives and tantomers thereof of the formulae Ia and Ib and of the salts thereof for producing a pharmaceutical composition for the treatment of disorders which respond to modulation by dopamine $D_3$ receptor ligands.

The disorders which respond to modulation by dopamine $D_3$ receptor ligands include for example impairments and disorders of the central nervous system, especially schizophrenia and depression, Parkinson's and epilepsy, and additionally addictive disorders and impairments of renal function.

The aforementioned indications are treated by using according to the invention at least one compound of the general formulae I, Ia and/or Ib with the meanings specified at the outset. If the compounds of the formula I have one or more centers of asymmetry, it is also possible to employ mixture of enantiomers, especially racemates, mixtures of diastereomers, mixtures of tautomers, but preferably the respective substantially pure enantiomers, diastereomers and tautomers.

It is likewise possible to use physiologically tolerated salts of the compounds of the formulae I, Ia and Ib especially acid addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Further acids which can be used are described in Fortschritte der Arzneimittelforschung, Volume 10, pages 224 et seq., Birkhäuser Verlag, Basle and Stuttgart, 1966.

Halogen here and hereinafter is fluorine, chlorine, bromine or iodine.

$C_n$-$C_m$-Alkyl (also in radicals such as alkoxy, alkylthio, alkylamino etc.) means a straight-chain or branched alkyl group having n to m carbon atoms, e.g. 1 to 6 carbon atoms and in particular 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The alkyl group may have one or more substituents which are selected independently of one another from OH, $C_1$-$C_4$-alkoxy, halogen or phenyl. In the case of a halogen substituent, the alkyl group may include in particular 1, 2, 3 or 4 halogen atoms which may be present on one or more C atoms, preferably in the α- or ω-position. Groups of this type are also referred to hereinafter as haloalkyl. A preferred haloalkyl is $C_1$-$C_2$-fluoroalkyl or $C_1$-$C_2$-fluorochloroalkyl, in particular $CF_3$, $CHF_2$, $CF_2Cl$, $CH_2F$, $CH_2CF_3$.

In the case of hydroxy-substituted alkyl, the alkyl group has in particular one hydroxy group, such as, for example, hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxy-but-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl.

In the case of alkoxy-substituted alkyl, the alkyl group has in particular one alkoxy substituent. These radicals are referred to, depending on the number of carbon atoms, also as $C_n$-$C_m$-alkoxy-$C_n$-$C_m$-alkyl and are, for example, methoxymethyl, ethoxymethyl, 2-methoxyethyl, 1-methoxyethyl, 2-ethoxyethyl, 1-ethoxyethyl, n-propoxymethyl, isopropoxymethyl, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)/propyl, 3-(1-methylpropoxy)-propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl, 2-ethoxyethyl, 2-(methoxy)propyl, 2-(ethoxy)propyl or 3-(methoxy)propyl, 3-(ethoxy)-propyl.

Cycloalkyl is in particular $C_3$-$C_6$-cycloalkyl such as cyclopropyl, cyclobutyl, cyclopentyl and cyclohexyl.

The term "alkylene" includes in principle straight-chain or branched radicals preferably having 3 to 10 and particularly preferably having 3 to 8 carbon atoms, such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-Alkylene is a single bond, $C_1$-alkylene is methylene and $C_2$-alkylene is 1,1-ethylene or 1,2-ethylene.

4, 5- or 6-membered heterocyclyl includes both aromatic heterocyclyl (hetaryl or heteroaryl) and completely saturated or partially unsaturated heterocyclic radicals.

Heterocyclyl has 1, 2 or 3 heteroatoms selected from O, S and N, e.g. 1, 2 or 3 nitrogen atoms, 1 or 2 oxygen atoms, or 1 oxygen atom and 1 or 2 nitrogen atoms or 1 sulfur atom and 1 or 2 nitrogen atoms.

Heterocyclyl may be unsubstituted or have 1 or 2 substituents selected from $C_1$-$C_4$-alkyl, $C_1$-$C_4$-alkoxy, OH, CN, $NR^4R^5$, $C_1$-$C_2$-fluoroalkyl and halogen. Heterocyclyl may additionally have a fused-on 5- or 6-membered carbocycle, e.g. a benzene, cyclopentane or cyclohexene ring or a fused-on heterocycle, e.g. a fused-on pyrrolyfuran, thiophene, thiazole, pyridine, pyrimidine or pyridazine ring.

Examples of saturated heterocyclyl are azetidinyl, pyrrolidinyl, piperidinyl, piperazinyl, morpholinyl, oxolanyl, 1,3-dioxolanyl, 1,3- and 1,4-dioxanyl, 1,3-oxothiolanyl, oxazolidinyl and the like.

Examples of "5- or 6-membered aromatic heterocyclic radicals" which have 1, 2 or 3 heteroatoms which are selected from O, S and N are in particular pyridinyl, pyrimidinyl, pyrazinyl, triazinyl, imidazolyl, pyrrolyl, pyrazolyl, thienyl, furanyl, oxazolyl, thiazolyl, isoxazolyl, tetrazolyl, thiadiazolyl and triazolyl. These may have 1 or 2 of the aforementioned substituents on the nitrogen atoms and on the carbon atoms. Where one of the substituents is hydroxy, the radicals may also exist in a tautomeric form having a carbonyl group. Examples of 5- or 6-membered heterocyclic radicals which have a fused-on carbocycle include benzofuranyl, benzthienyl, indolyl, benzothiazolyl, benzoxazolyl, benzimidazolyl, benzopyrazolyl, quinolinyl, isoquinolinyl, quinoxalinyl, quinazolinyl, cinnolinyl, and corresponding partially hydrogenated groups.

Examples of a fused-on 5 or 6-membered carbocycle are cyclopentene, cyclopentadiene, cyclohexene, cyclohexadiene and benzene. Examples of a fused-on 5- or 6-membered heterocycle having 1 or 2 nitrogen atoms as ring members are pyridine, 1,2,3,4- and 1,2,5,6-tetrahydropyridine, 1,2- and 1,4-dihydrophyridine, pyrimidine, pyrazine and pyridazine.

In group A, the two binding sites of the alkylene chain are preferably located not on the same atom but form, where appropriate with the group Z, a chain which has at least three and preferably at least four members and which separates the pyrimidin-2-one ring from the nitrogen atom of the (partially) saturated nitrogen heterocycle B by at least 4 and preferably by at least 5 bonds from one another. If A has no group Z, then A includes 3 to 6 carbon atoms and preferably 4 or 5 and specifically 4 carbon atoms. If A has at least one of said groups Z, A includes 3 to 6, in particular 3 or 4, carbon atoms and the group Z. Preferred groups Z are O, S and $NR^3$. The heteroatoms of group Z are ordinarily not bonded either to the nitrogen atom of the pyrimidin-2-one ring or to the nitrogen atom of group B. The saturated bonds in alkylene may be replaced by unsaturated bonds (alkenylene; alkynylene). This can result in straight-chain or branched unsaturated groups A in which the number and arrangement of the carbon atoms corresponds to that of the aforementioned alkylene radicals, but where one or more single bonds are replaced by corresponding unsaturated double or triple bonds.

With a view to the use of the compounds of the invention as dopamine $D_3$ receptor ligands, the variables A, B, $R^1$, $R^2$ and Ar preferably have, independently of one another, the meanings indicated below:

A is linear or branched $C_3$-$C_6$-alkylene which includes no group Z, where alkylene may have a double bond. In particularly preferred compounds of the formula I, A is —$(CH_2)_n$-, in which n is 4, 5 or 6 and in particular 4, or A is trans-$CH_2$—CH=CH—$CH_2$—, trans-$CH_2$—C($CH_3$)=CH—$CH_2$—, —$CH_2$—CH($CH_3$)—$CH_2$—$CH_2$— or —$CH_2$—$CH_2$—$CH_2$—CH($CH_3$)—. A is particularly preferably —$(CH_2)_4$—;

B is a bivalent radical of the general formulae:

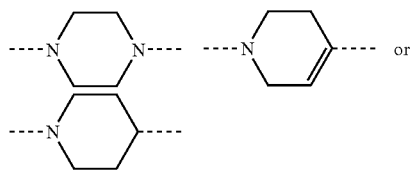 or 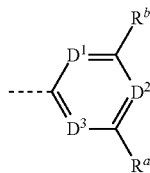

the nitrogen atom therein is linked to group A. B is in particular piperazine-1,4-diyl.

$R^1$ is a group $OR^{3a}$, $NR^4R^5$, $SR^6$, $C_3$-$C_6$-cycloalkyl, $C_1$-$C_4$-alkyl which is optionally substituted by OH, $C_1$-$C_4$-alkoxy, halogen or phenyl, or is 5- or 6-membered aromatic heterocyclyl having 1, 2 or 3 heteroatoms selected from O, S and N, which may be substituted by one or two radicals which are selected independently of one another from $C_1$-$C_4$-alkyl, $C_1$-$C_4$-alkoxy, $NR^4R^5$, CN, OH, $C_1$-$C_2$-fluoroalkyl or halogen, or is phenyl which may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen.

$R^1$ is in particular $C_1$-$C_4$-alkyl, halogen, optionally substituted phenyl, $C_1$-$C_2$-fluoroalkyl, a group $OR^{3a}$, a group $SR^6$ or a radical $NR^4R^5$. In this connection, $R^{3a}$ is in particular hydrogen, $C_1$-$C_4$-alkyl, phenyl or benzyl and specifically hydrogen. $R^4$ is preferably hydrogen or alkyl. $R^5$ is preferably hydrogen, $C_1$-$C_4$-alkyl, phenyl or benzyl or forms together with the nitrogen atom and the radical $R^4$ a 4-, 5- or 6-membered saturated heterocycle such as azetidinyl, pyrrolidinyl, piperidinyl, morpholinyl or piperazinyl. $R^6$ is in this connection preferably hydrogen, $C_1$-$C_4$-alkyl, phenyl or benzyl and in particular hydrogen. Substituted phenyl means in this connection that the phenyl radical may be substituted by one or two radicals, e.g. by $C_1$-$C_4$-alkyl, $C_1$-$C_4$-alkoxy, $NR^4R^5$, OH, CN, $C_1$-$C_2$-fluoroalkyl and/or halogen.

In a particularly preferred embodiment of the invention, $R^1$ is $C_1$-$C_4$-alkyl, in particular methyl, trifluoromethyl or a radical $OR^{3a}$. $R^{3a}$ therein has the aforementioned meanings and is in particular H, $C_1$-$C_4$-alkyl, phenyl or benzyl and specifically H. In this connection, the phenyl ring in phenyl and in benzyl may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen.

$R^2$ is preferably disposed in position 5 of the pyrimidin-2-one ring. $R^2$ is in particular selected from H, $C_1$-$C_4$-alkyl, $C_1$-$C_2$-fluoroalkyl, halogen and cyano, specifically from H, methyl, CN, fluorine and trifluoromethyl. In a particularly preferred embodiment, $R^2$ is $C_1$-$C_4$-alkyl, in particular methyl. In another particularly preferred embodiment, $R^2$ is hydrogen.

A very particularly preferred embodiment of the invention relates to compounds of the formula I in which $R^1$ is $OR^{3a}$ and in particular OH, and $R^2$ is selected in particular from H, fluorine, chlorine, CN and $C_1$-$C_4$-alkyl and specifically hydrogen or methyl.

A further very particularly preferred embodiment of the invention relates to compounds of the formula I in which $R^1$ is methyl, and $R^2$ is selected in particular from H, fluorine, chlorine, CN and $C_1$-$C_4$-alkyl and specifically is hydrogen.

Ar is preferably a radical of the general formula:

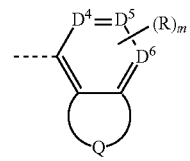

in which at least one of the variables $D^1$ to $D^3$ is N and the other variables $D^1$ to $D^3$ are CH, and $R^a$ and $R^b$ have the meanings indicated above as substituents on Ar, or are hydrogen. Among these, preferred compounds are those in which $D^1$ and $D^2$ are each nitrogen, and $D^3$ is CH. $R^a$ and $R^b$ are preferably independently of one another from the following groups: hydrogen, $OR^{3b}$, $NR^4R^5$, CN, $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_5$-$C_6$-cycloalkyl, $C_5$-$C_{10}$-bicycloalkyl, $C_6$-$C_{10}$-tricycloalkyl, where the last three groups mentioned may optionally be substituted by halogen or $C_1$-$C_4$-alkyl, or halogen, CN, $OR^{3c}$, 5- or 6-membered heterocyclyl having 1, 2 or 3 heteroatoms selected from O, S and N, and phenyl, where phenyl and heterocyclyl optionally have one or two substituents which are selected independently of one another from $C_1$-$C_4$-alkyl, $C_1$-$C_4$-alkoxy, $NR^4R^5$, CN, $C_1$-$C_2$-fluoroalkyl and halogen. Preferably at least one of the radicals $R^a$, $R^b$ and in particular both radicals $R^a$, $R^b$ is/are different from hydrogen. $R^b$ is in particular $C_1$-$C_6$-alkyl, particularly preferably branched $C_3$-$C_6$-alkyl and specifically tert-butyl. $R^a$ is preferably selected from $C_1$-$C_4$-alkyl, $C_3$-$C_6$-cycloalkyl and $C_1$-$C_2$-fluoroalkyl and very particularly preferably from $CF_3$, cyclopentyl and n-propyl. It is particularly preferred for $R^a$ and $R^b$ together to have the meanings indicated as preferred.

Where Ar has a fused-on ring, Ar is preferably a radical of the formula:

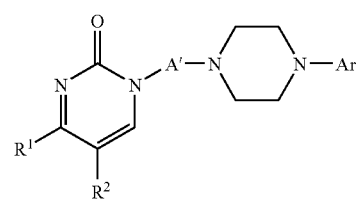

in which $D^4$, $D^5$ and $D^5$ are independently of one another CH or N, Q is linear $C_3$-$C_4$-alkylene, $C_3$-$C_4$-alkenylene or a group CH=CH—N=CH or N=CH—CH=CH, m is 0, 1 or 2, and R is a substituent different from hydrogen, such as $C_1$-$C_4$-alkyl, $C_1$-$C_4$-alkoxy, CN, OH, halogen or $NR^4R^5$.

Among the pyrimidin-2-one compounds of the invention, preference is given to the pyrimidinone compounds of the general formula I.1

(I.1)

in which Ar, $R^1$ and $R^2$ have the aforementioned meanings and in particular the meanings indicated as preferred, and A' is a group —(CH$_2$)$_n$— in which n is 3, 4, 5 or 6 and in particular 4, or A' is one of the following groups: trans-CH$_2$—CH=CH—CH$_2$—, trans-CH$_2$—C(CH$_3$)=CH—CH$_2$—, —CH$_2$—CH(CH$_3$)—CH$_2$—CH$_2$— or —CH$_2$—CH$_2$—CH$_2$—CH(CH$_3$)—.

Preference is likewise given to the derivatives and tautomers of the formulae Ia.1 or Ib.1

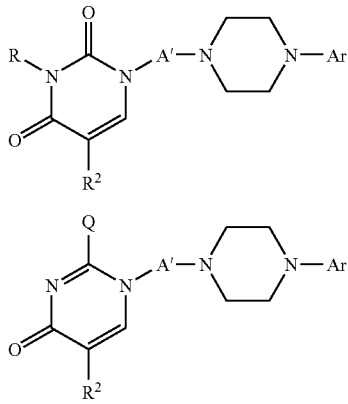

(Ia.1)

(Ib.1)

in which R, A', O, Ar and R$^2$ have the aforementioned meanings and in particular the meanings indicated as preferred.

Otherwise, the groups R$^3$, R$^{3b}$, R$^{3c}$, R$^{3d}$, R$^4$, R$^5$, R$^6$, R$^7$ and R$^8$ preferably have the meanings indicated below:

R$^3$ is preferably H, C$_1$-C$_4$-alkyl, phenyl-substituted C$_1$-C$_4$-alkyl or COR$^{11}$. R$^{11}$ therein has the meanings indicated for R$^8$ and is in particular C$_1$-C$_4$-alkyl. R$^3$ in groups NR$^3$ is preferably H, C$_1$-C$_4$-alkyl, phenyl-substituted C$_1$-C$_4$-alkyl or COR$^{11}$. NR$^3$ is particularly preferably NH, NCH$_3$, NCOCH$_3$ or NCH$_2$-phenyl. R$^3$ in the groups C(O)NR$^3$ and NR$^3$C(O) is preferably H, C$_1$-C$_4$-alkyl, phenyl-substituted C$_1$-C$_4$-alkyl or COR$^{11}$. C(O)NR$^3$ is particularly preferably CONH, CONCH$_3$ or CONCH$_2$-phenyl. NR$^3$C(O) is particularly preferably NHCO, NCH$_3$CO or N(CH$_2$-phenyl)CO.

R$^{3b}$, R$^{3c}$ and R$^{3d}$ are independently of one another preferably H, C$_1$-C$_4$-alkyl, CF$_3$, CHF$_2$ or phenyl. OR$^{3b}$, OR$^{3c}$ and OR$^{3d}$ are particularly preferably methoxy, trifluoromethoxy or phenoxy.

R$^4$ is preferably hydrogen or alkyl. R$^5$ is preferably hydrogen, C$_1$-C$_4$-alkyl, phenyl, benzyl or a group COR$^{11}$. R$^4$ is preferably H or C$_1$-C$_4$-alkyl, and R$^5$ is preferably H, C$_1$-C$_4$-alkyl or COR$^{11}$ in substituent CONR$^4$R$^5$. CONR$^4$R$^5$ is particularly preferably CONH$_2$, CONHCH$_3$, CON(CH$_3$)$_2$ or C(O)NHC(O)CH$_3$. R$^4$ is preferably H, C$_1$-C$_4$-alkyl or phenyl-substituted C$_1$-C$_4$-alkyl, and R$^5$ is H, C$_1$-C$_4$-alkyl or COR$^{11}$ in substituent NR$^4$R$^5$. NR$^4$R$^5$ is particularly preferably NH$_2$, NHCH$_3$, N(CH$_3$)$_2$, NH-benzyl or NHCOCH$_3$. R$^4$ is preferably H or C$_1$-C$_4$-alkyl, and R$^5$ is preferably H, C$_1$-C$_4$-alkyl or COR$^{11}$ in substituent SO$_2$NR$^4$R$^5$. SO$_2$NR$^4$R$^5$ is particularly preferably sulfamoyl. R$^4$ and R$^5$ in the aforementioned groups may also form together with the nitrogen atom to which they are bonded a saturated or unsaturated 4-, 5- or 6-membered, preferably saturated nitrogen heterocycle which may have a further heteroatom such as N, S or O, and which may be substituted by 1, 2, 3 or 4 alkyl groups. Examples of such heterocycles are piperidinyl, morpholinyl, pyrrolidinyl, 4-methylpiperazinyl and 4-methylpiperidinyl.

R$^6$ is preferably H, C$_1$-C$_4$-alkyl, phenyl or benzyl. R$^6$ in substituent SR$^6$ is preferably H, C$_1$-C$_4$-alkyl, phenyl or benzyl. R$^6$ in substituent SOR$^6$ is preferably phenyl or C$_1$-C$_4$-alkyl. R$^6$ in substituent SO$_2$R$^6$ is preferably H or C$_1$-C$_4$-alkyl. SO$_2$R$^6$ is particularly preferably methylsulfonyl.

R$^7$ in substituent COOR$^7$ is H or C$_1$-C$_4$-alkyl. COOR$^7$ is particularly preferably C$_1$-C$_4$-alkoxycarbonyl such as methoxycarbonyl, ethoxycarbonyl, n-propoxycarbonyl, i-propoxycarbonyl, n-butoxycarbonyl or t-butoxycarbonyl.

R$^8$ in substituents COR$^8$ and OC(O)R$^8$ is preferably H, C$_1$-C$_4$-alkyl or phenyl. COR$^8$ is particularly preferably formyl, acetyl or benzoyl.

Among the compounds of the general formula I.1, particularly preferred compounds are those of the general formula I.1a,

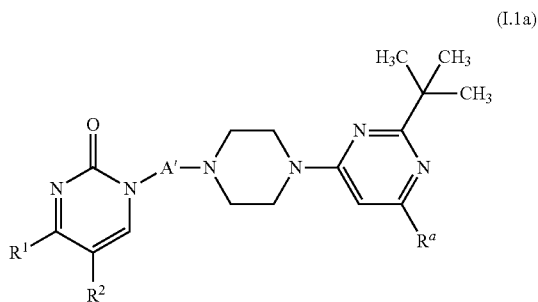

(I.1a)

in which A', R$^1$, R$^2$ and R$^a$ have the meanings indicated above, especially the meanings indicated as preferred. Examples of such compounds are compounds I.1a.1 to I.1a.871 which are listed in Table 1 below and where the variables A', R$^1$, R$^2$ and R$^a$ in each case jointly have the meaning indicated in one line of Table 1.

TABLE 1

|  | R$^1$ | R$^2$ | A' | R$^a$ |
|---|---|---|---|---|
| 1. | OH | H | —(CH$_2$)$_4$— | CF$_3$ |
| 2. | OH | CH$_3$ | —(CH$_2$)$_4$— | CF$_3$ |
| 3. | CH$_3$ | H | —(CH$_2$)$_4$— | CF$_3$ |
| 4. | C(CH$_3$)$_3$ | H | —(CH$_2$)$_4$— | CF$_3$ |
| 5. | C$_6$H$_5$ | H | —(CH$_2$)$_4$— | CF$_3$ |
| 6. | C$_6$H$_5$ | CH$_3$ | —(CH$_2$)$_4$— | CF$_3$ |
| 7. | CF$_3$ | H | —(CH$_2$)$_4$— | CF$_3$ |
| 8. | OH | F | —(CH$_2$)$_4$— | CF$_3$ |
| 9. | OH | CN | —(CH$_2$)$_4$— | CF$_3$ |
| 10. | N(CH$_3$)$_2$ | H | —(CH$_2$)$_4$— | CF$_3$ |
| 11. | N(CH$_3$)$_2$ | CH$_3$ | —(CH$_2$)$_4$— | CF$_3$ |
| 12. | OH | H | trans —CH$_2$—CH=CH—CH$_2$— | CF$_3$ |
| 13. | OH | CH$_3$ | trans —CH$_2$—CH=CH—CH$_2$— | CF$_3$ |
| 14. | CH$_3$ | H | trans —CH$_2$—CH=CH—CH$_2$— | CF$_3$ |
| 15. | C(CH$_3$)$_3$ | H | trans —CH$_2$—CH=CH—CH$_2$— | CF$_3$ |

TABLE 1-continued

| | R¹ | R² | A' | Rᵃ |
|---|---|---|---|---|
| 16. | C₆H₅ | H | trans —CH₂—CH=CH—CH₂— | CF₃ |
| 17. | C₆H₅ | CH₃ | trans —CH₂—CH=CH—CH₂— | CF₃ |
| 18. | CF₃ | H | trans —CH₂—CH=CH—CH₂— | CF₃ |
| 19. | OH | F | trans —CH₂—CH=CH—CH₂— | CF₃ |
| 20. | OH | CN | trans —CH₂—CH=CH—CH₂— | CF₃ |
| 21. | N(CH₃)₂ | H | trans —CH₂—CH=CH—CH₂— | CF₃ |
| 22. | N(CH₃)₂ | CH₃ | trans —CH₂—CH=CH—CH₂— | CF₃ |
| 23. | OH | H | trans —CH₂—C(CH₃)=CH—CH₂— | CF₃ |
| 24. | OH | CH₃ | trans —CH₂—C(CH₃)=CH—CH₂— | CF₃ |
| 25. | CH₃ | H | trans —CH₂—C(CH₃)=CH—CH₂— | CF₃ |
| 26. | C(CH₃)₃ | H | trans —CH₂—C(CH₃)=CH—CH₂— | CF₃ |
| 27. | C₆H₅ | H | trans —CH₂—C(CH₃)=CH—CH₂— | CF₃ |
| 28. | C₆H₅ | CH₃ | trans —CH₂—C(CH₃)=CH—CH₂— | CF₃ |
| 29. | CF₃ | H | trans —CH₂—C(CH₃)=CH—CH₂— | CF₃ |
| 30. | OH | F | trans —CH₂—C(CH₃)=CH—CH₂— | CF₃ |
| 31. | OH | CN | trans —CH₂—C(CH₃)=CH—CH₂— | CF₃ |
| 32. | N(CH₃)₂ | H | trans —CH₂—C(CH₃)=CH—CH₂— | CF₃ |
| 33. | N(CH₃)₂ | CH₃ | trans —CH₂—C(CH₃)=CH—CH₂— | CF₃ |
| 34. | OH | H | —CH₂—CH(CH₃)—CH₂—CH₂— | CF₃ |
| 35. | OH | CH₃ | —CH₂—CH(CH₃)—CH₂—CH₂— | CF₃ |
| 36. | CH₃ | H | —CH₂—CH(CH₃)—CH₂—CH₂— | CF₃ |
| 37. | C(CH₃)₃ | H | —CH₂—CH(CH₃)—CH₂—CH₂— | CF₃ |
| 38. | C₆H₅ | H | —CH₂—CH(CH₃)—CH₂—CH₂— | CF₃ |
| 39. | C₆H₅ | CH₃ | —CH₂—CH(CH₃)—CH₂—CH₂— | CF₃ |
| 40. | CF₃ | H | —CH₂—CH(CH₃)—CH₂—CH₂— | CF₃ |
| 41. | OH | F | —CH₂—CH(CH₃)—CH₂—CH₂— | CF₃ |
| 42. | OH | CN | —CH₂—CH(CH₃)—CH₂—CH₂— | CF₃ |
| 43. | N(CH₃)₂ | H | —CH₂—CH(CH₃)—CH₂—CH₂— | CF₃ |
| 44. | N(CH₃)₂ | CH₃ | —CH₂—CH(CH₃)—CH₂—CH₂— | CF₃ |
| 45. | OH | H | —CH₂—CH₂—CH₂—CH(CH₃)— | CF₃ |
| 46. | OH | CH₃ | —CH₂—CH₂—CH₂—CH(CH₃)— | CF₃ |
| 47. | CH₃ | H | —CH₂—CH₂—CH₂—CH(CH₃)— | CF₃ |
| 48. | C(CH₃)₃ | H | —CH₂—CH₂—CH₂—CH(CH₃)— | CF₃ |
| 49. | C₆H₅ | H | —CH₂—CH₂—CH₂—CH(CH₃)— | CF₃ |
| 50. | C₆H₅ | CH₃ | —CH₂—CH₂—CH₂—CH(CH₃)— | CF₃ |
| 51. | CF₃ | H | —CH₂—CH₂—CH₂—CH(CH₃)— | CF₃ |
| 52. | OH | F | —CH₂—CH₂—CH₂—CH(CH₃)— | CF₃ |
| 53. | OH | CN | —CH₂—CH₂—CH₂—CH(CH₃)— | CF₃ |
| 54. | N(CH₃)₂ | H | —CH₂—CH₂—CH₂—CH(CH₃)— | CF₃ |
| 55. | N(CH₃)₂ | CH₃ | —CH₂—CH₂—CH₂—CH(CH₃)— | CF₃ |
| 56. | OH | H | —(CH₂)₄— | CHF₂ |
| 57. | OH | CH₃ | —(CH₂)₄— | CHF₂ |
| 58. | CH₃ | H | —(CH₂)₄— | CHF₂ |
| 59. | C(CH₃)₃ | H | —(CH₂)₄— | CHF₂ |
| 60. | C₆H₅ | H | —(CH₂)₄— | CHF₂ |
| 61. | C₆H₅ | CH₃ | —(CH₂)₄— | CHF₂ |
| 62. | CF₃ | H | —(CH₂)₄— | CHF₂ |
| 63. | OH | F | —(CH₂)₄— | CHF₂ |
| 64. | OH | CN | —(CH₂)₄— | CHF₂ |
| 65. | N(CH₃)₂ | H | —(CH₂)₄— | CHF₂ |
| 66. | N(CH₃)₂ | CH₃ | —(CH₂)₄— | CHF₂ |
| 67. | OH | H | trans —CH₂—CH=CH—CH₂— | CHF₂ |
| 68. | OH | CH₃ | trans —CH₂—CH=CH—CH₂— | CHF₂ |
| 69. | CH₃ | H | trans —CH₂—CH=CH—CH₂— | CHF₂ |
| 70. | C(CH₃)₃ | H | trans —CH₂—CH=CH—CH₂— | CHF₂ |
| 71. | C₆H₅ | H | trans —CH₂—CH=CH—CH₂— | CHF₂ |
| 72. | C₆H₅ | CH₃ | trans —CH₂—CH=CH—CH₂— | CHF₂ |
| 73. | CF₃ | H | trans —CH₂—CH=CH—CH₂— | CHF₂ |
| 74. | OH | F | trans —CH₂—CH=CH—CH₂— | CHF₂ |
| 75. | OH | CN | trans —CH₂—CH=CH—CH₂— | CHF₂ |
| 76. | N(CH₃)₂ | H | trans —CH₂—CH=CH—CH₂— | CHF₂ |
| 77. | N(CH₃)₂ | CH₃ | trans —CH₂—CH=CH—CH₂— | CHF₂ |
| 78. | OH | H | trans —CH₂—C(CH₃)=CH—CH₂— | CHF₂ |
| 79. | OH | CH₃ | trans —CH₂—C(CH₃)=CH—CH₂— | CHF₂ |
| 80. | CH₃ | H | trans —CH₂—C(CH₃)=CH—CH₂— | CHF₂ |
| 81. | C(CH₃)₃ | H | trans —CH₂—C(CH₃)=CH—CH₂— | CHF₂ |
| 82. | C₆H₅ | H | trans —CH₂—C(CH₃)=CH—CH₂— | CHF₂ |
| 83. | C₆H₅ | CH₃ | trans —CH₂—C(CH₃)=CH—CH₂— | CHF₂ |
| 84. | CF₃ | H | trans —CH₂—C(CH₃)=CH—CH₂— | CHF₂ |
| 85. | OH | F | trans —CH₂—C(CH₃)=CH—CH₂— | CHF₂ |
| 86. | OH | CN | trans —CH₂—C(CH₃)=CH—CH₂— | CHF₂ |
| 87. | N(CH₃)₂ | H | trans —CH₂—C(CH₃)=CH—CH₂— | CHF₂ |
| 88. | N(CH₃)₂ | CH₃ | trans —CH₂—C(CH₃)=CH—CH₂— | CHF₂ |
| 89. | OH | H | —CH₂—CH(CH₃)—CH₂—CH₂— | CHF₂ |
| 90. | OH | CH₃ | —CH₂—CH(CH₃)—CH₂—CH₂— | CHF₂ |
| 91. | CH₃ | H | —CH₂—CH(CH₃)—CH₂—CH₂— | CHF₂ |
| 92. | C(CH₃)₃ | H | —CH₂—CH(CH₃)—CH₂—CH₂— | CHF₂ |
| 93. | C₆H₅ | H | —CH₂—CH(CH₃)—CH₂—CH₂— | CHF₂ |

TABLE 1-continued

| | R¹ | R² | A' | Rᵃ |
|---|---|---|---|---|
| 94. | C₆H₅ | CH₃ | —CH₂—CH(CH₃)—CH₂—CH₂— | CHF₂ |
| 95. | CF₃ | H | —CH₂—CH(CH₃)—CH₂—CH₂— | CHF₂ |
| 96. | OH | F | —CH₂—CH(CH₃)—CH₂—CH₂— | CHF₂ |
| 97. | OH | CN | —CH₂—CH(CH₃)—CH₂—CH₂— | CHF₂ |
| 98. | N(CH₃)₂ | H | —CH₂—CH(CH₃)—CH₂—CH₂— | CHF₂ |
| 99. | N(CH₃)₂ | CH₃ | —CH₂—CH(CH₃)—CH₂—CH₂— | CHF₂ |
| 100. | OH | H | —CH₂—CH₂—CH₂—CH(CH₃)— | CHF₂ |
| 101. | OH | CH₃ | —CH₂—CH₂—CH₂—CH(CH₃)— | CHF₂ |
| 102. | CH₃ | H | —CH₂—CH₂—CH₂—CH(CH₃)— | CHF₂ |
| 103. | C(CH₃)₃ | H | —CH₂—CH₂—CH₂—CH(CH₃)— | CHF₂ |
| 104. | C₆H₅ | H | —CH₂—CH₂—CH₂—CH(CH₃)— | CHF₂ |
| 105. | C₆H₅ | CH₃ | —CH₂—CH₂—CH₂—CH(CH₃)— | CHF₂ |
| 106. | CF₃ | H | —CH₂—CH₂—CH₂—CH(CH₃)— | CHF₂ |
| 107. | OH | F | —CH₂—CH₂—CH₂—CH(CH₃)— | CHF₂ |
| 108. | OH | CN | —CH₂—CH₂—CH₂—CH(CH₃)— | CHF₂ |
| 109. | N(CH₃)₂ | H | —CH₂—CH₂—CH₂—CH(CH₃)— | CHF₂ |
| 110. | N(CH₃)₂ | CH₃ | —CH₂—CH₂—CH₂—CH(CH₃)— | CHF₂ |
| 111. | OH | H | —(CH₂)₄— | C₆H₅ |
| 112. | OH | CH₃ | —(CH₂)₄— | C₆H₅ |
| 113. | CH₃ | H | —(CH₂)₄— | C₆H₅ |
| 114. | C(CH₃)₃ | H | —(CH₂)₄— | C₆H₅ |
| 115. | C₆H₅ | H | —(CH₂)₄— | C₆H₅ |
| 116. | C₆H₅ | CH₃ | —(CH₂)₄— | C₆H₅ |
| 117. | CF₃ | H | —(CH₂)₄— | C₆H₅ |
| 118. | OH | F | —(CH₂)₄— | C₆H₅ |
| 119. | OH | CN | —(CH₂)₄— | C₆H₅ |
| 120. | N(CH₃)₂ | H | —(CH₂)₄— | C₆H₅ |
| 121. | N(CH₃)₂ | CH₃ | —(CH₂)₄— | C₆H₅ |
| 122. | OH | H | trans —CH₂—CH=CH—CH₂— | C₆H₅ |
| 123. | OH | CH₃ | trans —CH₂—CH=CH—CH₂— | C₆H₅ |
| 124. | CH₃ | H | trans —CH₂—CH=CH—CH₂— | C₆H₅ |
| 125. | C(CH₃)₃ | H | trans —CH₂—CH=CH—CH₂— | C₆H₅ |
| 126. | C₆H₅ | H | trans —CH₂—CH=CH—CH₂— | C₆H₅ |
| 127. | C₆H₅ | CH₃ | trans —CH₂—CH=CH—CH₂— | C₆H₅ |
| 128. | CF₃ | H | trans —CH₂—CH=CH—CH₂— | C₆H₅ |
| 129. | OH | F | trans —CH₂—CH=CH—CH₂— | C₆H₅ |
| 130. | OH | CN | trans —CH₂—CH=CH—CH₂— | C₆H₅ |
| 131. | N(CH₃)₂ | H | trans —CH₂—CH=CH—CH₂— | C₆H₅ |
| 132. | N(CH₃)₂ | CH₃ | trans —CH₂—CH=CH—CH₂— | C₆H₅ |
| 133. | OH | H | trans —CH₂—C(CH₃)=CH—CH₂— | C₆H₅ |
| 134. | OH | CH₃ | trans —CH₂—C(CH₃)=CH—CH₂— | C₆H₅ |
| 135. | CH₃ | H | trans —CH₂—C(CH₃)=CH—CH₂— | C₆H₅ |
| 136. | C(CH₃)₃ | H | trans —CH₂—C(CH₃)=CH—CH₂— | C₆H₅ |
| 137. | C₆H₅ | H | trans —CH₂—C(CH₃)=CH—CH₂— | C₆H₅ |
| 138. | C₆H₅ | CH₃ | trans —CH₂—C(CH₃)=CH—CH₂— | C₆H₅ |
| 139. | CF₃ | H | trans —CH₂—C(CH₃)=CH—CH₂— | C₆H₅ |
| 140. | OH | F | trans —CH₂—C(CH₃)=CH—CH₂— | C₆H₅ |
| 141. | OH | CN | trans —CH₂—C(CH₃)=CH—CH₂— | C₆H₅ |
| 142. | N(CH₃)₂ | H | trans —CH₂—C(CH₃)=CH—CH₂— | C₆H₅ |
| 143. | N(CH₃)₂ | CH₃ | trans —CH₂—C(CH₃)=CH—CH₂— | C₆H₅ |
| 144. | OH | H | —CH₂—CH(CH₃)—CH₂—CH₂— | C₆H₅ |
| 145. | OH | CH₃ | —CH₂—CH(CH₃)—CH₂—CH₂— | C₆H₅ |
| 146. | CH₃ | H | —CH₂—CH(CH₃)—CH₂—CH₂— | C₆H₅ |
| 147. | C(CH₃)₃ | H | —CH₂—CH(CH₃)—CH₂—CH₂— | C₆H₅ |
| 148. | C₆H₅ | H | —CH₂—CH(CH₃)—CH₂—CH₂— | C₆H₅ |
| 149. | C₆H₅ | CH₃ | —CH₂—CH(CH₃)—CH₂—CH₂— | C₆H₅ |
| 150. | CF₃ | H | —CH₂—CH(CH₃)—CH₂—CH₂— | C₆H₅ |
| 151. | OH | F | —CH₂—CH(CH₃)—CH₂—CH₂— | C₆H₅ |
| 152. | OH | CN | —CH₂—CH(CH₃)—CH₂—CH₂— | C₆H₅ |
| 153. | N(CH₃)₂ | H | —CH₂—CH(CH₃)—CH₂—CH₂— | C₆H₅ |
| 154. | N(CH₃)₂ | CH₃ | —CH₂—CH(CH₃)—CH₂—CH₂— | C₆H₅ |
| 155. | OH | H | —CH₂—CH₂—CH₂—CH(CH₃)— | C₆H₅ |
| 156. | OH | CH₃ | —CH₂—CH₂—CH₂—CH(CH₃)— | C₆H₅ |
| 157. | CH₃ | H | —CH₂—CH₂—CH₂—CH(CH₃)— | C₆H₅ |
| 158. | C(CH₃)₃ | H | —CH₂—CH₂—CH₂—CH(CH₃)— | C₆H₅ |
| 159. | C₆H₅ | H | —CH₂—CH₂—CH₂—CH(CH₃)— | C₆H₅ |
| 160. | C₆H₅ | CH₃ | —CH₂—CH₂—CH₂—CH(CH₃)— | C₆H₅ |
| 161. | CF₃ | H | —CH₂—CH₂—CH₂—CH(CH₃)— | C₆H₅ |
| 162. | OH | F | —CH₂—CH₂—CH₂—CH(CH₃)— | C₆H₅ |
| 163. | OH | CN | —CH₂—CH₂—CH₂—CH(CH₃)— | C₆H₅ |
| 164. | N(CH₃)₂ | H | —CH₂—CH₂—CH₂—CH(CH₃)— | C₆H₅ |
| 165. | N(CH₃)₂ | CH₃ | —CH₂—CH₂—CH₂—CH(CH₃)— | C₆H₅ |
| 166. | OH | H | —(CH₂)₄— | C(CH₃)₃ |
| 167. | OH | CH₃ | —(CH₂)₄— | C(CH₃)₃ |
| 168. | CH₃ | H | —(CH₂)₄— | C(CH₃)₃ |
| 169. | C(CH₃)₃ | H | —(CH₂)₄— | C(CH₃)₃ |
| 170. | C₆H₅ | H | —(CH₂)₄— | C(CH₃)₃ |
| 171. | C₆H₅ | CH₃ | —(CH₂)₄— | C(CH₃)₃ |

TABLE 1-continued

| | R¹ | R² | A' | Rᵃ |
|---|---|---|---|---|
| 172. | CF₃ | H | —(CH₂)₄— | C(CH₃)₃ |
| 173. | OH | F | —(CH₂)₄— | C(CH₃)₃ |
| 174. | OH | CN | —(CH₂)₄— | C(CH₃)₃ |
| 175. | N(CH₃)₂ | H | —(CH₂)₄— | C(CH₃)₃ |
| 176. | N(CH₃)₂ | CH₃ | —(CH₂)₄— | C(CH₃)₃ |
| 177. | OH | H | trans —CH₂—CH=CH—CH₂— | C(CH₃)₃ |
| 178. | OH | CH₃ | trans —CH₂—CH=CH—CH₂— | C(CH₃)₃ |
| 179. | CH₃ | H | trans —CH₂—CH=CH—CH₂— | C(CH₃)₃ |
| 180. | C(CH₃)₃ | H | trans —CH₂—CH=CH—CH₂— | C(CH₃)₃ |
| 181. | C₆H₅ | H | trans —CH₂—CH=CH—CH₂— | C(CH₃)₃ |
| 182. | C₆H₅ | CH₃ | trans —CH₂—CH=CH—CH₂— | C(CH₃)₃ |
| 183. | CF₃ | H | trans —CH₂—CH=CH—CH₂— | C(CH₃)₃ |
| 184. | OH | F | trans —CH₂—CH=CH—CH₂— | C(CH₃)₃ |
| 185. | OH | CN | trans —CH₂—CH=CH—CH₂— | C(CH₃)₃ |
| 186. | N(CH₃)₂ | H | trans —CH₂—CH=CH—CH₂— | C(CH₃)₃ |
| 187. | N(CH₃)₂ | CH₃ | trans —CH₂—CH=CH—CH₂— | C(CH₃)₃ |
| 188. | OH | H | trans —CH₂—C(CH₃)=CH—CH₂— | C(CH₃)₃ |
| 189. | OH | CH₃ | trans —CH₂—C(CH₃)=CH—CH₂— | C(CH₃)₃ |
| 190. | CH₃ | H | trans —CH₂—C(CH₃)=CH—CH₂— | C(CH₃)₃ |
| 191. | C(CH₃)₃ | H | trans —CH₂—C(CH₃)=CH—CH₂— | C(CH₃)₃ |
| 192. | C₆H₅ | H | trans —CH₂—C(CH₃)=CH—CH₂— | C(CH₃)₃ |
| 193. | C₆H₅ | CH₃ | trans —CH₂—C(CH₃)=CH—CH₂— | C(CH₃)₃ |
| 194. | CF₃ | H | trans —CH₂—C(CH₃)=CH—CH₂— | C(CH₃)₃ |
| 195. | OH | F | trans —CH₂—C(CH₃)=CH—CH₂— | C(CH₃)₃ |
| 196. | OH | CN | trans —CH₂—C(CH₃)=CH—CH₂— | C(CH₃)₃ |
| 197. | N(CH₃)₂ | H | trans —CH₂—C(CH₃)=CH—CH₂— | C(CH₃)₃ |
| 198. | N(CH₃)₂ | CH₃ | trans —CH₂—C(CH₃)=CH—CH₂— | C(CH₃)₃ |
| 199. | OH | H | —CH₂—CH(CH₃)—CH₂—CH₂— | C(CH₃)₃ |
| 200. | OH | CH₃ | —CH₂—CH(CH₃)—CH₂—CH₂— | C(CH₃)₃ |
| 201. | CH₃ | H | —CH₂—CH(CH₃)—CH₂—CH₂— | C(CH₃)₃ |
| 202. | C(CH₃)₃ | H | —CH₂—CH(CH₃)—CH₂—CH₂— | C(CH₃)₃ |
| 203. | C₆H₅ | H | —CH₂—CH(CH₃)—CH₂—CH₂— | C(CH₃)₃ |
| 204. | C₆H₅ | CH₃ | —CH₂—CH(CH₃)—CH₂—CH₂— | C(CH₃)₃ |
| 205. | CF₃ | H | —CH₂—CH(CH₃)—CH₂—CH₂— | C(CH₃)₃ |
| 206. | OH | F | —CH₂—CH(CH₃)—CH₂—CH₂— | C(CH₃)₃ |
| 207. | OH | CN | —CH₂—CH(CH₃)—CH₂—CH₂— | C(CH₃)₃ |
| 208. | N(CH₃)₂ | H | —CH₂—CH(CH₃)—CH₂—CH₂— | C(CH₃)₃ |
| 209. | N(CH₃)₂ | CH₃ | —CH₂—CH(CH₃)—CH₂—CH₂— | C(CH₃)₃ |
| 210. | OH | H | —CH₂—CH₂—CH₂—CH(CH₃)— | C(CH₃)₃ |
| 211. | OH | CH₃ | —CH₂—CH₂—CH₂—CH(CH₃)— | C(CH₃)₃ |
| 212. | CH₃ | H | —CH₂—CH₂—CH₂—CH(CH₃)— | C(CH₃)₃ |
| 213. | C(CH₃)₃ | H | —CH₂—CH₂—CH₂—CH(CH₃)— | C(CH₃)₃ |
| 214. | C₆H₅ | H | —CH₂—CH₂—CH₂—CH(CH₃)— | C(CH₃)₃ |
| 215. | C₆H₅ | CH₃ | —CH₂—CH₂—CH₂—CH(CH₃)— | C(CH₃)₃ |
| 216. | CF₃ | H | —CH₂—CH₂—CH₂—CH(CH₃)— | C(CH₃)₃ |
| 217. | OH | F | —CH₂—CH₂—CH₂—CH(CH₃)— | C(CH₃)₃ |
| 218. | OH | CN | —CH₂—CH₂—CH₂—CH(CH₃)— | C(CH₃)₃ |
| 219. | N(CH₃)₂ | H | —CH₂—CH₂—CH₂—CH(CH₃)— | C(CH₃)₃ |
| 220. | N(CH₃)₂ | CH₃ | —CH₂—CH₂—CH₂—CH(CH₃)— | C(CH₃)₃ |
| 221. | OH | H | —(CH₂)₄— | cyclo-C₅H₉ |
| 222. | OH | CH₃ | —(CH₂)₄— | cyclo-C₅H₉ |
| 223. | CH₃ | H | —(CH₂)₄— | cyclo-C₅H₉ |
| 224. | C(CH₃)₃ | H | —(CH₂)₄— | cyclo-C₅H₉ |
| 225. | C₆H₅ | H | —(CH₂)₄— | cyclo-C₅H₉ |
| 226. | C₆H₅ | CH₃ | —(CH₂)₄— | cyclo-C₅H₉ |
| 227. | CF₃ | H | —(CH₂)₄— | cyclo-C₅H₉ |
| 228. | OH | F | —(CH₂)₄— | cyclo-C₅H₉ |
| 229. | OH | CN | —(CH₂)₄— | cyclo-C₅H₉ |
| 230. | N(CH₃)₂ | H | —(CH₂)₄— | cyclo-C₅H₉ |
| 231. | N(CH₃)₂ | CH₃ | —(CH₂)₄— | cyclo-C₅H₉ |
| 232. | OH | H | trans —CH₂—CH=CH—CH₂— | cyclo-C₅H₉ |
| 233. | OH | CH₃ | trans —CH₂—CH=CH—CH₂— | cyclo-C₅H₉ |
| 234. | CH₃ | H | trans —CH₂—CH=CH—CH₂— | cyclo-C₅H₉ |
| 235. | C(CH₃)₃ | H | trans —CH₂—CH=CH—CH₂— | cyclo-C₅H₉ |
| 236. | C₆H₅ | H | trans —CH₂—CH=CH—CH₂— | cyclo-C₅H₉ |
| 237. | C₆H₅ | CH₃ | trans —CH₂—CH=CH—CH₂— | cyclo-C₅H₉ |
| 238. | CF₃ | H | trans —CH₂—CH=CH—CH₂— | cyclo-C₅H₉ |
| 239. | OH | F | trans —CH₂—CH=CH—CH₂— | cyclo-C₅H₉ |
| 240. | OH | CN | trans —CH₂—CH=CH—CH₂— | cyclo-C₅H₉ |
| 241. | N(CH₃)₂ | H | trans —CH₂—CH=CH—CH₂— | cyclo-C₅H₉ |
| 242. | N(CH₃)₂ | CH₃ | trans —CH₂—CH=CH—CH₂— | cyclo-C₅H₉ |
| 243. | OH | H | trans —CH₂—C(CH₃)=CH—CH₂— | cyclo-C₅H₉ |
| 244. | OH | CH₃ | trans —CH₂—C(CH₃)=CH—CH₂— | cyclo-C₅H₉ |
| 245. | CH₃ | H | trans —CH₂—C(CH₃)=CH—CH₂— | cyclo-C₅H₉ |
| 246. | C(CH₃)₃ | H | trans —CH₂—C(CH₃)=CH—CH₂— | cyclo-C₅H₉ |
| 247. | C₆H₅ | H | trans —CH₂—C(CH₃)=CH—CH₂— | cyclo-C₅H₉ |
| 248. | C₆H₅ | CH₃ | trans —CH₂—C(CH₃)=CH—CH₂— | cyclo-C₅H₉ |
| 249. | CF₃ | H | trans —CH₂—C(CH₃)=CH—CH₂— | cyclo-C₅H₉ |

TABLE 1-continued

| | R¹ | R² | A' | Rᵃ |
|---|---|---|---|---|
| 250. | OH | F | trans —CH₂—C(CH₃)=CH—CH₂— | cyclo-C₅H₉ |
| 251. | OH | CN | trans —CH₂—C(CH₃)=CH—CH₂— | cyclo-C₅H₉ |
| 252. | N(CH₃)₂ | H | trans —CH₂—C(CH₃)=CH—CH₂— | cyclo-C₅H₉ |
| 253. | N(CH₃)₂ | CH₃ | trans —CH₂—C(CH₃)=CH—CH₂— | cyclo-C₅H₉ |
| 254. | OH | H | —CH₂—CH(CH₃)—CH₂—CH₂— | cyclo-C₅H₉ |
| 255. | OH | CH₃ | —CH₂—CH(CH₃)—CH₂—CH₂— | cyclo-C₅H₉ |
| 256. | CH₃ | H | —CH₂—CH(CH₃)—CH₂—CH₂— | cyclo-C₅H₉ |
| 257. | C(CH₃)₃ | H | —CH₂—CH(CH₃)—CH₂—CH₂— | cyclo-C₅H₉ |
| 258. | C₆H₅ | H | —CH₂—CH(CH₃)—CH₂—CH₂— | cyclo-C₅H₉ |
| 259. | C₆H₅ | CH₃ | —CH₂—CH(CH₃)—CH₂—CH₂— | cyclo-C₅H₉ |
| 260. | CF₃ | H | —CH₂—CH(CH₃)—CH₂—CH₂— | cyclo-C₅H₉ |
| 261. | OH | F | —CH₂—CH(CH₃)—CH₂—CH₂— | cyclo-C₅H₉ |
| 262. | OH | CN | —CH₂—CH(CH₃)—CH₂—CH₂— | cyclo-C₅H₉ |
| 263. | N(CH₃)₂ | H | —CH₂—CH(CH₃)—CH₂—CH₂— | cyclo-C₅H₉ |
| 264. | N(CH₃)₂ | CH₃ | —CH₂—CH(CH₃)—CH₂—CH₂— | cyclo-C₅H₉ |
| 265. | OH | H | —CH₂—CH₂—CH₂—CH(CH₃)— | cyclo-C₅H₉ |
| 266. | OH | CH₃ | —CH₂—CH₂—CH₂—CH(CH₃)— | cyclo-C₅H₉ |
| 267. | CH₃ | H | —CH₂—CH₂—CH₂—CH(CH₃)— | cyclo-C₅H₉ |
| 268. | C(CH₃)₃ | H | —CH₂—CH₂—CH₂—CH(CH₃)— | cyclo-C₅H₉ |
| 269. | C₆H₅ | H | —CH₂—CH₂—CH₂—CH(CH₃)— | cyclo-C₅H₉ |
| 270. | C₆H₅ | CH₃ | —CH₂—CH₂—CH₂—CH(CH₃)— | cyclo-C₅H₉ |
| 271. | CF₃ | H | —CH₂—CH₂—CH₂—CH(CH₃)— | cyclo-C₅H₉ |
| 272. | OH | F | —CH₂—CH₂—CH₂—CH(CH₃)— | cyclo-C₅H₉ |
| 273. | OH | CN | —CH₂—CH₂—CH₂—CH(CH₃)— | cyclo-C₅H₉ |
| 274. | N(CH₃)₂ | H | —CH₂—CH₂—CH₂—CH(CH₃)— | cyclo-C₅H₉ |
| 275. | N(CH₃)₂ | CH₃ | —CH₂—CH₂—CH₂—CH(CH₃)— | cyclo-C₅H₉ |
| 276. | OH | H | —(CH₂)₄— | CH₃ |
| 277. | OH | CH₃ | —(CH₂)₄— | CH₃ |
| 278. | CH₃ | H | —(CH₂)₄— | CH₃ |
| 279. | C(CH₃)₃ | H | —(CH₂)₄— | CH₃ |
| 280. | C₆H₅ | H | —(CH₂)₄— | CH₃ |
| 281. | C₆H₅ | CH₃ | —(CH₂)₄— | CH₃ |
| 282. | CF₃ | H | —(CH₂)₄— | CH₃ |
| 283. | OH | F | —(CH₂)₄— | CH₃ |
| 284. | OH | CN | —(CH₂)₄— | CH₃ |
| 285. | N(CH₃)₂ | H | —(CH₂)₄— | CH₃ |
| 286. | N(CH₃)₂ | CH₃ | —(CH₂)₄— | CH₃ |
| 287. | OH | H | trans —CH₂—CH=CH—CH₂— | CH₃ |
| 288. | OH | CH₃ | trans —CH₂—CH=CH—CH₂— | CH₃ |
| 289. | CH₃ | H | trans —CH₂—CH=CH—CH₂— | CH₃ |
| 290. | C(CH₃)₃ | H | trans —CH₂—CH=CH—CH₂— | CH₃ |
| 291. | C₆H₅ | H | trans —CH₂—CH=CH—CH₂— | CH₃ |
| 292. | C₆H₅ | CH₃ | trans —CH₂—CH=CH—CH₂— | CH₃ |
| 293. | CF₃ | H | trans —CH₂—CH=CH—CH₂— | CH₃ |
| 294. | OH | F | trans —CH₂—CH=CH—CH₂— | CH₃ |
| 295. | OH | CN | trans —CH₂—CH=CH—CH₂— | CH₃ |
| 296. | N(CH₃)₂ | H | trans —CH₂—CH=CH—CH₂— | CH₃ |
| 297. | N(CH₃)₂ | CH₃ | trans —CH₂—CH=CH—CH₂— | CH₃ |
| 298. | OH | H | trans —CH₂—C(CH₃)=CH—CH₂— | CH₃ |
| 299. | OH | CH₃ | trans —CH₂—C(CH₃)=CH—CH₂— | CH₃ |
| 300. | CH₃ | H | trans —CH₂—C(CH₃)=CH—CH₂— | CH₃ |
| 301. | C(CH₃)₃ | H | trans —CH₂—C(CH₃)=CH—CH₂— | CH₃ |
| 302. | C₆H₅ | H | trans —CH₂—C(CH₃)=CH—CH₂— | CH₃ |
| 303. | C₆H₅ | CH₃ | trans —CH₂—C(CH₃)=CH—CH₂— | CH₃ |
| 304. | CF₃ | H | trans —CH₂—C(CH₃)=CH—CH₂— | CH₃ |
| 305. | OH | F | trans —CH₂—C(CH₃)=CH—CH₂— | CH₃ |
| 306. | OH | CN | trans —CH₂—C(CH₃)=CH—CH₂— | CH₃ |
| 307. | N(CH₃)₂ | H | trans —CH₂—C(CH₃)=CH—CH₂— | CH₃ |
| 308. | N(CH₃)₂ | CH₃ | trans —CH₂—C(CH₃)=CH—CH₂— | CH₃ |
| 309. | OH | H | —CH₂—CH(CH₃)—CH₂—CH₂— | CH₃ |
| 310. | OH | CH₃ | —CH₂—CH(CH₃)—CH₂—CH₂— | CH₃ |
| 311. | CH₃ | H | —CH₂—CH(CH₃)—CH₂—CH₂— | CH₃ |
| 312. | C(CH₃)₃ | H | —CH₂—CH(CH₃)—CH₂—CH₂— | CH₃ |
| 313. | C₆H₅ | H | —CH₂—CH(CH₃)—CH₂—CH₂— | CH₃ |
| 314. | C₆H₅ | CH₃ | —CH₂—CH(CH₃)—CH₂—CH₂— | CH₃ |
| 315. | CF₃ | H | —CH₂—CH(CH₃)—CH₂—CH₂— | CH₃ |
| 316. | OH | F | —CH₂—CH(CH₃)—CH₂—CH₂— | CH₃ |
| 317. | OH | CN | —CH₂—CH(CH₃)—CH₂—CH₂— | CH₃ |
| 318. | N(CH₃)₂ | H | —CH₂—CH(CH₃)—CH₂—CH₂— | CH₃ |
| 319. | N(CH₃)₂ | CH₃ | —CH₂—CH(CH₃)—CH₂—CH₂— | CH₃ |
| 320. | OH | H | —CH₂—CH₂—CH₂—CH(CH₃)— | CH₃ |
| 321. | OH | CH₃ | —CH₂—CH₂—CH₂—CH(CH₃)— | CH₃ |
| 322. | CH₃ | H | —CH₂—CH₂—CH₂—CH(CH₃)— | CH₃ |
| 323. | C(CH₃)₃ | H | —CH₂—CH₂—CH₂—CH(CH₃)— | CH₃ |
| 324. | C₆H₅ | H | —CH₂—CH₂—CH₂—CH(CH₃)— | CH₃ |
| 325. | C₆H₅ | CH₃ | —CH₂—CH₂—CH₂—CH(CH₃)— | CH₃ |
| 326. | CF₃ | H | —CH₂—CH₂—CH₂—CH(CH₃)— | CH₃ |
| 327. | OH | F | —CH₂—CH₂—CH₂—CH(CH₃)— | CH₃ |

TABLE 1-continued

| | R¹ | R² | A' | Rᵃ |
|---|---|---|---|---|
| 328. | OH | CN | —CH₂—CH₂—CH₂—CH(CH₃)— | CH₃ |
| 329. | N(CH₃)₂ | H | —CH₂—CH₂—CH₂—CH(CH₃)— | CH₃ |
| 330. | N(CH₃)₂ | CH₃ | —CH₂—CH₂—CH₂—CH(CH₃)— | CH₃ |
| 331. | OH | H | —(CH₂)₄— | CH(CH₃)₂ |
| 332. | OH | CH₃ | —(CH₂)₄— | CH(CH₃)₂ |
| 333. | CH₃ | H | —(CH₂)₄— | CH(CH₃)₂ |
| 334. | C(CH₃)₃ | H | —(CH₂)₄— | CH(CH₃)₂ |
| 335. | C₆H₅ | H | —(CH₂)₄— | CH(CH₃)₂ |
| 336. | C₆H₅ | CH₃ | —(CH₂)₄— | CH(CH₃)₂ |
| 337. | CF₃ | H | —(CH₂)₄— | CH(CH₃)₂ |
| 338. | OH | F | —(CH₂)₄— | CH(CH₃)₂ |
| 339. | OH | CN | —(CH₂)₄— | CH(CH₃)₂ |
| 340. | N(CH₃)₂ | H | —(CH₂)₄— | CH(CH₃)₂ |
| 341. | N(CH₃)₂ | CH₃ | —(CH₂)₄— | CH(CH₃)₂ |
| 342. | OH | H | trans —CH₂—CH=CH—CH₂— | CH(CH₃)₂ |
| 343. | OH | CH₃ | trans —CH₂—CH=CH—CH₂— | CH(CH₃)₂ |
| 344. | CH₃ | H | trans —CH₂—CH=CH—CH₂— | CH(CH₃)₂ |
| 345. | C(CH₃)₃ | H | trans —CH₂—CH=CH—CH₂— | CH(CH₃)₂ |
| 346. | C₆H₅ | H | trans —CH₂—CH=CH—CH₂— | CH(CH₃)₂ |
| 347. | C₆H₅ | CH₃ | trans —CH₂—CH=CH—CH₂— | CH(CH₃)₂ |
| 348. | CF₃ | H | trans —CH₂—CH=CH—CH₂— | CH(CH₃)₂ |
| 349. | OH | F | trans —CH₂—CH=CH—CH₂— | CH(CH₃)₂ |
| 350. | OH | CN | trans —CH₂—CH=CH—CH₂— | CH(CH₃)₂ |
| 351. | N(CH₃)₂ | H | trans —CH₂—CH=CH—CH₂— | CH(CH₃)₂ |
| 352. | N(CH₃)₂ | CH₃ | trans —CH₂—CH=CH—CH₂— | CH(CH₃)₂ |
| 353. | OH | H | trans —CH₂—C(CH₃)=CH—CH₂— | CH(CH₃)₂ |
| 354. | OH | CH₃ | trans —CH₂—C(CH₃)=CH—CH₂— | CH(CH₃)₂ |
| 355. | CH₃ | H | trans —CH₂—C(CH₃)=CH—CH₂— | CH(CH₃)₂ |
| 356. | C(CH₃)₃ | H | trans —CH₂—C(CH₃)=CH—CH₂— | CH(CH₃)₂ |
| 357. | C₆H₅ | H | trans —CH₂—C(CH₃)=CH—CH₂— | CH(CH₃)₂ |
| 358. | C₆H₅ | CH₃ | trans —CH₂—C(CH₃)=CH—CH₂— | CH(CH₃)₂ |
| 359. | CF₃ | H | trans —CH₂—C(CH₃)=CH—CH₂— | CH(CH₃)₂ |
| 360. | OH | F | trans —CH₂—C(CH₃)=CH—CH₂— | CH(CH₃)₂ |
| 361. | OH | CN | trans —CH₂—C(CH₃)=CH—CH₂— | CH(CH₃)₂ |
| 362. | N(CH₃)₂ | H | trans —CH₂—C(CH₃)=CH—CH₂— | CH(CH₃)₂ |
| 363. | N(CH₃)₂ | CH₃ | trans —CH₂—C(CH₃)=CH—CH₂— | CH(CH₃)₂ |
| 364. | OH | H | —CH₂—CH(CH₃)—CH₂—CH₂— | CH(CH₃)₂ |
| 365. | OH | CH₃ | —CH₂—CH(CH₃)—CH₂—CH₂— | CH(CH₃)₂ |
| 366. | CH₃ | H | —CH₂—CH(CH₃)—CH₂—CH₂— | CH(CH₃)₂ |
| 367. | C(CH₃)₃ | H | —CH₂—CH(CH₃)—CH₂—CH₂— | CH(CH₃)₂ |
| 368. | C₆H₅ | H | —CH₂—CH(CH₃)—CH₂—CH₂— | CH(CH₃)₂ |
| 369. | C₆H₅ | CH₃ | —CH₂—CH(CH₃)—CH₂—CH₂— | CH(CH₃)₂ |
| 370. | CF₃ | H | —CH₂—CH(CH₃)—CH₂—CH₂— | CH(CH₃)₂ |
| 371. | OH | F | —CH₂—CH(CH₃)—CH₂—CH₂— | CH(CH₃)₂ |
| 372. | OH | CN | —CH₂—CH(CH₃)—CH₂—CH₂— | CH(CH₃)₂ |
| 373. | N(CH₃)₂ | H | —CH₂—CH(CH₃)—CH₂—CH₂— | CH(CH₃)₂ |
| 374. | N(CH₃)₂ | CH₃ | —CH₂—CH(CH₃)—CH₂—CH₂— | CH(CH₃)₂ |
| 375. | OH | H | —CH₂—CH₂—CH₂—CH(CH₃)— | CH(CH₃)₂ |
| 376. | OH | CH₃ | —CH₂—CH₂—CH₂—CH(CH₃)— | CH(CH₃)₂ |
| 377. | CH₃ | H | —CH₂—CH₂—CH₂—CH(CH₃)— | CH(CH₃)₂ |
| 378. | C(CH₃)₃ | H | —CH₂—CH₂—CH₂—CH(CH₃)— | CH(CH₃)₂ |
| 379. | C₆H₅ | H | —CH₂—CH₂—CH₂—CH(CH₃)— | CH(CH₃)₂ |
| 380. | C₆H₅ | CH₃ | —CH₂—CH₂—CH₂—CH(CH₃)— | CH(CH₃)₂ |
| 381. | CF₃ | H | —CH₂—CH₂—CH₂—CH(CH₃)— | CH(CH₃)₂ |
| 382. | OH | F | —CH₂—CH₂—CH₂—CH(CH₃)— | CH(CH₃)₂ |
| 383. | OH | CN | —CH₂—CH₂—CH₂—CH(CH₃)— | CH(CH₃)₂ |
| 384. | N(CH₃)₂ | H | —CH₂—CH₂—CH₂—CH(CH₃)— | CH(CH₃)₂ |
| 385. | N(CH₃)₂ | CH₃ | —CH₂—CH₂—CH₂—CH(CH₃)— | CH(CH₃)₂ |
| 386. | OH | H | —(CH₂)₄— | CH₂CH₃ |
| 387. | OH | CH₃ | —(CH₂)₄— | CH₂CH₃ |
| 388. | CH₃ | H | —(CH₂)₄— | CH₂CH₃ |
| 389. | C(CH₃)₃ | H | —(CH₂)₄— | CH₂CH₃ |
| 390. | C₆H₅ | H | —(CH₂)₄— | CH₂CH₃ |
| 391. | C₆H₅ | CH₃ | —(CH₂)₄— | CH₂CH₃ |
| 392. | CF₃ | H | —(CH₂)₄— | CH₂CH₃ |
| 393. | OH | F | —(CH₂)₄— | CH₂CH₃ |
| 394. | OH | CN | —(CH₂)₄— | CH₂CH₃ |
| 395. | N(CH₃)₂ | H | —(CH₂)₄— | CH₂CH₃ |
| 396. | N(CH₃)₂ | CH₃ | —(CH₂)₄— | CH₂CH₃ |
| 397. | OH | H | trans —CH₂—CH=CH—CH₂— | CH₂CH₃ |
| 398. | OH | CH₃ | trans —CH₂—CH=CH—CH₂— | CH₂CH₃ |
| 399. | CH₃ | H | trans —CH₂—CH=CH—CH₂— | CH₂CH₃ |
| 400. | C(CH₃)₃ | H | trans —CH₂—CH=CH—CH₂— | CH₂CH₃ |
| 401. | C₆H₅ | H | trans —CH₂—CH=CH—CH₂— | CH₂CH₃ |
| 402. | C₆H₅ | CH₃ | trans —CH₂—CH=CH—CH₂— | CH₂CH₃ |
| 403. | CF₃ | H | trans —CH₂—CH=CH—CH₂— | CH₂CH₃ |
| 404. | OH | F | trans —CH₂—CH=CH—CH₂— | CH₂CH₃ |
| 405. | OH | CN | trans —CH₂—CH=CH—CH₂— | CH₂CH₃ |

TABLE 1-continued

| | R¹ | R² | A' | Rᵃ |
|---|---|---|---|---|
| 406. | N(CH₃)₂ | H | trans —CH₂—CH=CH—CH₂— | CH₂CH₃ |
| 407. | N(CH₃)₂ | CH₃ | trans —CH₂—CH=CH—CH₂— | CH₂CH₃ |
| 408. | OH | H | trans —CH₂—C(CH₃)=CH—CH₂— | CH₂CH₃ |
| 409. | OH | CH₃ | trans —CH₂—C(CH₃)=CH—CH₂— | CH₂CH₃ |
| 410. | CH₃ | H | trans —CH₂—C(CH₃)=CH—CH₂— | CH₂CH₃ |
| 411. | C(CH₃)₃ | H | trans —CH₂—C(CH₃)=CH—CH₂— | CH₂CH₃ |
| 412. | C₆H₅ | H | trans —CH₂—C(CH₃)=CH—CH₂— | CH₂CH₃ |
| 413. | C₆H₅ | CH₃ | trans —CH₂—C(CH₃)=CH—CH₂— | CH₂CH₃ |
| 414. | CF₃ | H | trans —CH₂—C(CH₃)=CH—CH₂— | CH₂CH₃ |
| 415. | OH | F | trans —CH₂—C(CH₃)=CH—CH₂— | CH₂CH₃ |
| 416. | OH | CN | trans —CH₂—C(CH₃)=CH—CH₂— | CH₂CH₃ |
| 417. | N(CH₃)₂ | H | trans —CH₂—C(CH₃)=CH—CH₂— | CH₂CH₃ |
| 418. | N(CH₃)₂ | CH₃ | trans —CH₂—C(CH₃)=CH—CH₂— | CH₂CH₃ |
| 419. | OH | H | —CH₂—CH(CH₃)—CH₂—CH₂— | CH₂CH₃ |
| 420. | OH | CH₃ | —CH₂—CH(CH₃)—CH₂—CH₂— | CH₂CH₃ |
| 421. | CH₃ | H | —CH₂—CH(CH₃)—CH₂—CH₂— | CH₂CH₃ |
| 422. | C(CH₃)₃ | H | —CH₂—CH(CH₃)—CH₂—CH₂— | CH₂CH₃ |
| 423. | C₆H₅ | H | —CH₂—CH(CH₃)—CH₂—CH₂— | CH₂CH₃ |
| 424. | C₆H₅ | CH₃ | —CH₂—CH(CH₃)—CH₂—CH₂— | CH₂CH₃ |
| 425. | CF₃ | H | —CH₂—CH(CH₃)—CH₂—CH₂— | CH₂CH₃ |
| 426. | OH | F | —CH₂—CH(CH₃)—CH₂—CH₂— | CH₂CH₃ |
| 427. | OH | CN | —CH₂—CH(CH₃)—CH₂—CH₂— | CH₂CH₃ |
| 428. | N(CH₃)₂ | H | —CH₂—CH(CH₃)—CH₂—CH₂— | CH₂CH₃ |
| 429. | N(CH₃)₂ | CH₃ | —CH₂—CH(CH₃)—CH₂—CH₂— | CH₂CH₃ |
| 430. | OH | H | —CH₂—CH₂—CH₂—CH(CH₃)— | CH₂CH₃ |
| 431. | OH | CH₃ | —CH₂—CH₂—CH₂—CH(CH₃)— | CH₂CH₃ |
| 432. | CH₃ | H | —CH₂—CH₂—CH₂—CH(CH₃)— | CH₂CH₃ |
| 433. | C(CH₃)₃ | H | —CH₂—CH₂—CH₂—CH(CH₃)— | CH₂CH₃ |
| 434. | C₆H₅ | H | —CH₂—CH₂—CH₂—CH(CH₃)— | CH₂CH₃ |
| 435. | C₆H₅ | CH₃ | —CH₂—CH₂—CH₂—CH(CH₃)— | CH₂CH₃ |
| 436. | CF₃ | H | —CH₂—CH₂—CH₂—CH(CH₃)— | CH₂CH₃ |
| 437. | OH | F | —CH₂—CH₂—CH₂—CH(CH₃)— | CH₂CH₃ |
| 438. | OH | CN | —CH₂—CH₂—CH₂—CH(CH₃)— | CH₂CH₃ |
| 439. | N(CH₃)₂ | H | —CH₂—CH₂—CH₂—CH(CH₃)— | CH₂CH₃ |
| 440. | N(CH₃)₂ | CH₃ | —CH₂—CH₂—CH₂—CH(CH₃)— | CH₂CH₃ |
| 441. | OH | H | —(CH₂)₄— | CH₂CH₂CH₃ |
| 442. | OH | CH₃ | —(CH₂)₄— | CH₂CH₂CH₃ |
| 443. | CH₃ | H | —(CH₂)₄— | CH₂CH₂CH₃ |
| 444. | C(CH₃)₃ | H | —(CH₂)₄— | CH₂CH₂CH₃ |
| 445. | C₆H₅ | H | —(CH₂)₄— | CH₂CH₂CH₃ |
| 446. | C₆H₅ | CH₃ | —(CH₂)₄— | CH₂CH₂CH₃ |
| 447. | CF₃ | H | —(CH₂)₄— | CH₂CH₂CH₃ |
| 448. | OH | F | —(CH₂)₄— | CH₂CH₂CH₃ |
| 449. | OH | CN | —(CH₂)₄— | CH₂CH₂CH₃ |
| 450. | N(CH₃)₂ | H | —(CH₂)₄— | CH₂CH₂CH₃ |
| 451. | N(CH₃)₂ | CH₃ | —(CH₂)₄— | CH₂CH₂CH₃ |
| 452. | OH | H | trans —CH₂—CH=CH—CH₂— | CH₂CH₂CH₃ |
| 453. | OH | CH₃ | trans —CH₂—CH=CH—CH₂— | CH₂CH₂CH₃ |
| 454. | CH₃ | H | trans —CH₂—CH=CH—CH₂— | CH₂CH₂CH₃ |
| 455. | C(CH₃)₃ | H | trans —CH₂—CH=CH—CH₂— | CH₂CH₂CH₃ |
| 456. | C₆H₅ | H | trans —CH₂—CH=CH—CH₂— | CH₂CH₂CH₃ |
| 457. | C₆H₅ | CH₃ | trans —CH₂—CH=CH—CH₂— | CH₂CH₂CH₃ |
| 458. | CF₃ | H | trans —CH₂—CH=CH—CH₂— | CH₂CH₂CH₃ |
| 459. | OH | F | trans —CH₂—CH=CH—CH₂— | CH₂CH₂CH₃ |
| 460. | OH | CN | trans —CH₂—CH=CH—CH₂— | CH₂CH₂CH₃ |
| 461. | N(CH₃)₂ | H | trans —CH₂—CH=CH—CH₂— | CH₂CH₂CH₃ |
| 462. | N(CH₃)₂ | CH₃ | trans —CH₂—CH=CH—CH₂— | CH₂CH₂CH₃ |
| 463. | OH | H | trans —CH₂—C(CH₃)=CH—CH₂— | CH₂CH₂CH₃ |
| 464. | OH | CH₃ | trans —CH₂—C(CH₃)=CH—CH₂— | CH₂CH₂CH₃ |
| 465. | CH₃ | H | trans —CH₂—C(CH₃)=CH—CH₂— | CH₂CH₂CH₃ |
| 466. | C(CH₃)₃ | H | trans —CH₂—C(CH₃)=CH—CH₂— | CH₂CH₂CH₃ |
| 467. | C₆H₅ | H | trans —CH₂—C(CH₃)=CH—CH₂— | CH₂CH₂CH₃ |
| 468. | C₆H₅ | CH₃ | trans —CH₂—C(CH₃)=CH—CH₂— | CH₂CH₂CH₃ |
| 469. | CF₃ | H | trans —CH₂—C(CH₃)=CH—CH₂— | CH₂CH₂CH₃ |
| 470. | OH | F | trans —CH₂—C(CH₃)=CH—CH₂— | CH₂CH₂CH₃ |
| 471. | OH | CN | trans —CH₂—C(CH₃)=CH—CH₂— | CH₂CH₂CH₃ |
| 472. | N(CH₃)₂ | H | trans —CH₂—C(CH₃)=CH—CH₂— | CH₂CH₂CH₃ |
| 473. | N(CH₃)₂ | CH₃ | trans —CH₂—C(CH₃)=CH—CH₂— | CH₂CH₂CH₃ |
| 474. | OH | H | —CH₂—CH(CH₃)—CH₂—CH₂— | CH₂CH₂CH₃ |
| 475. | OH | CH₃ | —CH₂—CH(CH₃)—CH₂—CH₂— | CH₂CH₂CH₃ |
| 476. | CH₃ | H | —CH₂—CH(CH₃)—CH₂—CH₂— | CH₂CH₂CH₃ |
| 477. | C(CH₃)₃ | H | —CH₂—CH(CH₃)—CH₂—CH₂— | CH₂CH₂CH₃ |
| 478. | C₆H₅ | H | —CH₂—CH(CH₃)—CH₂—CH₂— | CH₂CH₂CH₃ |
| 479. | C₆H₅ | CH₃ | —CH₂—CH(CH₃)—CH₂—CH₂— | CH₂CH₂CH₃ |
| 480. | CF₃ | H | —CH₂—CH(CH₃)—CH₂—CH₂— | CH₂CH₂CH₃ |
| 481. | OH | F | —CH₂—CH(CH₃)—CH₂—CH₂— | CH₂CH₂CH₃ |
| 482. | OH | CN | —CH₂—CH(CH₃)—CH₂—CH₂— | CH₂CH₂CH₃ |
| 483. | N(CH₃)₂ | H | —CH₂—CH(CH₃)—CH₂—CH₂— | CH₂CH₂CH₃ |

TABLE 1-continued

| | R¹ | R² | A' | Rᵃ |
|---|---|---|---|---|
| 484. | N(CH₃)₂ | CH₃ | —CH₂—CH(CH₃)—CH₂—CH₂— | CH₂CH₂CH₃ |
| 485. | OH | H | —CH₂—CH₂—CH₂—CH(CH₃)— | CH₂CH₂CH₃ |
| 486. | OH | CH₃ | —CH₂—CH₂—CH₂—CH(CH₃)— | CH₂CH₂CH₃ |
| 487. | CH₃ | H | —CH₂—CH₂—CH₂—CH(CH₃)— | CH₂CH₂CH₃ |
| 488. | C(CH₃)₃ | H | —CH₂—CH₂—CH₂—CH(CH₃)— | CH₂CH₂CH₃ |
| 489. | C₆H₅ | H | —CH₂—CH₂—CH₂—CH(CH₃)— | CH₂CH₂CH₃ |
| 490. | C₆H₅ | CH₃ | —CH₂—CH₂—CH₂—CH(CH₃)— | CH₂CH₂CH₃ |
| 491. | CF₃ | H | —CH₂—CH₂—CH₂—CH(CH₃)— | CH₂CH₂CH₃ |
| 492. | OH | F | —CH₂—CH₂—CH₂—CH(CH₃)— | CH₂CH₂CH₃ |
| 493. | OH | CN | —CH₂—CH₂—CH₂—CH(CH₃)— | CH₂CH₂CH₃ |
| 494. | N(CH₃)₂ | H | —CH₂—CH₂—CH₂—CH(CH₃)— | CH₂CH₂CH₃ |
| 495. | N(CH₃)₂ | CH₃ | —CH₂—CH₂—CH₂—CH(CH₃)— | CH₂CH₂CH₃ |
| 496. | 1-Methylpyrrol-2-yl | H | —(CH₂)₄— | CF₃ |
| 497. | 3-Pyridyl | H | —(CH₂)₄— | CF₃ |
| 498. | 3-Thienyl | H | —(CH₂)₄— | CF₃ |
| 499. | 4-Fluorophenyl | H | —(CH₂)₄— | CF₃ |
| 500. | 4-Pyridyl | H | —(CH₂)₄— | CF₃ |
| 501. | 3-Furyl | H | —(CH₂)₄— | CF₃ |
| 502. | 2-Furyl | H | —(CH₂)₄— | CF₃ |
| 503. | 2-Pyrrolyl | H | —(CH₂)₄— | CF₃ |
| 504. | 2-Thienyl | H | —(CH₂)₄— | CF₃ |
| 505. | Pyridazin-2-yl | H | —(CH₂)₄— | CF₃ |
| 506. | 4-Methylthiazol-5-yl | H | —(CH₂)₄— | CF₃ |
| 507. | 2-Methyloxazol-4-yl | H | —(CH₂)₄— | CF₃ |
| 508. | Cyclopropyl | H | —(CH₂)₄— | CF₃ |
| 509. | Cyclobutyl | H | —(CH₂)₄— | CF₃ |
| 510. | Cyclopentyl | H | —(CH₂)₄— | CF₃ |
| 511. | Cyclohexyl | H | —(CH₂)₄— | CF₃ |
| 512. | H₃C—O—CH₂ | H | —(CH₂)₄— | CF₃ |
| 513. | Oxan-4-yl | H | —(CH₂)₄— | CF₃ |
| 514. | 1-Methylpiperidin-4-yl | H | —(CH₂)₄— | CF₃ |
| 515. | 1-Methylpyrrol-2-yl | H | trans —CH₂—CH=CH—CH₂— | CF₃ |
| 516. | 3-Pyridyl | H | trans —CH₂—CH=CH—CH₂— | CF₃ |
| 517. | 3-Thienyl | H | trans —CH₂—CH=CH—CH₂— | CF₃ |
| 518. | 4-Fluorophenyl | H | trans —CH₂—CH=CH—CH₂— | CF₃ |
| 519. | 4-Pyridyl | H | trans —CH₂—CH=CH—CH₂— | CF₃ |
| 520. | 3-Furyl | H | trans —CH₂—CH=CH—CH₂— | CF₃ |
| 521. | 2-Furyl | H | trans —CH₂—CH=CH—CH₂— | CF₃ |
| 522. | 2-Pyrrolyl | H | trans —CH₂—CH=CH—CH₂— | CF₃ |
| 523. | 2-Thienyl | H | trans —CH₂—CH=CH—CH₂— | CF₃ |
| 524. | Pyridazin-2-yl | H | trans —CH₂—CH=CH—CH₂— | CF₃ |
| 525. | 4-Methylthiazol-5-yl | H | trans —CH₂—CH=CH—CH₂— | CF₃ |
| 526. | 2-Methyloxazol-4-yl | H | trans —CH₂—CH=CH—CH₂— | CF₃ |
| 527. | Cyclopropyl | H | trans —CH₂—CH=CH—CH₂— | CF₃ |
| 528. | Cyclobutyl | H | trans —CH₂—CH=CH—CH₂— | CF₃ |
| 529. | Cyclopentyl | H | trans —CH₂—CH=CH—CH₂— | CF₃ |
| 530. | Cyclohexyl | H | trans —CH₂—CH=CH—CH₂— | CF₃ |
| 531. | H₃C—O—CH₂ | H | trans —CH₂—CH=CH—CH₂— | CF₃ |
| 532. | Oxan-4-yl | H | trans —CH₂—CH=CH—CH₂— | CF₃ |
| 533. | 1-Methylpiperidin-4-yl | H | trans —CH₂—CH=CH—CH₂— | CF₃ |
| 534. | 1-Methylpyrrol-2-yl | H | —(CH₂)₄— | CH₂CH₂CH₃ |
| 535. | 3-Pyridyl | H | —(CH₂)₄— | CH₂CH₂CH₃ |
| 536. | 3-Thienyl | H | —(CH₂)₄— | CH₂CH₂CH₃ |
| 537. | 4-Fluorophenyl | H | —(CH₂)₄— | CH₂CH₂CH₃ |
| 538. | 4-Pyridyl | H | —(CH₂)₄— | CH₂CH₂CH₃ |
| 539. | 3-Furyl | H | —(CH₂)₄— | CH₂CH₂CH₃ |
| 540. | 2-Furyl | H | —(CH₂)₄— | CH₂CH₂CH₃ |
| 541. | 2-Pyrrolyl | H | —(CH₂)₄— | CH₂CH₂CH₃ |
| 542. | 2-Thienyl | H | —(CH₂)₄— | CH₂CH₂CH₃ |
| 543. | Pyridazin-2-yl | H | —(CH₂)₄— | CH₂CH₂CH₃ |
| 544. | 4-Methylthiazol-5-yl | H | —(CH₂)₄— | CH₂CH₂CH₃ |
| 545. | 2-Methyloxazol-4-yl | H | —(CH₂)₄— | CH₂CH₂CH₃ |
| 546. | Cyclopropyl | H | —(CH₂)₄— | CH₂CH₂CH₃ |
| 547. | Cyclobutyl | H | —(CH₂)₄— | CH₂CH₂CH₃ |
| 548. | Cyclopentyl | H | —(CH₂)₄— | CH₂CH₂CH₃ |
| 549. | Cyclohexyl | H | —(CH₂)₄— | CH₂CH₂CH₃ |
| 550. | H₃C—O—CH₂ | H | —(CH₂)₄— | CH₂CH₂CH₃ |
| 551. | Oxan-4-yl | H | —(CH₂)₄— | CH₂CH₂CH₃ |
| 552. | 1-Methylpiperidin-4-yl | H | —(CH₂)₄— | CH₂CH₂CH₃ |
| 553. | 1-Methylpyrrol-2-yl | H | trans —CH₂—CH=CH—CH₂— | CH₂CH₂CH₃ |
| 554. | 3-Pyridyl | H | trans —CH₂—CH=CH—CH₂— | CH₂CH₂CH₃ |
| 555. | 3-Thienyl | H | trans —CH₂—CH=CH—CH₂— | CH₂CH₂CH₃ |
| 556. | 4-Fluorophenyl | H | trans —CH₂—CH=CH—CH₂— | CH₂CH₂CH₃ |
| 557. | 4-Pyridyl | H | trans —CH₂—CH=CH—CH₂— | CH₂CH₂CH₃ |
| 558. | 3-Furyl | H | trans —CH₂—CH=CH—CH₂— | CH₂CH₂CH₃ |
| 559. | 2-Furyl | H | trans —CH₂—CH=CH—CH₂— | CH₂CH₂CH₃ |
| 560. | 2-Pyrrolyl | H | trans —CH₂—CH=CH—CH₂— | CH₂CH₂CH₃ |
| 561. | 2-Thienyl | H | trans —CH₂—CH=CH—CH₂— | CH₂CH₂CH₃ |

TABLE 1-continued

| | R¹ | R² | A' | Rᵃ |
|---|---|---|---|---|
| 562. | Pyridazin-2-yl | H | trans —CH₂—CH=CH—CH₂— | CH₂CH₂CH₃ |
| 563. | 4-Methylthiazol-5-yl | H | trans —CH₂—CH=CH—CH₂— | CH₂CH₂CH₃ |
| 564. | 2-Methyloxazol-4-yl | H | trans —CH₂—CH=CH—CH₂— | CH₂CH₂CH₃ |
| 565. | Cyclopropyl | H | trans —CH₂—CH=CH—CH₂— | CH₂CH₂CH₃ |
| 566. | Cyclobutyl | H | trans —CH₂—CH=CH—CH₂— | CH₂CH₂CH₃ |
| 567. | Cyclopentyl | H | trans —CH₂—CH=CH—CH₂— | CH₂CH₂CH₃ |
| 568. | Cyclohexyl | H | trans —CH₂—CH=CH—CH₂— | CH₂CH₂CH₃ |
| 569. | H₃C—O—CH₂ | H | trans —CH₂—CH=CH—CH₂— | CH₂CH₂CH₃ |
| 570. | Oxan-4-yl | H | trans —CH₂—CH=CH—CH₂— | CH₂CH₂CH₃ |
| 571. | 1-Methylpiperidin-4-yl | H | trans —CH₂—CH=CH—CH₂— | CH₂CH₂CH₃ |
| 572. | 1-Methylpyrrol-2-yl | H | —(CH₂)₄— | CH₃ |
| 573. | 3-Pyridyl | H | —(CH₂)₄— | CH₃ |
| 574. | 3-Thienyl | H | —(CH₂)₄— | CH₃ |
| 575. | 4-Fluorophenyl | H | —(CH₂)₄— | CH₃ |
| 576. | 4-Pyridyl | H | —(CH₂)₄— | CH₃ |
| 577. | 3-Furyl | H | —(CH₂)₄— | CH₃ |
| 578. | 2-Furyl | H | —(CH₂)₄— | CH₃ |
| 579. | 2-Pyrrolyl | H | —(CH₂)₄— | CH₃ |
| 580. | 2-Thienyl | H | —(CH₂)₄— | CH₃ |
| 581. | Pyridazin-2-yl | H | —(CH₂)₄— | CH₃ |
| 582. | 4-Methylthiazol-5-yl | H | —(CH₂)₄— | CH₃ |
| 583. | 2-Methyloxazol-4-yl | H | —(CH₂)₄— | CH₃ |
| 584. | Cyclopropyl | H | —(CH₂)₄— | CH₃ |
| 585. | Cyclobutyl | H | —(CH₂)₄— | CH₃ |
| 586. | Cyclopentyl | H | —(CH₂)₄— | CH₃ |
| 587. | Cyclohexyl | H | —(CH₂)₄— | CH₃ |
| 588. | H₃C—O—CH₂ | H | —(CH₂)₄— | CH₃ |
| 589. | Oxan-4-yl | H | —(CH₂)₄— | CH₃ |
| 590. | 1-Methylpiperidin-4-yl | H | —(CH₂)₄— | CH₃ |
| 591. | 1-Methylpyrrol-2-yl | H | trans —CH₂—CH=CH—CH₂— | CH₃ |
| 592. | 3-Pyridyl | H | trans —CH₂—CH=CH—CH₂— | CH₃ |
| 593. | 3-Thienyl | H | trans —CH₂—CH=CH—CH₂— | CH₃ |
| 594. | 4-Fluorophenyl | H | trans —CH₂—CH=CH—CH₂— | CH₃ |
| 595. | 4-Pyridyl | H | trans —CH₂—CH=CH—CH₂— | CH₃ |
| 596. | 3-Furyl | H | trans —CH₂—CH=CH—CH₂— | CH₃ |
| 597. | 2-Furyl | H | trans —CH₂—CH=CH—CH₂— | CH₃ |
| 598. | 2-Pyrrolyl | H | trans —CH₂—CH=CH—CH₂— | CH₃ |
| 599. | 2-Thienyl | H | trans —CH₂—CH=CH—CH₂— | CH₃ |
| 600. | Pyridazin-2-yl | H | trans —CH₂—CH=CH—CH₂— | CH₃ |
| 601. | 4-Methylthiazol-5-yl | H | trans —CH₂—CH=CH—CH₂— | CH₃ |
| 602. | 2-Methyloxazol-4-yl | H | trans —CH₂—CH=CH—CH₂— | CH₃ |
| 603. | Cyclopropyl | H | trans —CH₂—CH=CH—CH₂— | CH₃ |
| 604. | Cyclobutyl | H | trans —CH₂—CH=CH—CH₂— | CH₃ |
| 605. | Cyclopentyl | H | trans —CH₂—CH=CH—CH₂— | CH₃ |
| 606. | Cyclohexyl | H | trans —CH₂—CH=CH—CH₂— | CH₃ |
| 607. | H₃C—O—CH₂ | H | trans —CH₂—CH=CH—CH₂— | CH₃ |
| 608. | Oxan-4-yl | H | trans —CH₂—CH=CH—CH₂— | CH₃ |
| 609. | 1-Methylpiperidin-4-yl | H | trans —CH₂—CH=CH—CH₂— | CH₃ |
| 610. | 1-Methylpyrrol-2-yl | H | —(CH₂)₄— | C(CH₃)₃ |
| 611. | 3-Pyridyl | H | —(CH₂)₄— | C(CH₃)₃ |
| 612. | 3-Thienyl | H | —(CH₂)₄— | C(CH₃)₃ |
| 613. | 4-Fluorophenyl | H | —(CH₂)₄— | C(CH₃)₃ |
| 614. | 4-Pyridyl | H | —(CH₂)₄— | C(CH₃)₃ |
| 615. | 3-Furyl | H | —(CH₂)₄— | C(CH₃)₃ |
| 616. | 2-Furyl | H | —(CH₂)₄— | C(CH₃)₃ |
| 617. | 2-Pyrrolyl | H | —(CH₂)₄— | C(CH₃)₃ |
| 618. | 2-Thienyl | H | —(CH₂)₄— | C(CH₃)₃ |
| 619. | Pyridazin-2-yl | H | —(CH₂)₄— | C(CH₃)₃ |
| 620. | 4-Methylthiazol-5-yl | H | —(CH₂)₄— | C(CH₃)₃ |
| 621. | 2-Methyloxazol-4-yl | H | —(CH₂)₄— | C(CH₃)₃ |
| 622. | Cyclopropyl | H | —(CH₂)₄— | C(CH₃)₃ |
| 623. | Cyclobutyl | H | —(CH₂)₄— | C(CH₃)₃ |
| 624. | Cyclopentyl | H | —(CH₂)₄— | C(CH₃)₃ |
| 625. | Cyclohexyl | H | —(CH₂)₄— | C(CH₃)₃ |
| 626. | H₃C—O—CH₂ | H | —(CH₂)₄— | C(CH₃)₃ |
| 627. | Oxan-4-yl | H | —(CH₂)₄— | C(CH₃)₃ |
| 628. | 1-Methylpiperidin-4-yl | H | —(CH₂)₄— | C(CH₃)₃ |
| 629. | 1-Methylpyrrol-2-yl | H | trans —CH₂—CH=CH—CH₂— | C(CH₃)₃ |
| 630. | 3-Pyridyl | H | trans —CH₂—CH=CH—CH₂— | C(CH₃)₃ |
| 631. | 3-Thienyl | H | trans —CH₂—CH=CH—CH₂— | C(CH₃)₃ |
| 632. | 4-Fluorophenyl | H | trans —CH₂—CH=CH—CH₂— | C(CH₃)₃ |
| 633. | 4-Pyridyl | H | trans —CH₂—CH=CH—CH₂— | C(CH₃)₃ |
| 634. | 3-Furyl | H | trans —CH₂—CH=CH—CH₂— | C(CH₃)₃ |
| 635. | 2-Furyl | H | trans —CH₂—CH=CH—CH₂— | C(CH₃)₃ |
| 636. | 2-Pyrrolyl | H | trans —CH₂—CH=CH—CH₂— | C(CH₃)₃ |
| 637. | 2-Thienyl | H | trans —CH₂—CH=CH—CH₂— | C(CH₃)₃ |
| 638. | Pyridazin-2-yl | H | trans —CH₂—CH=CH—CH₂— | C(CH₃)₃ |
| 639. | 4-Methylthiazol-5-yl | H | trans —CH₂—CH=CH—CH₂— | C(CH₃)₃ |

TABLE 1-continued

| | R¹ | R² | A' | Rᵃ |
|---|---|---|---|---|
| 640. | 2-Methyloxazol-4-yl | H | trans —CH₂—CH=CH—CH₂— | C(CH₃)₃ |
| 641. | Cyclopropyl | H | trans —CH₂—CH=CH—CH₂— | C(CH₃)₃ |
| 642. | Cyclobutyl | H | trans —CH₂—CH=CH—CH₂— | C(CH₃)₃ |
| 643. | Cyclopentyl | H | trans —CH₂—CH=CH—CH₂— | C(CH₃)₃ |
| 644. | Cyclohexyl | H | trans —CH₂—CH=CH—CH₂— | C(CH₃)₃ |
| 645. | H₃C—O—CH₂ | H | trans —CH₂—CH=CH—CH₂— | C(CH₃)₃ |
| 646. | Oxan-4-yl | H | trans —CH₂—CH=CH—CH₂— | C(CH₃)₃ |
| 647. | 1-Methylpiperidin-4-yl | H | trans —CH₂—CH=CH—CH₂— | C(CH₃)₃ |
| 648. | 1-Methylpyrrol-2-yl | H | —(CH₂)₄— | cyclo-C₅H₉ |
| 649. | 3-Pyridyl | H | —(CH₂)₄— | cyclo-C₅H₉ |
| 650. | 3-Thienyl | H | —(CH₂)₄— | cyclo-C₅H₉ |
| 651. | 4-Fluorophenyl | H | —(CH₂)₄— | cyclo-C₅H₉ |
| 652. | 4-Pyridyl | H | —(CH₂)₄— | cyclo-C₅H₉ |
| 653. | 3-Furyl | H | —(CH₂)₄— | cyclo-C₅H₉ |
| 654. | 2-Furyl | H | —(CH₂)₄— | cyclo-C₅H₉ |
| 655. | 2-Pyrrolyl | H | —(CH₂)₄— | cyclo-C₅H₉ |
| 656. | 2-Thienyl | H | —(CH₂)₄— | cyclo-C₅H₉ |
| 657. | Pyridazin-2-yl | H | —(CH₂)₄— | cyclo-C₅H₉ |
| 658. | 4-Methylthiazol-5-yl | H | —(CH₂)₄— | cyclo-C₅H₉ |
| 659. | 2-Methyloxazol-4-yl | H | —(CH₂)₄— | cyclo-C₅H₉ |
| 660. | Cyclopropyl | H | —(CH₂)₄— | cyclo-C₅H₉ |
| 661. | Cyclobutyl | H | —(CH₂)₄— | cyclo-C₅H₉ |
| 662. | Cyclopentyl | H | —(CH₂)₄— | cyclo-C₅H₉ |
| 663. | Cyclohexyl | H | —(CH₂)₄— | cyclo-C₅H₉ |
| 664. | H₃C—O—CH₂ | H | —(CH₂)₄— | cyclo-C₅H₉ |
| 665. | Oxan-4-yl | H | —(CH₂)₄— | cyclo-C₅H₉ |
| 666. | 1-Methylpiperidin-4-yl | H | —(CH₂)₄— | cyclo-C₅H₉ |
| 667. | 1-Methylpyrrol-2-yl | H | trans —CH₂—CH=CH—CH₂— | cyclo-C₅H₉ |
| 668. | 3-Pyridyl | H | trans —CH₂—CH=CH—CH₂— | cyclo-C₅H₉ |
| 669. | 3-Thienyl | H | trans —CH₂—CH=CH—CH₂— | cyclo-C₅H₉ |
| 670. | 4-Fluorophenyl | H | trans —CH₂—CH=CH—CH₂— | cyclo-C₅H₉ |
| 671. | 4-Pyridyl | H | trans —CH₂—CH=CH—CH₂— | cyclo-C₅H₉ |
| 672. | 3-Furyl | H | trans —CH₂—CH=CH—CH₂— | cyclo-C₅H₉ |
| 673. | 2-Furyl | H | trans —CH₂—CH=CH—CH₂— | cyclo-C₅H₉ |
| 674. | 2-Pyrrolyl | H | trans —CH₂—CH=CH—CH₂— | cyclo-C₅H₉ |
| 675. | 2-Thienyl | H | trans —CH₂—CH=CH—CH₂— | cyclo-C₅H₉ |
| 676. | Pyridazin-2-yl | H | trans —CH₂—CH=CH—CH₂— | cyclo-C₅H₉ |
| 677. | 4-Methylthiazol-5-yl | H | trans —CH₂—CH=CH—CH₂— | cyclo-C₅H₉ |
| 678. | 2-Methyloxazol-4-yl | H | trans —CH₂—CH=CH—CH₂— | cyclo-C₅H₉ |
| 679. | Cyclopropyl | H | trans —CH₂—CH=CH—CH₂— | cyclo-C₅H₉ |
| 680. | Cyclobutyl | H | trans —CH₂—CH=CH—CH₂— | cyclo-C₅H₉ |
| 681. | Cyclopentyl | H | trans —CH₂—CH=CH—CH₂— | cyclo-C₅H₉ |
| 682. | Cyclohexyl | H | trans —CH₂—CH=CH—CH₂— | cyclo-C₅H₉ |
| 683. | H₃C—O—CH₂ | H | trans —CH₂—CH=CH—CH₂— | cyclo-C₅H₉ |
| 684. | Oxan-4-yl | H | trans —CH₂—CH=CH—CH₂— | cyclo-C₅H₉ |
| 685. | 1-Methylpiperidin-4-yl | H | trans —CH₂—CH=CH—CH₂— | cyclo-C₅H₉ |
| 686. | OH | H | —(CH₂)₄— | cyclo-C₃H₅ |
| 687. | OH | CH₃ | —(CH₂)₄— | cyclo-C₃H₅ |
| 688. | CH₃ | H | —(CH₂)₄— | cyclo-C₃H₅ |
| 689. | C(CH₃)₃ | H | —(CH₂)₄— | cyclo-C₃H₅ |
| 690. | C₆H₅ | H | —(CH₂)₄— | cyclo-C₃H₅ |
| 691. | C₆H₅ | CH₃ | —(CH₂)₄— | cyclo-C₃H₅ |
| 692. | CF₃ | H | —(CH₂)₄— | cyclo-C₃H₅ |
| 693. | OH | F | —(CH₂)₄— | cyclo-C₃H₅ |
| 694. | OH | CN | —(CH₂)₄— | cyclo-C₃H₅ |
| 695. | N(CH₃)₂ | H | —(CH₂)₄— | cyclo-C₃H₅ |
| 696. | N(CH₃)₂ | CH₃ | —(CH₂)₄— | cyclo-C₃H₅ |
| 697. | OH | H | trans —CH₂—CH=CH—CH₂— | cyclo-C₃H₅ |
| 698. | OH | CH₃ | trans —CH₂—CH=CH—CH₂— | cyclo-C₃H₅ |
| 699. | CH₃ | H | trans —CH₂—CH=CH—CH₂— | cyclo-C₃H₅ |
| 700. | C(CH₃)₃ | H | trans —CH₂—CH=CH—CH₂— | cyclo-C₃H₅ |
| 701. | C₆H₅ | H | trans —CH₂—CH=CH—CH₂— | cyclo-C₃H₅ |
| 702. | C₆H₅ | CH₃ | trans —CH₂—CH=CH—CH₂— | cyclo-C₃H₅ |
| 703. | CF₃ | H | trans —CH₂—CH=CH—CH₂— | cyclo-C₃H₅ |
| 704. | OH | F | trans —CH₂—CH=CH—CH₂— | cyclo-C₃H₅ |
| 705. | OH | CN | trans —CH₂—CH=CH—CH₂— | cyclo-C₃H₅ |
| 706. | N(CH₃)₂ | H | trans —CH₂—CH=CH—CH₂— | cyclo-C₃H₅ |
| 707. | N(CH₃)₂ | CH₃ | trans —CH₂—CH=CH—CH₂— | cyclo-C₃H₅ |
| 708. | OH | H | trans —CH₂—C(CH₃)=CH—CH₂— | cyclo-C₃H₅ |
| 709. | OH | CH₃ | trans —CH₂—C(CH₃)=CH—CH₂— | cyclo-C₃H₅ |
| 710. | CH₃ | H | trans —CH₂—C(CH₃)=CH—CH₂— | cyclo-C₃H₅ |
| 711. | C(CH₃)₃ | H | trans —CH₂—C(CH₃)=CH—CH₂— | cyclo-C₃H₅ |
| 712. | C₆H₅ | H | trans —CH₂—C(CH₃)=CH—CH₂— | cyclo-C₃H₅ |
| 713. | C₆H₅ | CH₃ | trans —CH₂—C(CH₃)=CH—CH₂— | cyclo-C₃H₅ |
| 714. | CF₃ | H | trans —CH₂—C(CH₃)=CH—CH₂— | cyclo-C₃H₅ |
| 715. | OH | F | trans —CH₂—C(CH₃)=CH—CH₂— | cyclo-C₃H₅ |
| 716. | OH | CN | trans —CH₂—C(CH₃)=CH—CH₂— | cyclo-C₃H₅ |
| 717. | N(CH₃)₂ | H | trans —CH₂—C(CH₃)=CH—CH₂— | cyclo-C₃H₅ |

TABLE 1-continued

| | R¹ | R² | A' | Rᵃ |
|---|---|---|---|---|
| 718. | N(CH₃)₂ | CH₃ | trans —CH₂—C(CH₃)=CH—CH₂— | cyclo-C₃H₅ |
| 719. | OH | H | —CH₂—CH(CH₃)—CH₂—CH₂— | cyclo-C₃H₅ |
| 720. | OH | CH₃ | —CH₂—CH(CH₃)—CH₂—CH₂— | cyclo-C₃H₅ |
| 721. | CH₃ | H | —CH₂—CH(CH₃)—CH₂—CH₂— | cyclo-C₃H₅ |
| 722. | C(CH₃)₃ | H | —CH₂—CH(CH₃)—CH₂—CH₂— | cyclo-C₃H₅ |
| 723. | C₆H₅ | H | —CH₂—CH(CH₃)—CH₂—CH₂— | cyclo-C₃H₅ |
| 724. | C₆H₅ | CH₃ | —CH₂—CH(CH₃)—CH₂—CH₂— | cyclo-C₃H₅ |
| 725. | CF₃ | H | —CH₂—CH(CH₃)—CH₂—CH₂— | cyclo-C₃H₅ |
| 726. | OH | F | —CH₂—CH(CH₃)—CH₂—CH₂— | cyclo-C₃H₅ |
| 727. | OH | CN | —CH₂—CH(CH₃)—CH₂—CH₂— | cyclo-C₃H₅ |
| 728. | N(CH₃)₂ | H | —CH₂—CH(CH₃)—CH₂—CH₂— | cyclo-C₃H₅ |
| 729. | N(CH₃)₂ | CH₃ | —CH₂—CH(CH₃)—CH₂—CH₂— | cyclo-C₃H₅ |
| 730. | OH | H | —CH₂—CH₂—CH₂—CH(CH₃)— | cyclo-C₃H₅ |
| 731. | OH | CH₃ | —CH₂—CH₂—CH₂—CH(CH₃)— | cyclo-C₃H₅ |
| 732. | CH₃ | H | —CH₂—CH₂—CH₂—CH(CH₃)— | cyclo-C₃H₅ |
| 733. | C(CH₃)₃ | H | —CH₂—CH₂—CH₂—CH(CH₃)— | cyclo-C₃H₅ |
| 734. | C₆H₅ | H | —CH₂—CH₂—CH₂—CH(CH₃)— | cyclo-C₃H₅ |
| 735. | C₆H₅ | CH₃ | —CH₂—CH₂—CH₂—CH(CH₃)— | cyclo-C₃H₅ |
| 736. | CF₃ | H | —CH₂—CH₂—CH₂—CH(CH₃)— | cyclo-C₃H₅ |
| 737. | OH | F | —CH₂—CH₂—CH₂—CH(CH₃)— | cyclo-C₃H₅ |
| 738. | OH | CN | —CH₂—CH₂—CH₂—CH(CH₃)— | cyclo-C₃H₅ |
| 739. | N(CH₃)₂ | H | —CH₂—CH₂—CH₂—CH(CH₃)— | cyclo-C₃H₅ |
| 740. | N(CH₃)₂ | CH₃ | —CH₂—CH₂—CH₂—CH(CH₃)— | cyclo-C₃H₅ |
| 741. | 1-Methylpyrrol-2-yl | H | —(CH₂)₄— | cyclo-C₃H₅ |
| 742. | 3-Pyridyl | H | —(CH₂)₄— | cyclo-C₃H₅ |
| 743. | 3-Thienyl | H | —(CH₂)₄— | cyclo-C₃H₅ |
| 744. | 4-Fluorophenyl | H | —(CH₂)₄— | cyclo-C₃H₅ |
| 745. | 4-Pyridyl | H | —(CH₂)₄— | cyclo-C₃H₅ |
| 746. | 3-Furyl | H | —(CH₂)₄— | cyclo-C₃H₅ |
| 747. | 2-Furyl | H | —(CH₂)₄— | cyclo-C₃H₅ |
| 748. | 2-Pyrrolyl | H | —(CH₂)₄— | cyclo-C₃H₅ |
| 749. | 2-Thienyl | H | —(CH₂)₄— | cyclo-C₃H₅ |
| 750. | Pyridazin-2-yl | H | —(CH₂)₄— | cyclo-C₃H₅ |
| 751. | 4-Methylthiazol-5-yl | H | —(CH₂)₄— | cyclo-C₃H₅ |
| 752. | 2-Methyloxazol-4-yl | H | —(CH₂)₄— | cyclo-C₃H₅ |
| 753. | Cyclopropyl | H | —(CH₂)₄— | cyclo-C₃H₅ |
| 754. | Cyclobutyl | H | —(CH₂)₄— | cyclo-C₃H₅ |
| 755. | Cyclopentyl | H | —(CH₂)₄— | cyclo-C₃H₅ |
| 756. | Cyclohexyl | H | —(CH₂)₄— | cyclo-C₃H₅ |
| 757. | H₃C—O—CH₂ | H | —(CH₂)₄— | cyclo-C₃H₅ |
| 758. | Oxan-4-yl | H | —(CH₂)₄— | cyclo-C₃H₅ |
| 759. | 1-Methylpiperidin-4-yl | H | —(CH₂)₄— | cyclo-C₃H₅ |
| 760. | 1-Methylpyrrol-2-yl | H | trans —CH₂—CH=CH—CH₂— | cyclo-C₃H₅ |
| 761. | 3-Pyridyl | H | trans —CH₂—CH=CH—CH₂— | cyclo-C₃H₅ |
| 762. | 3-Thienyl | H | trans —CH₂—CH=CH—CH₂— | cyclo-C₃H₅ |
| 763. | 4-Fluorophenyl | H | trans —CH₂—CH=CH—CH₂— | cyclo-C₃H₅ |
| 764. | 4-Pyridyl | H | trans —CH₂—CH=CH—CH₂— | cyclo-C₃H₅ |
| 765. | 3-Furyl | H | trans —CH₂—CH=CH—CH₂— | cyclo-C₃H₅ |
| 766. | 2-Furyl | H | trans —CH₂—CH=CH—CH₂— | cyclo-C₃H₅ |
| 767. | 2-Pyrrolyl | H | trans —CH₂—CH=CH—CH₂— | cyclo-C₃H₅ |
| 768. | 2-Thienyl | H | trans —CH₂—CH=CH—CH₂— | cyclo-C₃H₅ |
| 769. | Pyridazin-2-yl | H | trans —CH₂—CH=CH—CH₂— | cyclo-C₃H₅ |
| 770. | 4-Methylthiazol-5-yl | H | trans —CH₂—CH=CH—CH₂— | cyclo-C₃H₅ |
| 771. | 2-Methyloxazol-4-yl | H | trans —CH₂—CH=CH—CH₂— | cyclo-C₃H₅ |
| 772. | Cyclopropyl | H | trans —CH₂—CH=CH—CH₂— | cyclo-C₃H₅ |
| 773. | Cyclobutyl | H | trans —CH₂—CH=CH—CH₂— | cyclo-C₃H₅ |
| 774. | Cyclopentyl | H | trans —CH₂—CH=CH—CH₂— | cyclo-C₃H₅ |
| 775. | Cyclohexyl | H | trans —CH₂—CH=CH—CH₂— | cyclo-C₃H₅ |
| 776. | H₃C—O—CH₂ | H | trans —CH₂—CH=CH—CH₂— | cyclo-C₃H₅ |
| 777. | Oxan-4-yl | H | trans —CH₂—CH=CH—CH₂— | cyclo-C₃H₅ |
| 778. | 1-Methylpiperidin-4-yl | H | trans —CH₂—CH=CH—CH₂— | cyclo-C₃H₅ |
| 779. | OH | H | —(CH₂)₄— | cyclo-C₄H₇ |
| 780. | OH | CH₃ | —(CH₂)₄— | cyclo-C₄H₇ |
| 781. | CH₃ | H | —(CH₂)₄— | cyclo-C₄H₇ |
| 782. | C(CH₃)₃ | H | —(CH₂)₄— | cyclo-C₄H₇ |
| 783. | C₆H₅ | H | —(CH₂)₄— | cyclo-C₄H₇ |
| 784. | C₆H₅ | CH₃ | —(CH₂)₄— | cyclo-C₄H₇ |
| 785. | CF₃ | H | —(CH₂)₄— | cyclo-C₄H₇ |
| 786. | OH | F | —(CH₂)₄— | cyclo-C₄H₇ |
| 787. | OH | CN | —(CH₂)₄— | cyclo-C₄H₇ |
| 788. | N(CH₃)₂ | H | —(CH₂)₄— | cyclo-C₄H₇ |
| 789. | N(CH₃)₂ | CH₃ | —(CH₂)₄— | cyclo-C₄H₇ |
| 790. | OH | H | trans —CH₂—CH=CH—CH₂— | cyclo-C₄H₇ |
| 791. | OH | CH₃ | trans —CH₂—CH=CH—CH₂— | cyclo-C₄H₇ |
| 792. | CH₃ | H | trans —CH₂—CH=CH—CH₂— | cyclo-C₄H₇ |
| 793. | C(CH₃)₃ | H | trans —CH₂—CH=CH—CH₂— | cyclo-C₄H₇ |
| 794. | C₆H₅ | H | trans —CH₂—CH=CH—CH₂— | cyclo-C₄H₇ |
| 795. | C₆H₅ | CH₃ | trans —CH₂—CH=CH—CH₂— | cyclo-C₄H₇ |

TABLE 1-continued

| | R¹ | R² | A' | Rᵃ |
|---|---|---|---|---|
| 796. | CF₃ | H | trans —CH₂—CH=CH—CH₂— | cyclo-C₄H₇ |
| 797. | OH | F | trans —CH₂—CH=CH—CH₂— | cyclo-C₄H₇ |
| 798. | OH | CN | trans —CH₂—CH=CH—CH₂— | cyclo-C₄H₇ |
| 799. | N(CH₃)₂ | H | trans —CH₂—CH=CH—CH₂— | cyclo-C₄H₇ |
| 800. | N(CH₃)₂ | CH₃ | trans —CH₂—CH=CH—CH₂— | cyclo-C₄H₇ |
| 801. | OH | H | trans —CH₂—C(CH₃)=CH—CH₂— | cyclo-C₄H₇ |
| 802. | OH | CH₃ | trans —CH₂—C(CH₃)=CH—CH₂— | cyclo-C₄H₇ |
| 803. | CH₃ | H | trans —CH₂—C(CH₃)=CH—CH₂— | cyclo-C₄H₇ |
| 804. | C(CH₃)₃ | H | trans —CH₂—C(CH₃)=CH—CH₂— | cyclo-C₄H₇ |
| 805. | C₆H₅ | H | trans —CH₂—C(CH₃)=CH—CH₂— | cyclo-C₄H₇ |
| 806. | C₆H₅ | CH₃ | trans —CH₂—C(CH₃)=CH—CH₂— | cyclo-C₄H₇ |
| 807. | CF₃ | H | trans —CH₂—C(CH₃)=CH—CH₂— | cyclo-C₄H₇ |
| 808. | OH | F | trans —CH₂—C(CH₃)=CH—CH₂— | cyclo-C₄H₇ |
| 809. | OH | CN | trans —CH₂—C(CH₃)=CH—CH₂— | cyclo-C₄H₇ |
| 810. | N(CH₃)₂ | H | trans —CH₂—C(CH₃)=CH—CH₂— | cyclo-C₄H₇ |
| 811. | N(CH₃)₂ | CH₃ | trans —CH₂—C(CH₃)=CH—CH₂— | cyclo-C₄H₇ |
| 812. | OH | H | —CH₂—CH(CH₃)—CH₂—CH₂— | cyclo-C₄H₇ |
| 813. | OH | CH₃ | —CH₂—CH(CH₃)—CH₂—CH₂— | cyclo-C₄H₇ |
| 814. | CH₃ | H | —CH₂—CH(CH₃)—CH₂—CH₂— | cyclo-C₄H₇ |
| 815. | C(CH₃)₃ | H | —CH₂—CH(CH₃)—CH₂—CH₂— | cyclo-C₄H₇ |
| 816. | C₆H₅ | H | —CH₂—CH(CH₃)—CH₂—CH₂— | cyclo-C₄H₇ |
| 817. | C₆H₅ | CH₃ | —CH₂—CH(CH₃)—CH₂—CH₂— | cyclo-C₄H₇ |
| 818. | CF₃ | H | —CH₂—CH(CH₃)—CH₂—CH₂— | cyclo-C₄H₇ |
| 819. | OH | F | —CH₂—CH(CH₃)—CH₂—CH₂— | cyclo-C₄H₇ |
| 820. | OH | CN | —CH₂—CH(CH₃)—CH₂—CH₂— | cyclo-C₄H₇ |
| 821. | N(CH₃)₂ | H | —CH₂—CH(CH₃)—CH₂—CH₂— | cyclo-C₄H₇ |
| 822. | N(CH₃)₂ | CH₃ | —CH₂—CH(CH₃)—CH₂—CH₂— | cyclo-C₄H₇ |
| 823. | OH | H | —CH₂—CH₂—CH₂—CH(CH₃)— | cyclo-C₄H₇ |
| 824. | OH | CH₃ | —CH₂—CH₂—CH₂—CH(CH₃)— | cyclo-C₄H₇ |
| 825. | CH₃ | H | —CH₂—CH₂—CH₂—CH(CH₃)— | cyclo-C₄H₇ |
| 826. | C(CH₃)₃ | H | —CH₂—CH₂—CH₂—CH(CH₃)— | cyclo-C₄H₇ |
| 827. | C₆H₅ | H | —CH₂—CH₂—CH₂—CH(CH₃)— | cyclo-C₄H₇ |
| 828. | C₆H₅ | CH₃ | —CH₂—CH₂—CH₂—CH(CH₃)— | cyclo-C₄H₇ |
| 829. | CF₃ | H | —CH₂—CH₂—CH₂—CH(CH₃)— | cyclo-C₄H₇ |
| 830. | OH | F | —CH₂—CH₂—CH₂—CH(CH₃)— | cyclo-C₄H₇ |
| 831. | OH | CN | —CH₂—CH₂—CH₂—CH(CH₃)— | cyclo-C₄H₇ |
| 832. | N(CH₃)₂ | H | —CH₂—CH₂—CH₂—CH(CH₃)— | cyclo-C₄H₇ |
| 833. | N(CH₃)₂ | CH₃ | —CH₂—CH₂—CH₂—CH(CH₃)— | cyclo-C₄H₇ |
| 834. | 1-Methylpyrrol-2-yl | H | —(CH₂)₄— | cyclo-C₄H₇ |
| 835. | 3-Pyridyl | H | —(CH₂)₄— | cyclo-C₄H₇ |
| 836. | 3-Thienyl | H | —(CH₂)₄— | cyclo-C₄H₇ |
| 837. | 4-Fluorophenyl | H | —(CH₂)₄— | cyclo-C₄H₇ |
| 838. | 4-Pyridyl | H | —(CH₂)₄— | cyclo-C₄H₇ |
| 839. | 3-Furyl | H | —(CH₂)₄— | cyclo-C₄H₇ |
| 840. | 2-Furyl | H | —(CH₂)₄— | cyclo-C₄H₇ |
| 841. | 2-Pyrrolyl | H | —(CH₂)₄— | cyclo-C₄H₇ |
| 842. | 2-Thienyl | H | —(CH₂)₄— | cyclo-C₄H₇ |
| 843. | Pyridazin-2-yl | H | —(CH₂)₄— | cyclo-C₄H₇ |
| 844. | 4-Methylthiazol-5-yl | H | —(CH₂)₄— | cyclo-C₄H₇ |
| 845. | 2-Methyloxazol-4-yl | H | —(CH₂)₄— | cyclo-C₄H₇ |
| 846. | Cyclopropyl | H | —(CH₂)₄— | cyclo-C₄H₇ |
| 847. | Cyclobutyl | H | —(CH₂)₄— | cyclo-C₄H₇ |
| 848. | Cyclopentyl | H | —(CH₂)₄— | cyclo-C₄H₇ |
| 849. | Cyclohexyl | H | —(CH₂)₄— | cyclo-C₄H₇ |
| 850. | H₃C—O—CH₂ | H | —(CH₂)₄— | cyclo-C₄H₇ |
| 851. | Oxan-4-yl | H | —(CH₂)₄— | cyclo-C₄H₇ |
| 852. | 1-Methylpiperidin-4-yl | H | —(CH₂)₄— | cyclo-C₄H₇ |
| 853. | 1-Methylpyrrol-2-yl | H | trans —CH₂—CH=CH—CH₂— | cyclo-C₄H₇ |
| 854. | 3-Pyridyl | H | trans —CH₂—CH=CH—CH₂— | cyclo-C₄H₇ |
| 855. | 3-Thienyl | H | trans —CH₂—CH=CH—CH₂— | cyclo-C₄H₇ |
| 856. | 4-Fluorophenyl | H | trans —CH₂—CH=CH—CH₂— | cyclo-C₄H₇ |
| 857. | 4-Pyridyl | H | trans —CH₂—CH=CH—CH₂— | cyclo-C₄H₇ |
| 858. | 3-Furyl | H | trans —CH₂—CH=CH—CH₂— | cyclo-C₄H₇ |
| 859. | 2-Furyl | H | trans —CH₂—CH=CH—CH₂— | cyclo-C₄H₇ |
| 860. | 2-Pyrrolyl | H | trans —CH₂—CH=CH—CH₂— | cyclo-C₄H₇ |
| 861. | 2-Thienyl | H | trans —CH₂—CH=CH—CH₂— | cyclo-C₄H₇ |
| 862. | Pyridazin-2-yl | H | trans —CH₂—CH=CH—CH₂— | cyclo-C₄H₇ |
| 863. | 4-Methylthiazol-5-yl | H | trans —CH₂—CH=CH—CH₂— | cyclo-C₄H₇ |
| 864. | 2-Methyloxazol-4-yl | H | trans —CH₂—CH=CH—CH₂— | cyclo-C₄H₇ |
| 865. | Cyclopropyl | H | trans —CH₂—CH=CH—CH₂— | cyclo-C₄H₇ |
| 866. | Cyclobutyl | H | trans —CH₂—CH=CH—CH₂— | cyclo-C₄H₇ |
| 867. | Cyclopentyl | H | trans —CH₂—CH=CH—CH₂— | cyclo-C₄H₇ |
| 868. | Cyclohexyl | H | trans —CH₂—CH=CH—CH₂— | cyclo-C₄H₇ |
| 869. | H₃C—O—CH₂ | H | trans —CH₂—CH=CH—CH₂— | cyclo-C₄H₇ |
| 870. | Oxan-4-yl | H | trans —CH₂—CH=CH—CH₂— | cyclo-C₄H₇ |
| 871. | 1-Methylpiperidin-4-yl | H | trans —CH₂—CH=CH—CH₂— | cyclo-C₄H₇ |

Examples of further compounds of the general formula I.1 are the compounds of the general formula I.1b,

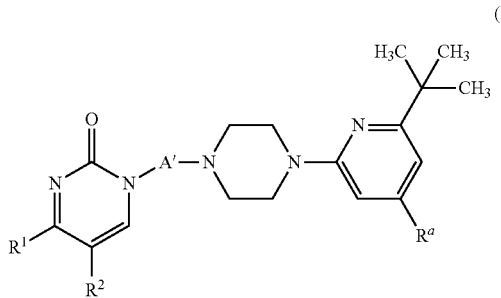
(I.1b)

in which A', $R^a$, $R^1$ and $R^2$ have the meanings indicated above, in particular the meanings indicated as preferred. Examples of such compounds are the compounds I.1b.1 to I.1b.871 where the variables A', $R^a$, $R^1$ and $R^2$ in each case jointly have the meaning indicated in one of lines 1 to 647 of Table 1.

Examples of further compounds of the general formula I.1 are the compounds of the general formula I.1c,

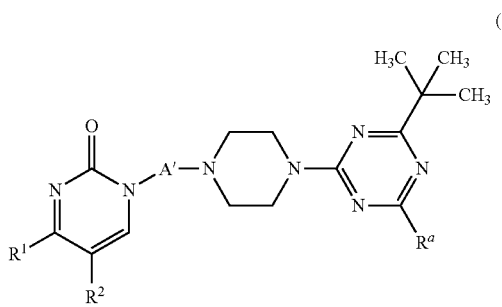
(I.1c)

in which A', $R^a$, $R^1$ and $R^2$ have the meanings indicated above, in particular the meanings indicated as preferred. Examples of such compounds are the compounds I.1c.1 to I.1c.871 where the variables A', $R^a$, $R^1$ and $R^2$ in each case jointly have the meaning indicated in one of lines 1 to 871 of Table 1.

Examples of further compounds of the general formula I.1 are the compounds of the general formula I.1d,

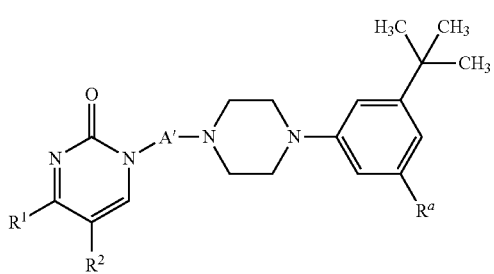
(I.1d)

in which A', $R^a$, $R^1$ and $R^2$ have the meanings indicated above, in particular the meanings indicated as preferred. Examples of such compounds are the compounds I.1d.1 to I.1d.871 where the variables A', $R^a$, $R^1$ and $R^2$ in each case jointly have the meaning indicated in one of lines 1 to 871 of Table 1.

Examples of further compounds of the general formula I.1 are the compounds of the general formula I.1e,

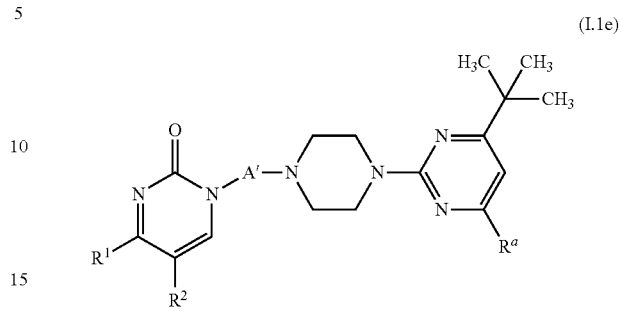
(I.1e)

in which A', $R^a$, $R^1$ and $R^2$ have the meanings indicated above, in particular the meanings indicated as preferred. Examples of such compounds are the compounds I.1e.1 to I.1e.871 where the variables A', $R^a$, $R^1$ and $R^2$ in each case jointly have the meaning indicated in one of lines 1 to 871 of Table 1.

Examples of further compounds of the general formula I.1 are the compounds of the general formula I.1f,

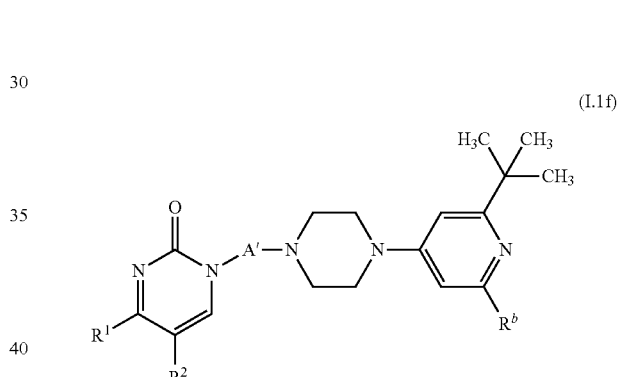
(I.1f)

in which A', $R^a$, $R^1$ and $R^2$ have the meanings indicated above, in particular the meanings indicated as preferred. Examples of such compounds are the compounds I.1f.1 to I.1f.871 where the variables A', $R^a$, $R^1$ and $R^2$ in each case jointly have the meaning indicated in one of lines 1 to 871 of Table 1.

Preparation of the compounds of the invention takes place in analogy to methods known from the literature. An important approach to the compounds of the invention is depicted in Scheme 1.

Scheme 1:

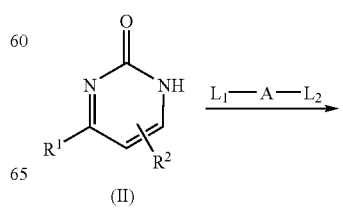
(II)

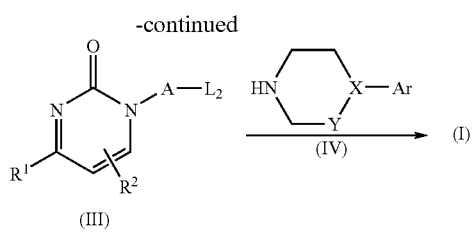

In Scheme 1, $R^1$, $R^2$, A, X, Y and Ar have the aforementioned meanings. $L_1$ and $L_2$ are leaving groups which can be displaced nucleophilically. Examples of suitable leaving groups which can be displaced nucleophilically are halogen, especially chlorine, bromine or iodine, alkyl- and arylsulfonate such as mesylate, tosylate. $L_1$ and $L_2$ are preferably different from one another and differ in reactivity. For example, $L_1$ is bromine or iodine and $L_2$ is chlorine. The reaction conditions necessary for the reaction correspond to the reaction conditions usual for nucleophilic substitutions.

Compounds of the general formula IV are either known from the literature, e.g. disclosed in WO 96/02519, WO 97/25324, WO 99/02503 or the literature cited in these publications, or can be prepared by the processes described therein.

The pyrimidinone compounds of the formulae II are known and in some cases commercially available or can be prepared by known processes for pyrimidinone synthesis as described, for example, in Austr. J. Chem. 1968, 221, pp. 243-255; J. Med. Chem. 1978, 21, pp. 623-628; Tetrahedron Lett. 1986, 27, pp. 2611-2612; Chemiker Ztg. 1977, 6, p. 305. The compounds II can also be prepared by the methods indicated in Scheme 4.

It is additionally possible for compounds of the formula II, where $R^1$ is optionally substituted alkenyl, optionally substituted phenyl or optionally substituted C-bonded heteroaryl, to be prepared by Suzuki coupling via the route shown in Scheme 2.

Scheme 2:

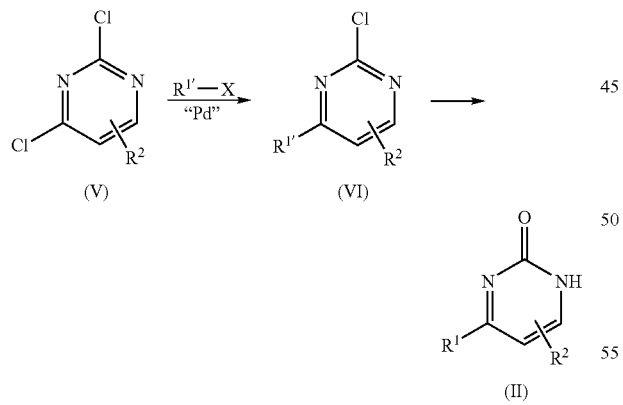

In Scheme 2, $R^1$ is optionally substituted alkenyl, optionally substituted phenyl or optionally substituted C-bonded heteroaryl. X is a group $B(OH)_2$, $B(OR)_2$ or the radical $(BO)_3/3$ derived from the corresponding boronic anhydride. "Pd" is a palladium(0) complex which preferably has 4 trialkylphosphine or triarylphosphine ligands. $R^2$ has the meanings indicated above and is in particular hydrogen or $C_1$-$C_4$-alkyl.

Coupling of V with the compound $R^{1'}$—X takes place under the conditions of a Suzuki coupling (for review, see A. Suzuki et al. in Chem. Rev. 1995, 95, pp. 2457-2483). The reaction conditions necessary for Suzuki coupling of 2,4-dichloropyrimidines V with $R^{1'}$—X are known from the literature, e.g. from J. Org. Chem. 66(21) (2001), pp. 7124-7128. The 2-chloropyrimidine VI obtained in this case can be converted into the corresponding 2-pyrimidinone II in a manner known per se, e.g. under the conditions indicated in Acta Chem. Scand. B, 1984, 38, pp. 505-508.

A further possibility for preparing the compounds of the formula II in which $R^1$ is optionally substituted $C_1$-$C_6$-alkyl or $C_3$-$C_6$-cycloalkyl, in particular ethyl, isopropyl, cyclopropyl, cyclobutyl, cyclohexyl, and $R^2$ is H, is for example by the process shown in Scheme 3.

Scheme 3:

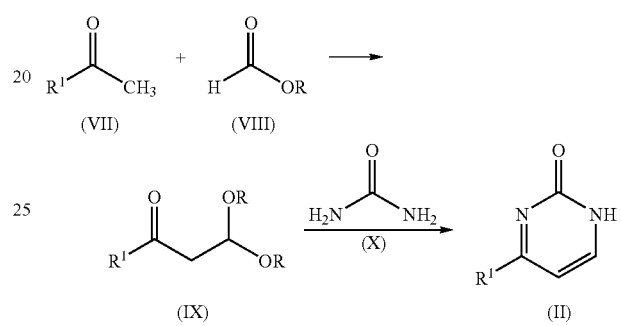

In Scheme 3, R is, for example, $C_1$-$C_4$-alkyl. In Scheme 3 there is initial conversion of a ketone VII with a formic ester VIII, e.g. methyl formate, in a manner known per se into the ketal IX (see Helv. Chim. Acta 2002, 85, 2926-2929, Ex. 6). The reaction is normally carried out in the presence of a base such as an alcoholate in an inert solvent such as an ether. Reaction of the resulting ketal IX with urea X to form the corresponding 2-pyrimidinone II takes place under conditions known from the literature, e.g. as described in Aust. J. Chem. 1968, 21, 243-55 (in particular page 252).

The 2-pyrimidinones II in which $R^1$ is hydrogen and $R^2$ is optionally substituted phenyl can be prepared for example by the process shown in Scheme 4.

Scheme 4:

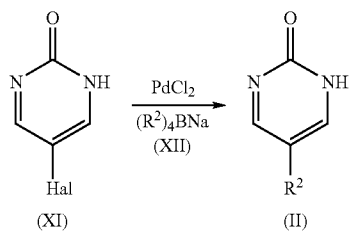

In Scheme 4, Hal is halogen, in particular bromine or chlorine. Coupling of the halopyrimidinone XI with the borate XII takes place under Suzuki conditions (see Tetrahedron 1997, 53, 14437-50). The modified Suzuki cross-coupling between the pyridinone XI and the borate XII normally takes place in aqueous solvents in the presence of a phosphine-free Pd catalyst such as palladium(II) chloride and in the presence of a base. Examples of suitable bases are alkali metal hydroxides such as sodium hydroxide. The pyridinones XI and the borates XII are known from the literature.

The pyrimidinone compounds I of the invention, in which $R^1$ is SH, can be prepared for example by the process shown in Scheme 5.

Scheme 5:

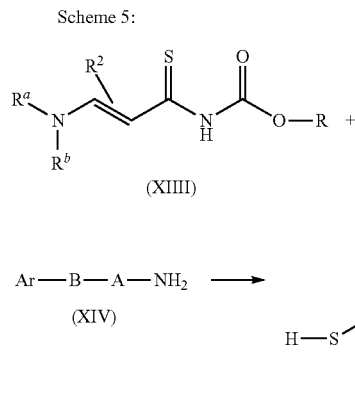

(XIIII)

Ar—B—A—NH$_2$ (XIV)

{I: $R^1$ = SH}

In Scheme 5, $R^a$ and $R^b$ are for example both $C_1$-$C_4$-alkyl or form with the nitrogen atom to which they are bonded a saturated ring, e.g. a piperidinyl, piperazinyl, pyrrolidinyl or morpholinyl radical. R is, for example, $C_1$-$C_4$-alkyl. The reaction shown in Scheme 5 is known in principle, for example from J. Hetercycl. Chem. 5 (1968) pp. 837-844 or from WO 00/61579, and can be employed in an analogous manner for preparing the compounds I of the invention. The same applies to the starting compounds XIII. The compounds of the formula XIV are known for example from the prior art cited at the outset or can be prepared in a manner known per se from the corresponding halogen compound Ar—B-A-Hal in which Hal is chlorine, bromine or iodine. For example, the amine XIV Ar—B-A-Hal can be prepared by conversion into the corresponding azide Ar—B-A-$N_3$ and subsequent reduction to the amine. The conditions necessary for this are known to the skilled worker, e.g. from Chem. Rev. 1994, 94, p. 1, and can be applied analogously to the preparation of XIV. The halogen compounds Ar—B-A-Hal are disclosed for example in WO 96/02519, WO 97/25324, WO 99/09015, WO 99/02503 or can be prepared in analogy to the processes described therein.

The thiol group in compounds I with $R^1$=SH can be converted into other radicals $R^1$ by standard processes of organic chemistry. An overview is given in Scheme 6.

Scheme 6:

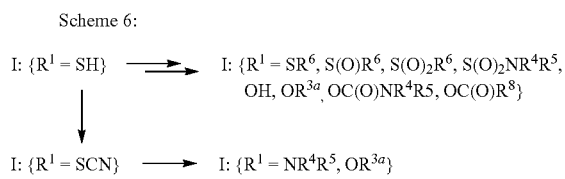

Processes for this purpose are known to the skilled worker and include conversion of SH into $SR^6$ by alkylation, oxidation of $SR^6$ to the corresponding $SOR^6$ and $SO_2R^6$ groups, oxidative degradation of SH to OH with, where appropriate, subsequent alkylation or esterification to give the groups $OR^{3a}$, $OC(O)NR^4R^5$ or $OC(O)R^8$.

The pyrimidinone compounds I.1 of the invention, in which $R^1$ is $NR^4R^5$, can be prepared for example by the process shown in Scheme 7.

Scheme 7:

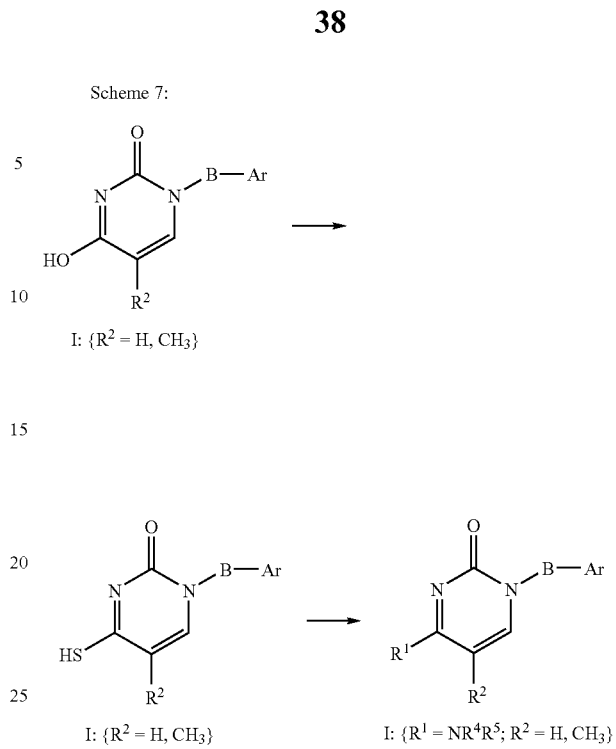

I: {$R^2$ = H, CH$_3$}

I: {$R^2$ = H, CH$_3$}

I: {$R^1$ = $NR^4R^5$; $R^2$ = H, CH$_3$}

In Scheme 7, B and Ar have the aforementioned meanings. As shown in Scheme 7, initially compound I in which $R^1$ is OH is converted into the corresponding thiol I with $R^1$=SH. Examples of suitable sulfurizing agents are organophosphorus sulfides such as Lawesson's reagent, organotin sulfides or phosphorus(V) sulfide. A preferred sulfurizing agent is phosphorus pentasulfide ($P_4S_{10}$). The conditions necessary for the thionation are known to the skilled worker, e.g. from J. Med. Chem. 1984, 27, 1470-80 (in particular page 1478, Example 8b). The thiol I with $R^1$=SH which is obtained in this way can then be converted by reaction with a compound of the formula $HNR^4R^5$ in which $R^4$ and $R^5$ have the aforementioned meanings into other compounds I with $R^1$=$NR^4R^5$. The reaction usually takes place in an inert solvent. The activation energy necessary for the reaction can be introduced into the reaction mixture by means of microwaves (for reaction with use of microwaves, see Tetrahedron 2001, 57, pp. 9199 et seq., pp. 9225 et seq. and in general "Microwaves in Organic Synthesis", André Loupy (Editor), Wiley-VCH 2002).

The pyrimidinone compounds II in which $R^1$ is $NR^4R^5$ can be prepared for example in analogy to above Scheme 7. The preparation is outlined in Scheme 8.

Scheme 8:

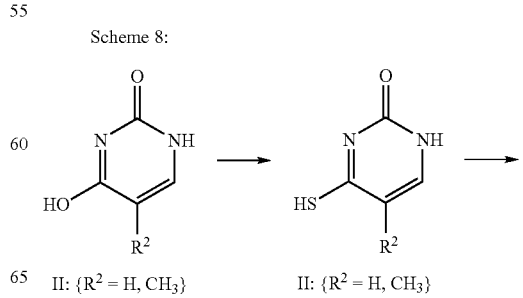

II: {$R^2$ = H, CH$_3$}

II: {$R^2$ = H, CH$_3$}

-continued

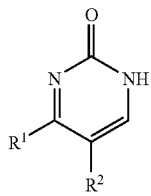

II: {R$^1$ = NR$^4$R$^5$; R$^2$ = H, CH$_3$}

Preparation of the tautomers Ia and Ib can take place in a manner analogous to the preparation of compound I described here. For example, the tautomers Ib can be prepared by the synthetic route shown in Scheme 1. In addition, the compound I can be converted into its tautomers Ia with Q=halogen by treating it with a suitable halogenating agent such as PCl$_3$ or POCl$_3$.

Unless indicated otherwise, the reactions described above generally take place in a solvent at temperatures between room temperature and the boiling point of the solvent used. Examples of solvents which can be used are ethers such as diethyl ether, diisopropyl ether, methyl tert-butyl ether or tetrahydrofuran, dimethylformamide, dimethyl sulfoxide, dimethoxyethane, toluene, xylene, acetonitrile, ketones such as acetone or methyl ethyl ketone, or alcohols such as methanol, ethanol or butanol.

A base is present if desired to neutralize the protons liberated in the reactions. Suitable bases include inorganic bases such as sodium or potassium carbonate, sodium or potassium bicarbonate, also alcoholates such as sodium methoxide, sodium ethoxide, alkali metal hydrides such as sodium hydride, organometallic compounds such as butyllithium or alkylmagnesium compounds, or organic nitrogen bases such as triethylamine or pyridine. The latter can simultaneously serve as solvents.

The crude product is isolated in a conventional way, for example by filtration, removal of the solvent by distillation or extraction from the reaction mixture etc. The resulting compounds can be purified in a conventional way, for example by recrystallization from a solvent, chromatography or conversion into an acid addition salt.

The acid addition salts are prepared in a conventional way by mixing the free base with the appropriate acid, where appropriate in solution in an organic solvent, for example a low molecular weight alcohol such as methanol, ethanol or propanol, an ether such as methyl t-butyl ether or diisopropyl ether, a ketone such as acetone or methyl ethyl ketone or an ester such as ethyl acetate.

The inventive compounds of the formula I are highly selective dopamine D$_3$ receptor ligands which, because of their low affinity for other receptors such as D, receptors, D$_4$ receptors, α1- and/or α2-adrenergic receptors, muscarinergic receptors, histaminic receptors, opiate receptors and, in particular, for dopamine D$_2$ receptors, have fewer side effects than classical neuroleptics which comprise D$_2$ receptor antagonists.

The high affinity of the inventive compounds for D$_3$ receptors is reflected in very low in vitro K$_i$ values of ordinarily less than 100 nM (nmol/l) and especially of less than 50 nM. Binding affinities for D$_3$ receptors can for example be determined via the displacement of [$^{125}$I]-iodosulpride in receptor-binding studies.

Particularly important according to the invention are compounds whose selectivity K$_i$(D$_2$)/K$_i$(D$_3$) is preferably at least 10, even better at least 30 and particularly advantageously at least 50. Receptor-binding studies on D$_1$, D$_2$ and D$_4$ receptors can be carried out for example via the displacement of [$^3$H]SCH23390, [$^{125}$I]iodosulpride and [$^{125}$I]spiperone.

The compounds of the invention additionally show lower inhibition of the mitochondrial respiratory chain, i.e. mitochondrial respiration is inhibited by the compounds I only at comparatively high plasma levels. Inhibition of mitochondrial respiration is observed with the compounds of the invention in vitro only at concentrations of >50 µM, frequently of >100 µM and specifically at concentrations of >200 µM (IC$_{50}$ values).

The compounds of the invention additionally show comparatively low plasma protein binding.

The compounds can, because of their binding profile, be used for the treatment of conditions which respond to dopamine D$_3$ ligands, i.e. they are effective for the treatment of those disorders or conditions where an influencing (modulation) of dopamine D$_3$ receptors leads to an improvement in the clinical condition or to cure of the disease. Examples of such conditions are disorders or conditions of the central nervous system.

Disorders or conditions of the central nervous system mean disorders affecting the spinal cord or, in particular, the brain. The term "disorder" in the sense according to the invention refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together where appropriate, to be combined into patterns, i.e. syndromes, which can be treated according to the invention.

The disorders which can be treated according to the invention include in particular psychiatric and neurological disorders. These comprise in particular organic disorders, symptomatic disorders included, such as psychoses of the acute exogenous type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated according to the invention also include parkinsonism and epilepsy and, in particular, the affective disorders associated therewith.

Addictive disorders include the psychological disorders and behavioral disorders caused by the abuse of psychotropic substances such as pharmaceuticals or drugs, and other addictive disorders such as, for example, compulsive gambling (impulse control disorders not elsewhere classified). Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol.

With a view to the treatment of addictive disorders, the inventive compounds of the formula I which are particularly preferred are those which themselves have no psychotropic effect. This can also be observed in a test on rats which reduce the self-administration of psychotropic substances, for example cocaine, after administration of compounds which can be used according to the invention.

According to a further aspect of the present invention, the inventive compounds are suitable for the treatment of disorders the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The conditions which can be treated with the inventive compounds are frequently characterized by a progressive development, i.e. the states described above change over the course of time, the severity usually increasing and, where appropriate, states possibly interchanging or other states being added to previously existing states.

The inventive compounds can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional lability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced associationability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like.

A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptom. It may take place short-term, be directed at the medium term or may also be a long-term treatment, for example as part of maintenance therapy.

The inventive compounds are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the inventive compounds are also for the treatment of renal function disorders, especially of renal function disorders caused by diabetes mellitus (see WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, where appropriate together or alternately with other active ingredients or active ingredient-containing products, so that an individual to be treated is given a daily dose preferably of about 0.1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer inhibitors of the invention. A further possibility is also to use liposomes or microspheres.

The compositions are produced by mixing or diluting inhibitors of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996.

The following examples serve to illustrate the invention without limiting it.

The nuclear magnetic resonance spectral properties (NMR) relate to chemical shifts (δ) expressed in parts per million (ppm). The relative area for the shifts in the $^1$H NMR spectrum corresponds to the number of hydrogen atoms for a particular functional type in the molecule. The nature of the shift in terms of multiplicity is indicated as singlet (s), broad singlet (s. br.), doublet (d), broad doublet (d br.), triplet (t), broad triplet (t br.), quartet (q), quintet (quint.), multiplet (m).

PREPARATION EXAMPLES

Example 1

1-(3-{4-[2-tert-Butyl-6-(trifluoromethyl)pyrimidin-4-yl]piperazin-1-yl}propyl)-4-mercapto-5-methylpyrimidin-2(1H)-one 1.1 4-[4-(3-Azidopropyl)piperazin-1-yl]-2-tert-butyl-6-(trifluoromethyl)pyrimidine 2.4 g (36.9 mmol) of sodium azide were added to 13.5 g (36.9 mmol) of 2-tert-butyl-4-[4-(3-chloropropyl)piperazin-1-yl]-6-(trifluoromethyl)pyrimidine (DE 197 35 410) in 60 ml of N,N-dimethylformamide (DMF), and the mixture was stirred at 70° C. for 3 hours. The reaction mixture was allowed to cool to room temperature, the mixture was poured into saturated brine, and the aqueous mixture was extracted with ethyl acetate. The organic phase was washed three times with an NaCl solution, dried over $Na_2SO_4$, filtered to remove the desiccant and concentrated in vacuo. Yield: 13.7 g.

ESI-MS: 373.1, [M+H$^+$]=372.1, 186.6;

1.2 3-{4-[2-tert-Butyl-6-(trifluoromethyl)pyrimidin-4-yl]piperazin-1-yl}propan-1-amine hydrochloride 13.7 g (36.89 mmol) of 4-[4-(3-azidopropyl)piperazin-1-yl]-2-tert-butyl-6-(trifluoromethyl)pyrimidine from Example 1.1 in 200 ml of methanol and 0.3 g of Pd/carbon (10%) were stirred under a hydrogen atmosphere at room temperature for 12 hours. The catalyst was filtered off through kieselghur, the resulting filtrate was filtered, and the clear solution was concentrated. The residue was dissolved in diethyl ether, and a solution of HCl in diethyl ether was added, whereupon a precipitate separated out. The hydrochloride was filtered off with suction, washed with diethyl ether and dried under nitrogen and then in vacuo at 40° C. Yield: 12.7 g.

$^1$H NMR (400 MHz, DMSO-d$_6$) δ (ppm): 11.62 (1H, s br.), 8.23 (1H, s. br.), 7.23 (1H, s.), 4.67 (1H, s. br.), 3.55 (3H, d br.), 3.32-2.88 (2+2+1H, m br.), 2.10 (1H, quint.), 1.30 (9H, s.).

1.3 1-(3-{4-[2-tert-Butyl-6-(trifluoromethyl)pyrimidin-4-yl]piperazin-1-yl}propyl)-4-mercapto-5-methylpyrimidin-2(1H)-one 0.7 g (2.7 mmol) of ethyl (2E)-2-methyl-3-piperidin-1-ylprop-2-enethioylcarbamate (WO 00/61579), 0.9 g (2.6 mmol) of 3-{4-[2-tert-butyl-6-(trifluoromethyl)pyrimidin-4-yl]piperazin-1-yl}propan-1-amine hydrochloride from Example 1.2 and 0.6 g (5.5 mmol) of N-methylmorpholine in 20 ml of methanol were stirred at room temperature under a nitrogen atmosphere for 12 hours. Insolubles were removed by filtration, washed three times with methanol and water and then recrystallized from ethyl acetate. Drying in vacuo at 50° C. resulted in 0.5 g of the title compound.

ESI-MS: 472.1, [M+H$^+$]=471.1, 236.1;

$^1$H NMR (360 MHz, DMSO-d$_6$) δ (ppm): 12.33 (1H, s.), 7.57 (1H, s.), 7.48 (1H, s.), 6.81 (1H, s.), 4.62 (2H, s br.), 3.98 (2H, t), 3.84 (2H, t br.), 3.65 (2H, d br.), 3.18 (2H, t br.), 2.36 (2H, quint.), 2.08 (3H, s), 1.33 (9H, s).

Example 2

1-(4-{4-[2-tert-Butyl-6-(trifluoromethyl)pyrimidin-4-yl]piperazin-1-yl}butyl)-4-mercapto-5-methylpyrimidin-2(1H)-one 0.7 g of the title compound was obtained in analogy to Example 1 from 1.2 g (3.3 mmol) of 4-{4-[2-tert-butyl-6-(trifluoromethyl)pyrimidin-4-yl]piperazin-1-yl}butan-1-amine.

ESI-MS: 486.4, [M+H$^+$]=485.4, 243.3;

$^1$H NMR (360 MHz, CDCl$_3$) δ (ppm: 10.33 (1H, s. br.), 7.00 (1H, s.), 6.57 (1H, s.), 3.60-3.80 (6H, m), 2.52 (4H, t), 2.44 (2H, t), 2.10 (3H, s), 1.78 (2H, quint.), 1.58 (2H, quint.), 1.33 (9H, s).

Example 3

1-{4-[4-(Benzylthio)-5-methyl-2-oxopyrimidin-1 (2H)-yl]butyl}-4-[2-tert-butyl-6-(trifluoromethyl) pyrimidin-4-yl]piperazin-1-ium chloride 145.4 mg (0.3 mmol) of 1-(4-{4-[2-tert-butyl-6-(trifluoromethyl)pyrimidin-4-yl]piperazin-1-yl}butyl)-4-mercapto-5-methylpyrimidin-2(1H)-one from Example 2 and 78.8 mg (0.6 mmol) of $K_2CO_3$ were stirred in 10 ml of N,N-dimethylformamide (DMF) for 20 minutes. Then 77.0 mg (0.5 mmol) of benzyl bromide were added dropwise. The reaction mixture was stirred at room temperature for 2 days and then added to water and extracted with ethyl acetate. Drying of the organic phase over $Na_2SO_4$, removal of the desiccant by filtration and concentration in vacuo were followed by stirring the resulting solid with diethyl ether and filtration with suction. The residue after concentration of the mother liquor in vacuo was taken up in a little $CH_2Cl_2$, and a solution of HCl in diethyl ether was added, whereupon the required product precipitated as hydrochloride. The hydrochloride was filtered off with suction and washed with diethyl ether, and the title compound was dried in vacuo at 40° C. Yield: 25 mg.

ESI-MS: [M+Na$^+$]=597.3, 576.2, [M+H$^+$]=575.2, 288.1.

$^1$H NMR (500 MHz, DMSO-d$_6$) δ (ppm: 10.72 (1H, s. br.), 7.85 (1H, s.), 7.40 (2H, d), 7.30 (2H, t), 7.24 (1H, t), 7.21 (1H, s.), 4.38 (2H, s.), 3.79 (2H, m), 3.55 (2H, d br.), 3.51-3.40 (2H, m br.), 3.15-3.00 (4H, m), 1.93 (3H, s.), 1.70 (4H, s. br.), 1.31 (9H, s.).

Example 4

1-[2-tert-Butyl-6-(trifluoromethyl)pyrimidin-4-yl]-4-{4-[5-methyl-4-(methylthio)-2-oxopyrimidin-1 (2H)-yl]butyl}piperazin-4-ium chloride 96.9 mg (0.8 mmol) of ethyldiisopropylamine (DIPEA) were added to 145.4 mg (0.3 mmol) of 1-(4-{4-[2-tert-butyl-6-(trifluoromethyl)pyrimidin-4-yl]piperazin-1-yl}butyl)-4-mercapto-5-methylpyrimidin-2(1H-one from Example 2 in 12 ml of methanol under nitrogen, and the reaction mixture was stirred for 20 minutes. Then 183.1 mg (1.3 mmol) of methyl iodide were added dropwise, and the reaction mixture was stirred at room temperature for 12 hours. Water was added to the reaction mixture, and the aqueous mixture was extracted twice with ethyl acetate. The residue after drying of the organic phase over $Na_2SO_4$, removal of the desiccant by filtration and evaporation of the solvent to dryness in vacuo was taken up in diethyl ether. A solution of HCl in diethyl ether was added, whereupon the required product precipitated as hydrochloride. The hydrochloride was filtered off with suction and washed with diethyl ether, and the title compound was dried in vacuo at 40° C. Yield: 85.0 mg.

ESI-MS: [M+Na$^+$]=521.3, 500.3, [M+H$^+$]=499.2, 250.1;

$^1$H NMR (500 MHz, DMSO-d$_6$) δ (ppm: 10.85 (1H, s. br.), 7.87 (1H, s.), 7.27 (1H, s.), 3.83 (3H, t), 3.60 (2H, d br.), 3.55-3.46 (2H, m), 3.18-3.04 (4H, m), 2.52 (3H, s), 2.00 (3H, s), 1.73 (4H, s. br.), 1.35 (9H, s.).

Example 5

1-[2-tert-Butyl-6-(trifluoromethyl)pyrimidin-4-yl]-4-[4-(4-hydroxy-5-methyl-2-oxopyrimidin-1 (2H)-yl)butyl]piperazin-4-ium chloride Method 1

40.9 mg (1.2 mmol) of $H_2O_2$ were added dropwise to 50.0 mg (0.1 mmol) of 1-[2-tert-butyl-6-(trifluoromethyl)pyrimidin-4-yl]-4-{4-[5-methyl-4-(methylthio)-2-oxopyrimidin-1 (2H)-yl]butyl}piperazine hydrochloride from Example 4 in 5 ml of glacial acetic acid at 10° C., and the mixture was stirred at room temperature for 3 hours. Then a further 40.9 mg (1.2 mmol) of $H_2O_2$ were added dropwise, and the reaction mixture was stirred at room temperature for a further six hours. Water was added to the reaction mixture, and then the aqueous mixture was extracted twice with dichloromethane. The organic phase was washed with an aqueous sodium thiosulfate solution until free of peroxides and then extracted once with dilute aqueous sodium carbonate solution and once with saturated aqueous brine. The residue after drying of the organic phase over $Na_2SO_4$, removal of the desiccant by filtration and evaporation of the solvent to dryness in vacuo was taken up in diethyl ether. A solution of HCl in diethyl ether was added, whereupon the required product precipitated as hydrochloride. The hydrochloride was filtered off with suction and washed with diethyl ether, and the title compound was dried in vacuo at 40° C. Yield: 25.0 mg.

Method 2

5.2.1 1-(4-Chlorobutyl)-4-hydroxy-5-methylpyrimidin-2(1H)-one 10.1 g (80.0 mmol) of 4-hydroxy-5-methylpyrimidin-2 (1H-one (thymine) in 300 ml of dimethyl sulfoxide (DMSO) and 11.1 g (80.0 mmol) of $K_2CO_3$ were stirred at room temperature for 1 hour. Then 13.7 g (80.0 mmol) of 1-bromo-4-chlorobutane were added dropwise to the mixture, and the reaction mixture was stirred at room temperature for 5 hours. Water was added to the reaction mixture, which was then extracted with ethyl acetate. The aqueous phase was then neutralized and extracted with methylene chloride. Drying of the organic phase, removal of the desiccant by filtration and evaporation of the solvent to dryness in vacuo resulted in 7.1 g of 1-(4-chlorobutyl)-4-hydroxy-5-methylpyrimidin-2(1H)-one.

ESI-MS: 219.1, [M+H$^+$]=217.1;

$^1$H NMR (500 MHz, CDCl$_3$) δ (ppm: 9.97 (1H, s.), 7.02 (1H, s.), 3.74 (2H, t), 3.55 (2H, t), 1.93 (3H, s), 2.02-1.75 (4H, m).

5.2.2 1-[2-tert-Butyl-6-(trifluoromethyl)pyrimidin-4-yl]-4-[4-(4-hydroxy-5-methyl-2-oxopyrimidin-1 (2H)-yl)butyl]piperazin-4-ium chloride 1.5 g (7.0 mmol) of 1-(4-chlorobutyl)-4-hydroxy-5-methylpyrimidin-2(1H)-one from Example 5.2.1, 2.0 g (7.0 mmol) of 2-tert-butyl-4-piperazin-1-yl-6-(trifluoromethyl) pyrimidine (DE 197 35 410) and 1.4 g (14.0 mmol) of NEt$_3$ in 100 ml of N,N-dimethylformamide (DMF) were stirred at 110° C. for 24 hours. Then ethyl acetate was added, and the mixture was washed twice with water. The combined organic phases were dried over $Na_2SO_4$, filtered to remove the desiccant and concentrated in vacuo. The oily residue was purified by chromatography on silica gel (eluent: dichloromethane: methanol 95:5 v/v), and stirred with pentane and filtered off with suction. The solid was taken up in a little methylene chloride, and a solution of HCl in diethyl ether was added, whereupon the required product precipitated as hydrochloride. The hydrochloride was filtered off with suction and washed with diethyl ether, and the title compound was dried in vacuo at 40° C. Yield: 1.1 g.

ESI-MS: 470.5, [M+H$^+$]=469.5, 235.3;

$^1$H NMR (500 MHz, DMSO-d$_6$) δ (ppm: 11.57 (1H, s. br.), 11.23 (1H, s.), 7.62 (1H, s.), 7.24 (1H, s.), 4.68 (2H, s. br.), 3.65 (2H, t), 3.55 (4H, d br.), 3.14-3.00 (4H, m), 1.82-1.71 (3+2H, s+m), 1.68-1.59 (2H, m), 1.31 (9H, s).

Example 6

1-(4-{4-[2-tert-Butyl-6-(trifluoromethyl)pyrimidin-4-yl]piperazin-1-yl}butyl)-5-methylpyrimidin-2 (1H)-one 6.1 5-Methylpyrimidin-2(1H)-one (Chem. Ztg. 1977, 6, 305-7)

11.4 g (0.1 mol) of (2Z)-3-ethoxy-2-methylprop-2-enal (3-ethoxymethacrolein), 6.0 g (0.1 mol) of carbamide (urea) and 10 ml of conc. HCl solution in 20 ml of ethanol were heated under reflux for 3.5 hours. The reaction mixture was then allowed to cool and was cooled with ice-water, whereupon a precipitate formed. The precipitated crystals were filtered off with suction, washed with ethanol and dried at 40° C. in vacuo. Yield: 11.0 g.

ESI-MS: [2M+Na$^+$]=243.1, [M+H$^+$]=111.1;

$^1$H NMR (400 MHz, DMSO-d$_6$) δ (ppm): 8.68 (2H, s.), 2.12 (3H, s.).

6.2 1-(4-Chlorobutyl)-5-methylpyrimidin-2(1H)-one 10.5 g (95.0 mmol) of 5-methylpyrimidin-2(1H)-one from Example 6.1, 16.3 g (95.0 mmol) of 1-bromo-4-chlorobutane and 39.4 g (285.0 mmol) of $K_2CO_3$ in 200 ml of dimethyl sulfoxide were stirred at room temperature for 12 hours. The reaction mixture was added to ice-water, and the aqueous mixture was extracted twice with diethyl ether. The aqueous phase was extracted twice with methylene chloride. The methylene chloride phase was dried over $Na_2SO_4$ and filtered to remove the desiccant, and the solvent was evaporated to dryness in vacuo. The resulting solid residue was stirred with diethyl ether, and the precipitate was filtered off with suction, washed with diethyl ether and dried. Yield: 5.0 g.

$^1$H NMR (400 MHz, CDCl$_3$) δ (ppm): 8.46 (1H, d), 7.46 (1H, d), 3.90 (2H, t), 3.57 (2H, t), 2.11 (3H, s.), 1.95 (2H, quint.), 1.88-1.78 (2H, quint.).

6.3 1-(4-{4-[2-tert-Butyl-6-(trifluoromethyl)pyrimidin-4-yl]piperazin-1-yl}butyl)-5-methylpyrimidin-2(1H)-one The title compound was obtained in analogy to Example 5.2.2 starting from 1.4 g (5.0 mmol) of 1-(4-chlorobutyl)-5-methylpyrimidin-2(1H)-one from Example 6.2; yield: 0.5 g.

ESI-MS: 454.2, [M+H$^+$]=453.3, 227.1;

$^1$H NMR (500 MHz, DMSO-d$_6$) δ (ppm: 8.41 (1H, s.), 7.97 (1H, s.), 6.93 (1H, s.), 3.82 (2H, t), 3.69 (4H, s. br.), 2.42 (4H, m sym.), 2.35 (2H, t), 2.05 (3H, s), 1.70 (2H, quint.), 1.48 (2H, quint.), 1.28 (9H, s).

Example 7

1-(4-{4-[2-tert-Butyl-6-(trifluoromethyl)pyrimidin-4-yl]piperazin-1-yl}butyl)-5-methyl-4-phenoxypyrimidin-2(1H)-one

7.1 1-(4-{4-[2-tert-Butyl-6-(trifluoromethyl)pyrimidin-4-yl]piperazin-1-yl}butyl)-5-methyl-2-oxo-1,2-dihydropyrimidin-4-yl thiocyanate A solution of KCN (325.6 mg, 5.0 mmol) in 5% strength NaHCO$_3$ solution (7 ml) was added to 484.6 mg (1.0 mmol) of 1-(4-{4-[2-tert-butyl-6-(trifluoromethyl)pyrimidin-4-yl]piperazin-1-yl}butyl)-4-mercapto-5-methylpyrimidin-2(1H)-one from Example 2 in 20 ml of methylene chloride. Then a mixture of 2.0 mg of 18-crown-6 and 105.9 mg (1.0 mmol) of BrCN, in the minimum amount of methylene chloride necessary to dissolve, was added dropwise at 0° C. The organic phase was then separated off and washed twice with saturated aqueous brine. The organic phase was dried over Na$_2$SO$_4$ and filtered to remove the desiccant, and the solvent was evaporated to dryness in vacuo; yield: 420.0 mg. 1-(4-{4-[2-tert-Butyl-6-(trifluoromethyl)pyrimidin-4-yl]piperazin-1-yl}butyl)-5-methyl-2-oxo-1,2-dihydropyrimidin-4-yl thiocyanate was employed without additional purification in the next step.

7.2 1-(4-{4-[2-tert-Butyl-6-(trifluoromethyl)pyrimidin-4-yl]piperazin-1-yl}butyl)-5-methyl-4-phenoxypyrimidin-2(1H)-one 81.3 mg (0.9 mmol) of phenol and 325.5 mg (2.4 mmol) of K$_2$CO$_3$ were added to 400.0 mg (0.78 mmol) of 1-(4-{4-[2-tert-butyl-6-(trifluoromethyl)pyrimidin-4-yl]piperazin-1-yl}butyl)-5-methyl-2-oxo-1,2-dihydropyrimidin-4-yl thiocyanate from Example 7.1 in 40 ml of acetonitrile and 500.0 mg of molecular sieves (3 Å). The reaction mixture was then stirred at room temperature for 12 hours. Insolubles were filtered off, methylene chloride was added to the filtrate, followed by extraction with aqueous brine. The residue after drying of the organic phase, removal of the desiccant by filtration and evaporation of the solvent in vacuo was taken up in 100 ml of diisopropyl ether and heated. The precipitate was filtered off with suction and the mother liquor was concentrated somewhat. The mother liquor was then mixed with pentane and cooled in an ice bath. The precipitated solid was filtered off with suction, washed and dried in vacuo at 40° C., resulting in 120 mg of the title compound.

ESI-MS: 546.3, [M+H$^+$]=545.3, 273.1;

$^1$H NMR (500 MHz, CDCl$_3$) δ (ppm: 7.37 (2H, t), 7.32 (1H, s.), 7.20 (1H, t), 7.13 (1H, d), 6.56 (1H, s.), 3.85 (2H, t), 3.69 (4H, s br.), 2.50 (4H, m sym.), 2.41 (2H, t), 2.12 (3H, s.), 1.79 (2H, quint.), 1.57 (2H, quint.), 1.32 (9H, s.).

Example 8

1-(4-{4-[2-tert-Butyl-6-(trifluoromethyl)pyrimidin-4-yl]piperazin-1-yl}butyl)-4-methylpyrimidin-2(1H)-one

8.1 4-Methylpyrimidin-2(1H)-one (Analogous to Aust. J. Chem. 1968, 21, 243-55) 20.0 ml of conc. HCl were added dropwise to 26.4 g (0.2 mol) of 4,4-dimethoxybutan-2-one in 40 ml of ethanol and 12.0 g (0.2 mol) of urea. A clear brown solution was produced after a short time, and a yellow precipitate separated out after a further 10 minutes. The reaction mixture was heated under reflux for 1.5 hours and then allowed to cool (ice-water bath). The precipitated crystals were then filtered off with suction and washed with ethanol, and the crystals were dried in vacuo at 40° C.; yield: 22.0 g.

$^1$H NMR (400 MHz, DMSO-d$_6$) δ (ppm: 8.61 (1H, d), 6.81 (1H, d), 2.59 (3H, s.).

8.2 1-(4-Chlorobutyl)-4-methylpyrimidin-2(1H)-one 5.1 g of 1-(4-chlorobutyl)-4-methylpyrimidin-2(1H)-one were obtained in analogy to Example 6.2 from 12.1 g (0.1 mol) of 4-methylpyrimidin-2(1H)-one.

ESI-MS: [M+H$^+$]=201.1;

$^1$H NMR (400 MHz, CDCl$_3$) δ (ppm: 7.52 (1H, d), 6.22 (1H, d), 3.92 (2H, t), 3.57 (2H, t), 2.39 (3H, s.), 1.94 (2H, quint.), 1.86-1.74 (2H, m).

8.3 1-(4-{4-[2-tert-Butyl-6-(trifluoromethyl)pyrimidin-4-yl]piperazin-1-yl}butyl)-4-methylpyrimidin-2(1H)-one 0.25 g of the title compound was prepared in analogy to Example 5.2.2 from 1.1 g (5.5 mmol) of 1-(4-chlorobutyl)-4-methylpyrimidin-2(1H)-one.

ESI-MS: 454.2, [M+H$^+$]=453.3, 227.1;

$^1$H NMR (500 MHz, CDCl$_3$) δ (ppm): 7.48 (1H, d), 6.56 (1H, s.), 6.19 (1H, d), 3.90 (2H, t), 3.70 (4H, s. br.), 2.50 (4H, m sym.), 2.43 (2H, t), 2.40 (3H, s), 1.83 (2H, quint.), 1.59 (2H, quint.), 1.33 (9H, s.).

Example 9

1-{4-[4-(2,6-ditert-Butylpyrimidin-4-yl)piperazin-1-yl]butyl}-4-hydroxy-5-methylpyrimidin-2(1H)-one 170.0 mg of the title compound were obtained in analogy to Example 5.2.2 from 390.0 mg (1.8 mmol) of 1-(4-chlorobutyl)-4-hydroxy-5-methylpyrimidin-2(1H)-one from Example 5.2.1 and 414.6 mg (1.5 mmol) of 2,4-ditert-butyl-6-piperazin-1-ylpyrimidine.

ESI-MS: 458.4, [M+H$^+$]=457.4, 229.1;

$^1$H NMR (500 MHz, CDCl$_3$) δ (ppm: 9.29 (1H, s br.), 6.97 (1H, s.), 6.24 (1H, s), 3.72 (2H, t), 3.64 (4H, m sym.), 2.52 (4H, m sym.), 2.44 (2H, t), 1.93 (3H, s), 1.74 (2H, quint.), 1.58 (2H, quint.), 1.27 (9H, s.), 1.33 (9H, s.).

Example 10

1-{4-[4-(2-tert-Butyl-6-propylpyrimidin-4-yl)piperazin-1-yl]butyl}-4-hydroxy-5-methylpyrimidin-2(1H)-one 220.0 mg of the title compound were obtained in analogy to Example 5.2.2 from 390.0 mg (1.8 mmol) of 1-(4-chlorobutyl)-4-hydroxy-5-methylpyrimidin-2(1H)-one from Example 5.2.1 and 393.6 mg (1.5 mmol) of 2-tert-butyl-4-piperazin-1-yl-6-propylpyrimidine.
ESI-MS: 444.2, [M+H$^+$]=443.4, 222.1;
$^1$H NMR (500 MHz, CDCl$_3$) δ (ppm: 9.01 (1H, s.), 6.96 (1H, s.), 6.11 (1H, s.), 3.72 (2H, t), 3.62 (4H, m sym.), 2.57-2.49 (2+4H, m), 2.41 (2H, t), 1.93 (3H, s), 1.58 (2H, quint.), 1.31 (9H, s.).

Example 11

4-(Benzylamino)-1-(4-{4-[2-tert-butyl-6-(trifluoromethyl)pyrimidin-4-yl]piperazin-1-yl}butyl)-5-methylpyrimidin-2(1H)-one 0.5 g of the title compound was obtained in analogy to Example 5.2.2 from 2.0 g (4.0 mmol) of 1-(4-{4-[2-tert-butyl-6-(trifluoromethyl)pyrimidin-4-yl]piperazin-1-yl}butyl)-5-methyl-2-oxo-1,2-dihydropyrimidin-4-yl thiocyanate from Example 7.1 and 0.5 g (4.4 mmol) of benzylamine.
ESI-MS: 559.5, [M+H$^+$]=558.5, 279.8;
$^1$H NMR (500 MHz, CDCl$_3$) δ (ppm: 7.38 (1H, s), 7.34-7.24 (5H, m), 7.03 (1H, s. br.), 6.64 (1H, s.), 4.68 (2H, m sym.), 3.83 (2H, m), 3.11 (4H, s. br.), 2.85 (4H, s. br.), 2.04 (3H, s.), 1.84 (4H, s. br.), 1.31 (9H, s.).

Example 12

1-[2-tert-Butyl-6-(trifluoromethyl)pyrimidin-4-yl]-4-{4-[4-(dimethylamino)-5-methyl-2-oxopyrimidin-1(2H)-yl]butyl}piperazin-4-ium chloride 0.7 g of the title compound was obtained in analogy to Example 7.2 from 1.0 g (2.0 mmol) of 1-(4-{4-[2-tert-butyl-6-(trifluoromethyl)pyrimidin-4-yl]piperazin-1-yl}butyl)-5-methyl-2-oxo-1,2-dihydropyrimidin-4-yl thiocyanate from Example 7.1 and dimethylamine (2M in methanol, 1.1 ml).
ESI-MS: [M+H$^+$]=496.5, 248.7;
$^1$H NMR (500 MHz, DMSO-d$_6$) δ (ppm: 11.61 (1H, s. br.), 7.96 (1H, s.), 7.21 (1H, s), 3.76 (2H, t), 3.54 (2H, d br.), 3.27 (6H, s), 3.12-3.00 (2+2H, m), 2.20 (3H, s), 1.75-1.67 (2+2H, m), 1.30 (9H, s).

Example 13

1-(4-{4-[2-tert-Butyl-6-(trifluoromethyl)pyrimidin-4-yl}butyl)-4-hydroxypyrimidin-2(1H)-one 0.6 g of the title compound was obtained in analogy to Example 7.2 from 1.0 g (4.0 mmol) of 1-(4-bromobutyl)pyrimidine-2,4(1H,3H)-dione (*J. Am. Chem. Soc.* 1993, 115, 7636).
ESI-MS: 456.2, [M+H$^+$]=455.3, 228.1;
$^1$H NMR (500 MHz, CDCl$_3$) δ (ppm: 10.04 (1H, s. br.), 7.15 (1H, d), 6.58 (1H, s.), 5.68 (1H, d), 3.75 (2H, t), 3.70 (4H, s. br.), 2.51 (4H, t), 2.43 (2H, t), 1.74 (2H, quint.), 1.57 (2H, quint.), 1.33 (9H, s).

Example 14

4-tert-Butyl-1-(4-{4-[2-tert-butyl-6-(trifluoromethyl)pyrimidin-4-yl]piperazin-1-yl}butyl)pyrimidin-2(1H)-one

14.1 4-tert-Butyl-1-(4-chlorobutyl)pyrimidin-2(1H)-one 13.4 g of 4-tert-butyl-1-(4-chlorobutyl)pyrimidin-2(1H)-one were obtained in analogy to Example 6.2 from 16.7 g (0.1 mol) of 4-tert-butylpyrimidin-2(1H)-one.
$^1$H NMR (500 MHz, CDCl$_3$) δ (ppm: 7.54 (1H, d), 6.38 (1H, d), 3.92 (2H, t), 3.59 (2H, t), 1.97 (2H, quint.), 1.87 (2H, quint.), 1.30 (9H, s).

14.2 4-tert-Butyl-1-(4-{4-[2-tert-butyl-6-(trifluoromethyl)pyrimidin-4-yl]piperazin-1-yl}butyl)pyrimidin-2(1H)-one 0.8 g of the title compound was obtained in analogy to Example 5.2.2 from 1.21 g (5.0 mmol) of 4-tert-butyl-1-(4-chlorobutyl)pyrimidin-2(1H)-one from Example 14.1.
ESI-MS: 496.4, [M+H$^+$]=495.4, 248.1;
$^1$H NMR (500 MHz, CDCl$_3$) δ (ppm: 7.52 (1H, d), 6.58 (1H, s), 6.37 (1H, d), 3.91 (2H, t), 3.70 (4H, s br.), 2.48 (4H, t), 2.41 (2H, t), 1.86 (2H, quint.), 1.59 (2H, quint.), 1.35 (9H, s), 1.30 (9H, s).

Example 15

1-[2-tert-Butyl-6-(trifluoromethyl)pyrimidin-4-yl]-4-{4-[2-oxo-4-(trifluoromethyl)pyrimidin-1(2H)-yl]butyl}piperazin-4-ium chloride

15.1 1-(4-Chlorobutyl)-4-(trifluoromethyl)pyrimidin-2(1H)-one 4.6 g (28.3 mmol) of 2-hydroxy-4-trifluoromethylpyrimidine were stirred in 60 ml of N,N-dimethylformamide (DMF) and 3.9 g (28.3 mmol) of K$_2$CO$_3$ at room temperature for 1 hour. Then 4.9 g (28.3 mmol) of 1-bromo-4-chlorobutane were added dropwise, and the reaction mixture was stirred at room temperature for 6 hours. Water was then added to the reaction mixture, and the aqueous mixture was extracted with diethyl ether. The aqueous phase was made alkaline by adding NaOH, and the aqueous phase was extracted with methylene chloride. The organic phase was then dried, the desiccant was removed by filtration, and the solvent was evaporated to dryness in vacuo; yield: 1.7 g.
ESI-MS: [M+Na$^+$]=257.0, [M+H$^+$]=255.1;

15.2 1-[2-tert-Butyl-6-(trifluoromethyl)pyrimidin-4-yl]-4-{4-[2-oxo-4-(trifluoromethyl)-pyrimidin-1(2H)-yl]butyl}piperazin-4-ium chloride 0.53 g of the title compound was obtained in analogy to Example 5.2.2 from 0.6 g (2.36 mmol) of 1-(4-chlorobutyl)-4-(trifluoromethyl)pyrimidin-2(1H)-one from Example 15.1.
ESI-MS: [M+Na$^+$]=529.3, 508.3, [M+H$^+$]=507.2, 254.1;
$^1$H NMR (500 MHz, DMSO-d$_6$) δ (ppm): 11.37 (1H, s br.), 8.69 (1H, d), 7.20 (1H, s), 6.89 (1H, d), 4.23 (4H, s br.), 3.98 (2H, t), 3.54 (4H, m br.), 3.14-2.98 (4H, m br.), 1.75 (4H, s br.), 1.30 (9H, s).

Example 16

1-[2-tert-Butyl-6-(trifluoromethyl)pyrimidin-4-yl]-4-[4-(5-fluoro-2,4-dioxo-3,4-dihydro-pyrimidin-1(2H)-yl)butyl]piperazin-4-ium chloride

16.1 1-(4-Chlorobutyl)-5-fluoropyrimidine-2,4(1H,3H)-dione 2.6 g (15.0 mmol) of 1-bromo-4-chlorobutane were added dropwise to a solution of 1.95 g (15.0 mmol) of 2,4-dihydroxy-5-fluoropyrimidine in 50 ml of dimethyl sulfoxide and 20.0 ml of N,N-dimethylformamide (DMF) at 0° C. 2.07 g (15.0 mmol) of K$_2$CO$_3$ were added in portions over the course of 1 hour, and the mixture was stirred at 20° C. for 1 hour (dialkylated product is already identifiable). Water was then added to the reaction mixture, and the aqueous mixture was extracted twice with diethyl ether and twice with methylene chloride. The aqueous phase was adjusted to pH 3-4 with hydrochloric acid and then the aqueous phase was extracted with methylene chloride. The organic phase was then dried, the desiccant was removed by filtration, and the solvent was evaporated to dryness in vacuo; yield: 0.6 g. 1-(4-Chlorobutyl)-5-fluoropyrimidine-2,4(1H,3H)-dione was employed without further purification in the next step.

16.2 1-[2-tert-Butyl-6-(trifluoromethyl)pyrimidin-4-yl]-4-[4-(5-fluoro-2,4-dioxo-3,4-dihydropyrimidin-1(2H)-yl)butyl]piperazin-4-ium chloride 0.03 g of the title compound was obtained in analogy to Example 5.2.2 from 0.66 g (3.00 mmol) of 1-(4-chlorobutyl)-5-fluoropyrimidine-2,4(1H,3H)-dione.
ESI-MS: 474.5, [M+H$^+$]=473.5, 237.3.

Example 17

1-{4-[4-(2-tert-Butyl-6-cyclopropylpyrimidin-4-yl)piperazin-1-yl]butyl}-4-hydroxy-5-methylpyrimidin-2(1H)-one 0.18 g of the title compound was obtained in analogy to Example 5.2.2 from 0.43 g (2.00 mmol) of 1-(4-chlorobutyl)-5-methylpyrimidine-2,4(1H,3H)-dione from step 5.2.1 and 0.52 g (2.00 mmol) of 2-tert-butyl-4-cyclopropyl-6-piperazin-1-ylpyrimidine.
ESI-MS: 442.5, [M+H$^+$]=441.5, 221.3;
$^1$H NMR (500 MHz, CDCl$_3$) δ (ppm: 8.80 (1H, s br.), 6.97 (1H, s), 6.15 (1H, s), 3.71 (2H, t), 3.62 (4H, t br.), 2.48 (4H, t), 2.40 (2H, t), 1.93 (3H, s), 1.81-1.66 (1+2H, m), 1.57 (2H, quint.), 1.27 (9H, s), 1.07 (2H, m sym.), 0.85 (2H, m sym.).

Example 18

1-(4-{4-[2-tert-Butyl-6-(trifluoromethyl)pyrimidin-4-yl]piperazin-1-yl}butyl)-2,4-dioxo-1,2,3,4-tetrahydropyrimidine-5-carbonitrile

18.1 1-(4-Chlorobutyl)-2,4-dioxo-1,2,3,4-tetrahydropyrimidine-5-carbonitrile 2.6 g (15.0 mmol) of 1-bromo-4-chlorobutane were added dropwise to a solution of 2.06 g (15.0 mmol) of 5-cyanouracil in 50 ml of dimethyl sulfoxide (DMSO) and 20.0 ml of N,N-dimethylformamide (DMF) at 0° C., and 2.07 g (15.0 mmol) of K$_2$CO$_3$ were added in portions over the course of 1 hour. The mixture was then stirred at 20° C. for 10 minutes (dialkylated product already identifiable). Water was added to the reaction mixture, and then the aqueous mixture was extracted twice with diethyl ether and twice with methylene chloride. The aqueous phase was adjusted to pH 3-4 and then extracted with methylene chloride. The methylene chloride phase was then dried, the desiccant was removed by filtration, and the solvent was evaporated to dryness in vacuo; yield: 0.6 g. 1-(4-Chlorobutyl)-2,4-dioxo-1,2,3,4-tetrahydropyrimidine-5-carbonitrile was employed without further purification in the next step.
ESI-MS: [M+H$^+$]=228.05.

18.2 1-(4-{4-[2-tert-Butyl-6-(trifluoromethyl)pyrimidin-4-yl]piperazin-1-yl}butyl)-2,4-dioxo-1,2,3,4-tetrahydropyrimidine-5-carbonitrile 0.07 g of the title compound was obtained in analogy to Example 5.2.2 from 0.68 g (3.00 mmol) of 1-(4-chlorobutyl)-2,4-dioxo-1,2,3,4-tetrahydropyrimidine-5-carbonitrile from Example 18.1.
ESI-MS: 481.5, [M+H$^+$]=480.5, 240.7;
$^1$H NMR (500 MHz, CDCl$_3$) δ (ppm): 8.02 (1H, s), 6.59 (1H, s), 3.84 (2H, t), 3.71 (4H, s br.), 2.50 (4H, t br.), 2.41 (2H, t), 1.79 (2H, quint.), 1.56 (2H, quint.), 1.32 (9H, s).

Example 19

4-tert-Butyl-1-{4-[4-(2-tert-butyl-6-cyclopropylpyrimidin-4-yl)piperazin-1-yl]butyl}pyrimidin-2(1H)-one 0.11 g of the title compound was obtained in analogy to Example 5.2.2 from 0.49 g (2.00 mmol) of 4-tert-butyl-1-(4-chlorobutyl)pyrimidin-2(1H)-one from Example 14.1 and 0.52 g (2.00 mmol) of 2-tert-butyl-4-cyclopropyl-6-piperazin-1-ylpyrimidine.
ESI-MS: 468.5, [M+H$^+$]=467.4, 234.2;
$^1$H NMR (500 MHz, CDCl$_3$) δ (ppm: 7.51 (1H, d), 6.36 (1H, d), 6.14 (1H, s), 3.91 (2H, t), 3.61 (4H, t br.), 2.46 (4H, t br.), 2.38 (2H, t), 1.86-1.74 (2+1H, m), 1.57 (2H, quint.), 1.31 (9H, s), 1.27 (9H, s), 1.07 (2H, m sym.), 0.87 (2H, m sym.).

Example 20

1-{4-[4-(2-tert-Butyl-6-propylpyrimidin-4-yl)piperazin-1-yl]butyl}-4-hydroxypyrimidin-2(1H)-one 1.8 g of the title compound were obtained in analogy to Example 5.2.2 from 1.7 mg (8.4 mmol) of 1-(4-chlorobutyl)-4-hydroxypyrimidin-2(1H)-one (obtainable in analogy to the preparation of 1-(4-bromobutyl)pyrimidine-2,4(1H,3H)-dione, see Example 13) and 1.84 mg (7.0 mmol) of 2-tert-butyl-4-piperazin-1-yl-6-propylpyrimidine.
ESI-MS: 430.4, [M+H$^+$]=429.4, 215.1;
$^1$H NMR (500 MHz, CDCl$_3$) δ (ppm: 9.43 (1H, s br.), 7.13 (1H, d), 6.11 (1H, s), 5.68 (1H, d), 3.78 (2H, t), 3.63 (4H, s br.), 2.58-2.48 (4H, m), 2.43 (2H, t), 1.79-1.66 (2+1H, m), 1.57 (2H, quint.), 1.31 (9H, s), 0.94 (3H, t).

Example 21

1-[4-(4-tert-Butyl-2-oxopyrimidin-1(2H)-yl)butyl]-4-(2-tert-butyl-6-propylpyrimidin-4-yl)piperazin-1-ium chloride 1.8 g of the title compound were obtained in analogy to Example 5.2.2 from 2.04 g (8.40 mmol) of 4-tert-butyl-1-(4-chlorobutyl)pyrimidin-2(1H)-one from Example 14.1 and 1.84 mg (7.0 mmol) of 2-tert-butyl-4-piperazin-1-yl-6-propylpyrimidine.
ESI-MS: 470.5, [M+H$^+$]=469.4, 235.3, 157.2;
$^1$H NMR (500 MHz, DMSO-d$_6$) δ (ppm: 14.13 (1H, s br.), 11.89 (1H, s br.), 8.59 (1H, d), 6.73 (1H, d), 5.00 (1H, d br.), 4.47 (1H, d br.), 3.61 (3H, d br.), 3.14 (4H, s br.), 2.88 (2H, t), 1.84-1.66 (6H, m), 1.43 (9H, s), 1.28 (9H, s), 0.94 (3H, t).

Example 22

1-{4-[4-(2-tert-Butyl-6-cyclobutylpyrimidin-4-yl) piperazin-1-yl]butyl}-4-hydroxy-5-methylpyrimidin-2(1H)-one 0.11 g of the title compound was obtained in analogy to Example 5.2.2 from 0.30 g (1.10 mmol) of 2-tert-butyl-4-cyclobutyl-6-piperazin-1-ylpyrimidine.
ESI-MS: 456.4, [M+H$^+$]=455.4, 228.2;
$^1$H NMR (500 MHz, CDCl$_3$) δ (ppm: 8.88 (1H, s br.), 6.97 (1H, s), 6.11 (1H, s), 3.71 (2H, t), 3.63 (4H, s br.), 3.42 (1H, t), 2.49 (4H, t), 2.41 (2H, t), 2.27 (4H, m), 2.00 (1H, sext.), 1.92 (3H, s), 1.92-1.84 (1H, m), 1.72 (2H, quint.), 1.56 (2H, quint.), 1.32 (9H, s).

Example 23

1-{4-[4-(2-tert-Butyl-6-cyclobutylpyrimidin-4-yl) piperazin-1-yl]butyl}pyrimidine-2,4(1H,3H)-dione 0.14 g of the title compound was obtained in analogy to Example 5.2.2 from 0.28 g (1.40 mmol) of 1-(4-chlorobutyl)-4-hydroxypyrimidin-2(1H)-one (obtainable in analogy to the preparation of 1-(4-bromobutyl)pyrimidine-2,4(1H,3H)-dione, see Example 13) and 0.30 g (1.10 mmol) of 2-tert-butyl-4-cyclobutyl-6-piperazin-1-ylpyrimidine.
ESI-MS: 442.5, [M+H$^+$]=441.5;
$^1$H NMR (500 MHz, CDCl$_3$) δ (ppm: 7.15 (1H, d), 6.11 (1H, s), 5.69 (1H, d), 3.77 (2H, t), 3.63 (4H, s br.), 3.42 (1H, quint.), 2.51 (4H, t), 2.42 (2H, t), 2.32-2.20 (2+2H, m), 2.05-1.84 (1+1H, m), 1.75 (2H, quint.), 1.56 (2H, quint.), 1.31 (9H, s).

Example 24

1-(4-{4-[2-tert-Butyl-6-(trifluoromethyl)pyrimidin-4-yl]piperazin-1-yl}butyl)-4-phenylpyrimidin-2(1H)-one 24.1 2-Chloro-4-phenylpyrimidine 2.78 g (20.14 mmol) of K$_2$CO$_3$, 0.21 g (0.18 mmol) of tetrakis(triphenylphosphine)Pd(0) were added to 1.00 g (6.71 mmol) of 2,4-dichloropyrimidine and 0.82 g (6.71 mmol) of benzeneboronic acid in 29 ml of toluene and 7 ml of methanol, and the reaction mixture was stirred at room temperature for 3 hours. The residue after concentration of the reaction mixture was taken up in water/methyl tert-butyl ether. The aqueous phase was then extracted twice with methyl tert-butyl ether. Thereafter the combined organic phase was washed with water and with a saturated aqueous NaCl solution, and the organic phase was dried, filtered to remove the desiccant and concentrated. The solid brown residue was purified by flash chromatography on silica gel (mobile phase: ethyl acetate/cyclohexane: 10:90); yield: 0.90 g.
$^1$H NMR (400 MHz, CDCl$_3$) δ (ppm: 8.64 (1H, d), 8.10 (2H, d), 7.650 (1H, d), 7.58-7.48 (3H, m).

24.2 4-Phenylpyrimidin-2-ol 0.80 g (4.20 mmol) of 2-chloro-4-phenylpyrimidine from Example 24.1 was heated in 3.20 ml of conc. HCl at 100° C. for 1 hour. The mixture was then concentrated, suspended in methylene chloride and again concentrated. Yield: 0.83 g.
ESI-MS: 174.3, [M+H$^+$]=173.2;

24.3

1-(4-Chlorobutyl)-4-phenylpyrimidin-2(1H)-one 0.84 g (4.20 mmol) of 4-phenylpyrimidin-2-ol from Example 24.2 was stirred in 8.4 ml of N,N-dimethylformamide (DMF) and 0.58 g (4.20 mmol) of K$_2$CO$_3$ at room temperature for 1 hour. Then 0.72 g (4.20 mmol) of 1-bromo-4-chlorobutane was added dropwise, the reaction mixture was stirred at room temperature for 12 hours, and the reaction mixture was filtered and concentrated. The residue was then taken up in toluene and concentrated, and the residue was again taken up in toluene and concentrated. The resulting residue was stirred with pentane and filtered. Yield: 0.74 g.
$^1$H NMR (400 MHz, CDCl$_3$) δ (ppm: 8.10 (2H, d), 7.71 (1H, d), 7.63-7.40 (3H, m), 6.82 (1H, d), 3.98 (2H, t), 3.58 (2H, t), 2.00 (2H, quint.), 1.90 (2H, quint.).

24.4 1-(4-{4-[2-tert-Butyl-6-(trifluoromethyl)pyrimidin-4-yl]piperazin-1-yl}butyl)-4-phenylpyrimidin-2(1H)-one 0.32 g of the title compound was obtained in analogy to Example 5.2.2 from 0.74 g (2.82 mmol) of 1-(4-chlorobutyl)-4-phenylpyrimidin-2(1H)-one from Example 24.3.
ESI-MS: [M+H$^+$]=515.2, 258.1;
$^1$H NMR (500 MHz, CDCl$_3$) δ (ppm): 8.08 (2H, d), 7.86 (1H, d), 7.52 (1H, t), 7.46 (1H, t), 6.79 (1H, d), 6.57 (1H, s), 3.99 (2H, t), 3.69 (4H, s br.), 2.49 (4H, t), 2.42 (2H, t), 1.89 (2H, quint.), 1.61 (2H, quint.), 1.33 (9H, s).

Example 25

1-(4-{4-[2-tert-Butyl-6-(trifluoromethyl)pyrimidin-4-yl]piperazin-1-yl}butyl)-3,5-dimethylpyrimidine-2,4(1H,3H)-dione 25.1 1-(4-Chlorobutyl)-3,5-dimethylpyrimidine-2,4 (1H,3H)-dione 2.31 mmol (0.50 g) of 1-(4-chlorobutyl)-5-methylpyrimidine-2,4(1H,3H)-dione, 0.65 g (11.54 mmol) of KOH and 1.64 g (11.54 mmol) of methyl rodide in 20.5 ml of dimethyl sulfoxide (DMSO) were stirred at room temperature for 5 hours. Water was added to the reaction mixture, and the aqueous mixture was extracted three times with methyl tert-butyl ether. The combined organic phase was then washed three times with saturated aqueous brine, and the organic phase was dried, filtered to remove the desiccant and concentrated. 0.53 g of a pale cloudy oil was obtained.
ESI-MS: [M+H$^+$]=231.15;

25.2 1-(4-{4-[2-tert-Butyl-6-(trifluoromethyl)pyrimidin-4-yl]piperazin-1-yl}butyl)-3,5-dimethylpyrimidine-2,4(1H,3H)-dione 0.54 g of the title compound was obtained in analogy to Example 5.2.2 from 0.53 g (2.30 mmol) of 1-(4-chlorobutyl)-3,5-dimethylpyrimidine-2,4(1H,3H)-dione from Example 25.1.
$^1$H NMR (500 MHz, CDCl$_3$) δ (ppm): 6.98 (1H, s), 6.59 (1H, s), 3.76 (2H, t), 3.70 (4H, s br.), 3.37 (3H, s), 2.50 (3H, t), 2.41 (2H, t), 1.94 (3H, s), 1.74 (2H, quint.), 1.56 (2H, quint.), 1.33 (9H, s).

Example 26

1-(4-{4-[2-tert-Butyl-6-(trifluoromethyl)pyrimidin-4-yl]piperazin-1-yl}butyl)-5-methyl-4-phenylpyrimidin-2(1H)-one

26.1 2-Chloro-5-methyl-4-phenylpyrimidine 0.57 g of 2-chloro-5-methyl-4-phenylpyrimidine was obtained in analogy to Example 24.1 from 1.00 g (6.13 mmol) of 2,4-dichloro-5-methylpyrimidine.
$^1$H NMR (400 MHz, CDCl$_3$) δ (ppm): 8.47 (1H, s), 7.57 (2H, m), 7.47 (3H, m).

26.2 5-Methyl-4-phenylpyrimidin-2-ol

A 100% yield of 5-methyl-4-phenylpyrimidin-2-ol was obtained in analogy to Example 24.2 from 0.57 g (2.79 mmol) of 2-chloro-5-methyl-4-phenylpyrimidine from Example 26.1.
ESI-MS: [M+H$^+$]=187.15;

26.3 1-(4-Chlorobutyl)-5-methyl-4-phenylpyrimidin-2(1H)-one 0.29 g of 1-(4-chlorobutyl)-5-methyl-4-phenylpyrimidin-2(1H)-one was obtained in analogy to Example 24.3 from 0.52 g (2.79 mmol) of 5-methyl-4-phenylpyrimidin-2-ol from Example 26.2.
$^1$H NMR (500 MHz, CDCl$_3$) δ (ppm): 7.60 (2H, d), 7.46 (1H, s), 7.41 (3H, m), 3.96 (2H, t), 3.60 (2H, t), 2.14 (2H, t), 2.01 (2H, quint.), 1.89 (2H, quint.).

26.4 1-(4-{4-[2-tert-Butyl-6-(trifluoromethyl)pyrimidin-4-yl]piperazin-1-yl}butyl)-5-methyl-4-phenylpyrimidin-2(1H)-one 0.14 g of the title compound was obtained in analogy to Example 5.2.2 from 0.29 g (1.05 mmol) of 1-(4-chlorobutyl)-5-methyl-4-phenylpyrimidin-2(1H)-one from Example 26.3.
$^1$H NMR (500 MHz, CDCl$_3$) δ (ppm): 7.61 (2H, d), 7.49-7.41 (3H, m), 6.58 (1H, s), 3.98 (2H, t), 3.70 (4H, s br.), 2.52 (4H, t), 2.43 (2H, t), 2.14 (3H, s), 1.89 (2H, quint.), 1.63 (2H, quint.), 1.37 (9H, s).

Example 27

1-(4-{4-[2-tert-Butyl-6-(trifluoromethyl)pyrimidin-4-yl]piperazin-1-yl}butyl)-3-methylpyrimidine-2,4(1H,3H)-dione

27.1 1-(4-Chlorobutyl)-3-methylpyrimidine-2,4(1H,3H)-dione 0.31 g of 1-(4-chlorobutyl)-3-methylpyrimidine-2,4(1H,3H)-dione was obtained as a colorless oil in analogy to Example 25.1 from 0.50 g (2.47 mmol) of 1-(4-chlorobutyl)-4-hydroxypyrimidin-2(1H)-one (obtainable in analogy to the preparation of 1-(4-bromobutyl)pyrimidine-2,4(1H,3H)-dione (see Example 13).
ESI-MS: [M+H$^+$]=217.15.

27.2 1-(4-{4-[2-tert-Butyl-6-(trifluoromethyl)pyrimidin-4-yl]piperazin-1-yl}butyl)-3-methylpyrimidine-2,4(1H,3H)-dione 0.14 g of the title compound was obtained in analogy to Example 5.2.2 from 0.31 g (1.43 mmol) of 1-(4-chlorobutyl)-3-methylpyrimidine-2,4(1H,3H)-dione from Example 27.1.

$^1$H NMR (500 MHz, CDCl$_3$) δ (ppm): 7.13 (1H, d), 6.56 (1H, s), 5.76 (1H, d), 3.79 (2H, t), 3.70 (4H, s br.), 3.33 (3H, s), 2.51 (4H, t), 2.43 (2H, t), 1.78 (2H, quint.), 1.58 (2H, quint.), 1.34 (9H, s).

Example 28

1-(4-{4-[2-tert-Butyl-6-(trifluoromethyl)pyrimidin-4-yl]piperazin-1-yl}butyl)pyrimidin-2(1H)-one Preparation took place in the manner described in Example 14.

Example 29

1-{4-[4-(2-tert-Butyl-6-methylpyrimidin-4-yl)piperazin-1-yl]butyl}-4-hydroxy-5-methylpyrimidin-2(1H)-one The title compound was obtained in analogy to Example 5.2.2 by reacting 1-(4-chlorobutyl)-4-hydroxy-5-methylpyrimidin-2(1H)-one (3.80 mmol, 0.82 g) with 2-tert-butyl-4-piperazin-1-yl-6-trifluoromethylpyrimidine; yield 0.40 g.
ESI-MS: 416.5, [M+H$^+$]=415.5;
$^1$H NMR (500 MHz, CDCl$_3$) δ (ppm): 9.19 (1H, s br.), 6.97 (1H, s), 6.13 (1H, s), 3.73 (2H, t), 3.63 (4H, m br.), 2.51 (4H, m), 2.42 (2H, t), 2.35 (3H, s), 1.92 (3H, s), 1.74 (2H, quint.), 1.56 (2H, quint.), 1.33 (9H, s).

Example 30

4-Hydroxy-5-methyl-1-{4-[4-(5,6,7,8-tetrahydronaphthalen-1-yl)piperazin-1-yl]butyl}pyrimidin-2(1H)-one The title compound was obtained in analogy to Example 5.2.2 by reacting 1-(4-chlorobutyl)-4-hydroxy-5-methylpyrimidin-2(1H)-one (5.00 mmol, 1.08 g) with 4-(piperazin-1-yl)-5,6,7,8-tetrahydronaphthalene; yield 0.34 g.
ESI-MS: 398.4, [M+H$^+$]=397.4, 199.3;
$^1$H NMR (500 MHz, CDCl$_3$) δ (ppm): 9.07 (1H, s br.), 7.08 (1H, t), 7.00 (1H, s), 6.87 (1H, d), 6.82 (1H, d), 3.75 (2H, t), 2.95 (4H, s), 2.79 (2H, m), 2.71 (2H, m), 2.63 (4H, s br.), 2.47 (2H, t), 1.94 (3H, s), 1.76 (2H, quint.), 1.59 (2H, quint.).

Example 31

1-(4-{4-[2-tert-Butyl-6-(trifluoromethyl)pyrimidin-4-yl]piperazin-1-yl}butyl)-4,6-dimethylpyrimidin-2(1H)-one The title compound was obtained in analogy to Example 5.2.2 by reacting 1-(4-bromobutyl)-4,6-dimethylpyrimidin-2(1H)-one (1.54 mmol, 0.40 g, prepared from 4,6-dimethyl-2-hydroxypyrimidine in analogy to J. Am. Chem. Soc. 1993, 115, 7643 via 4,6-dimethyl-2-[(trimethylsilyl)oxy]pyrimidine) with 2-tert-butyl-4-piperazin-1-yl-6-trifluoromethylpyrimidine.
ESI-MS: 290.3, [M+H$^+$]=289.2, 165.6;

Example 32

1-[4-(4-tert-Butyl-2-oxopyrimidin-1(2H)-yl)butyl]-4-(2,6-di-tert-butylpyrimidin-4-yl)piperazin-1-ium chloride The title compound was obtained in analogy to Example 5.2.2 by reacting 4-tert-butyl-1-(4-chlorobutyl)pyrimidin-2

(1H)-one (2.50 mmol, 0.61 g, see Example 14.1) with 2,6-di-tert-butyl-4-(piperazin-1-yl)pyrimidine; yield 0.29 g.

ESI-MS: 484.4, [M+H$^+$]=483.4, 242.3;

$^1$H NMR (400 MHz, CDCl$_3$) δ (ppm): 7.52 (1H, d), 6.37 (1H, d), 6.26 (1H, s), 3.93 (2H, t), 3.64 (4H, m), 2.50 (4H, m), 2.40 (2H, t), 1.83 (2H, quint.), 1.56 (2H, quint.), 1.39-1.17 (27H, m).

Example 33

1-{4-[4-(2,6-di-tert-Butylpyrimidin-4-yl)piperazin-1-yl]butyl}pyrimidine-2,4(1H,3H)-dione The title compound was obtained in analogy to Example 5.2.2 by reacting 1-(4-bromobutyl)pyrimidine-2,4(1H,3H)-dione (2.50 mmol, 0.51 g) with 2,6-di-tert-butyl-4-(piperazin-1-yl)pyrimidine; yield 0.45 g.

ESI-MS: 444.4, [M+H$^+$]=443.2, 222.1;

$^1$H NMR (400 MHz, CDCl$_3$) δ (ppm: 8.86 (1H, s br.), 7.15 (1H, d), 6.25 (1H, s), 5.68 (1H, d), 3.74 (2H, t), 3.63 (4H, m), 2.51 (4H, m), 2.40 (2H, t), 1.75 (2H, quint.), 1.57 (2H, quint.), 1.33 (9H, s), 1.27 (9H, s).

Example 34

4-(2,6-di-tert-Butylpyrimidin-4-yl)-1-[4-(4-methyl-2-oxopyrimidin-1 (2H)-yl)butyl]piperazin-1-ium chloride The title compound was obtained in analogy to Example 5.2.2 by reacting 1-(4-chlorobutyl)-4-methylpyrimidin-2 (1H)-one (2.50 mmol, 0.50 g) with 2,6-di-tert-butyl-4-(piperazin-1-yl)pyrimidine; yield 0.25 g.

ESI-MS: 442.3, [M+H$^+$]=441.2, 221.1;

Example 35

4-(2-tert-Butyl-6-propylpyrimidin-4-yl)-1-[4-(4-methyl-2-oxopyrimidin-1 (2H)-yl)butyl]piperazin-1-ium chloride The title compound was obtained in analogy to Example 5.2.2 by reacting 1-(4-chlorobutyl)-4-methylpyrimidin-2 (1H)-one (2.50 mmol, 0.50 g) with 2-tert-butyl-4-(piperazin-1-yl)-6-propylpyrimidine; yield 0.22 g.

$^1$H NMR (400 MHz, CDCl$_3$) δ (ppm: 7.48 (1H, d), 6.19 (1H, d), 6.12 (1H, s), 3.88 (2H, t), 3.60 (4H, m), 2.50 (2H, t), 2.47-2.42 (4H, m), 2.33 (5H, m), 1.88-1.62 (4H, m), 1.55 (2H, quint.), 1.30 (9H, s), 0.94 (3H, t).

Example 36

1-((2E)-4-{4-[2-tert-Butyl-6-(trifluoromethyl)pyrimidin-4-yl]piperazin-1-yl}-2-methylbut-2-en-1-yl)-5-methylpyrimidine-2,4(1H,3H)-dione The title compound was obtained in analogy to Example 5.2.2 by reacting thymine (3.50 mmol, 0.44 g) with 2-tert-butyl-4-{4-[(2E)-4-chloro-3-methylbut-2-en-1-yl]piperazin-1-yl}-6-trifluoromethylpyrimidine (3.50 mmol, 1.50 g, prepared as in DE 19735410); yield 0.78 g.

ESI-MS: 482.2, [M+H$^+$]=481.2, 241.1;

Example 37

1-(4-{4-[2-tert-Butyl-6-(trifluoromethyl)pyrimidin-4-yl]piperazin-1-yl}-2-methylbutyl)-5-methylpyrimidine-2,4(1H,3H)-dione 1-((2E)-4-{4-[2-tert-Butyl-6-(trifluoromethyl)pyrimidin-4-yl]piperazin-1-yl}-2-methylbut-2-en-1-yl)-5-methylpyrimidine-2,4(1H,3H)-dione (Example 36, 1.04 mmol, 0.50 g) in methanol (5 ml) was hydrogenated over Pd (10% on activated carbon) with hydrogen at room temperature for 12 h and then at 40° C. for a further 6 h. The mixture was filtered and the residue was washed with methanol. The filtrate was concentrated and purified on silica gel (mobile phase: dichloromethane/methanol: 97/3 v/v); yield 0.20 g.

ESI-MS: 484.2, [M+H$^+$]=483.3, 242.1;

Example 38

4-(2-tert-Butyl-6-propylpyrimidin-4-yl)-1-[1-methyl-4-(5-methyl-2,4-dioxo-3,4-dihydropyrimidin-1 (2H)-yl)butyl]piperazin-1-ium chloride The title compound was obtained in analogy to Example 5.2.2. by reacting 1-(4-bromopentyl)-5-methylpyrimidine-2,4(1H,3H)-dione (0.47 mmol, 0.13 g, prepared in analogy to Example 6.2 from thymine and 1,4-dibromopentane) with 2-tert-butyl-4-piperazin-1-yl-6-propylpyrimidine; yield 0.03 g.

ESI-MS: 458.5, [M+H$^+$]=457.5, 229.3;

Example 39

4-(2-tert-Butyl-6-isopropylpyrimidin-4-yl)-1-[4-(4-methyl-2-oxopyrimidin-1 (2H)-yl)butyl]piperazin-1-ium chloride The title compound was obtained in analogy to Example 5.2.2 by reacting 1-(4-chlorobutyl)-4-methylpyrimidin-2 (1H)-one (1.25 mmol, 0.25 g) with 2-tert-butyl-4-(piperazin-1-yl)-6-isopropylpyrimidine; yield 0.04 g.

ESI-MS: [M+H$^+$]=427.5, 214.2, 143.2

Example 40

4-(2-tert-Butyl-6-isopropylpyrimidin-4-yl)-1-[4-(5-methyl-2,4-dioxo-3,4-dihydro-2H-pyrimidin-1-yl)-butyl]piperazin-1-ium chloride 0.22 g of the title compound was obtained in analogy to Example 5.2.2 by reacting 1-(4-chlorobutyl)-5-methyl-1H-pyrimidine-2,4-dione (1.00 mmol, 0.22 g) with 2-tert-butyl-4-isopropyl-6-piperazin-1-ylpyrimidine (0.95 mmol, 0.25 g; prepared as described in DE 19735410).

ESI-MS: [M+H$^+$]=443.5, 222.4.

Example 41

1-{4-[4-(2-tert-Butyl-6-propylpyrimidin-4-yl)piperazin-1-yl]butyl}-4-trifluoromethyl-1H-pyrimidin-2-one 0.21 g of the title compound was obtained in analogy to Example 5.2.2 by reacting 1-(4-chlorobutyl)-4-trifluoromethyl-1H-pyrimidin-2-one from Example 15.1 (0.98 mmol, 0.25 g) with 2-tert-butyl-4-piperazin-1-yl-6-propylpyrimidine (0.98 mmol, 0.26 g; prepared as described in DE 19735410).
ESI-MS: [M+H$^+$]=481.4, 241.1.

Example 42

1-{4-[4-(2-tert-Butyl-6-propylpyrimidin-4-yl)piperazin-1-yl]butyl}-3-methyl-1H-pyrimidine-2,4-dione (BSF 4105765, 1044-138)

0.19 g of the title compound was obtained in analogy to Example 5.2.2 by reacting 1-(4-chlorobutyl)-3-methyl-1H-pyrimidine-2,4-dione from Example 27.1 (0.92 mmol, 0.20 g) with 2-tert-butyl-4-piperazin-1-yl-6-propylpyrimidine (0.92 mmol, 0.24 g; prepared as described in DE 19735410).
ESI-MS: [M+H$^+$]=443.4, 222.2.

Example 43

4-(4-Fluorophenyl)-1-[4-(4-methylpiperazin-1-yl)butyl]-1H-pyrimidin-2-one

43.1 2-Chloro-4-(4-fluorophenyl)pyrimidine 6.73 g of 2-chloro-4-(4-fluorophenyl)pyrimidine were obtained in analogy to Example 24.1 from 2,4-dichloropyrimidine (40.00 mmol, 5.96 g) and 4-fluorophenylboronic acid (40.00 mmol, 5.60 g).

43.2 4-(4-Fluorophenyl)pyrimidin-2-ol 6.27 g of 4-(4-fluorophenyl)pyrimidin-2-ol were obtained in analogy to Example 24.2 from 2-chloro-4-(4-fluorophenyl)pyrimidine from Example 43.1 (32.26 mmol, 6.73 g).
ESI-MS: [M+K$^+$]=228.9, [M+H$^+$]=191.1.

43.3 1-(4-Chlorobutyl)-4-(4-fluorophenyl)-1H-pyrimidin-2-one 1.00 g of 1-(4-chlorobutyl)-4-(4-fluorophenyl)-1H-pyrimidin-2-one was obtained in analogy to Example 24.3 by reacting 4-(4-fluorophenyl)pyrimidin-2-ol from Example 43.2 (15.77 mmol, 3.00 g) with 1-bromo-4-chlorobutane.
ESI-MS: 321.0, [M+K$^+$]=319.0, 283.0, [M+H$^+$]=281.0.

43.4 4-(4-Fluorophenyl)-1-[4-(4-methylpiperazin-1-yl)butyl]-1H-pyrimidin-2-one 0.08 g of the title compound was obtained in analogy to Example 5.2.2 by reacting 1-(4-chlorobutyl)-4-(4-fluorophenyl)-1H-pyrimidin-2-one from Example 43.3 (0.61 mmol, 0.17 g) with 1-methylpiperazine (0.57 mmol, 0.06 g).
ESI-MS: 346.1, [M+H$^+$]=345.2, 173.1.

Example 44

1-{4-[4-(2-tert-Butyl-6-propylpyrimidin-4-yl)piperazin-1-yl]butyl}-4-(4-fluorophenyl)-1H-pyrimidin-2-one 0.29 g of the title compound was obtained in analogy to Example 5.2.2 by reacting 1-(4-chlorobutyl)-4-(4-fluorophenyl)-1H-pyrimidin-2-one from Example 43.3 (0.61 mmol, 0.17 g) with 2-tert-butyl-4-piperazin-1-yl-6-propylpyrimidine (0.74 mmol, 0.20 g; prepared as described in DE 19735410)
ESI-MS: [M+H$^+$]=507.4, 254.1. .

Example 45

4-(2-tert-Butyl-6-trifluoromethylpyrimidin-4-yl)-1-{4-[4-(4-fluorophenyl)-2-oxo-2H-pyrimidin-1-yl]butyl}piperazin-1-ium chloride 0.13 g of the title compound was obtained in analogy to Example 5.2.2 by reacting 1-(4-chlorobutyl)-4-(4-fluorophenyl)-1H-pyrimidin-2-one from Example 43.3 (0.40 mmol, 0.11 g) with 2-tert-butyl-4-piperazin-1-yl-6-trifluoromethylpyrimidine (0.38 mmol, 0.11 g; prepared as described in DE 19735410).
ESI-MS: [M+H$^+$]=533.3, 267.1.

Example 46

1-(2E)-{4-[4-(2-tert-Butyl-6-trifluoromethylpyrimidin-4-yl)piperazin-1-yl]-2-methylbut-2-enyl}-1H-pyrimidine-2,4-dione 0.14 g of the title compound was obtained in analogy to Example 5.2.2 by reacting uracil (0.60 mmol, 0.07 g) with 4-(2-tert-butyl-6-trifluoromethylpyrimidin-4-yl)-1-(4-chloro-3-methylbut-2-enyl)piperazin-1-ium chloride (0.60 mmol, 0.26 g, prepared as described in DE 19735410).
ESI-MS: [M+H$^+$]=467.3, 234.1;

Example 47

1-{4-[4-(2-tert-Butyl-6-propylpyrimidin-4-yl)piperazin-1-yl]butyl}-2,4-dioxo-1,2,3,4-tetrahydropyrimidine-5-carbonitrile 27.0 mg of the title compound were obtained in analogy to Example 5.2.2 by reacting 1-(4-chlorobutyl)-2,4-dioxo-1,2,3,4-tetrahydropyrimidine-5-carbonitrile from Example 18.1 (0.31 mmol, 0.07 g) with 2-tert-butyl-4-piperazin-1-yl-6-propylpyrimidine (0.31 mmol, 0.08 g; prepared as described in DE 19735410).
ESI-MS: 455.3, [M+H$^+$]=454.2, 227.6.

Example 48

4-Azetidin-1-yl-1-{4-[4-(2-tert-butyl-6-trifluoromethylpyrimidin-4-yl)piperazin-1-yl]butyl}-5-methyl-1H-pyrimidin-2-one A mixture of 1-{4-[4-(2-tert-butyl-6-trifluoromethylpyrimidin-4-yl)piperazin-1-yl]butyl}-5-methyl-4-thioxo-3,4-dihydro-1H-pyrimidin-2-one from Example 2 (0.24 mmol, 0.12 g) and azetidine (5.81 mmol, 0.33 g) in ethanol (1.9 ml) was stirred at 60° C. in a microwave (Milestone Ethos 1600) for 1 hour. The reaction mixture was then concentrated and the resulting residue was purified by column chromatography on silica gel (eluent: CH$_2$Cl$_2$/methanol 95/5), resulting in 0.08 g of the title compound.
ESI-MS: 509.2, [M+H$^+$]=508.3, 254.6.

Example 49

1-{4-[4-(2-tert-Butyl-6-propylpyrimidin-4-yl)piperazin-1-yl]butyl}-4-phenyl-1H-pyrimidin-2-one 0.30 g of the title compound was obtained in analogy to Example 5.2.2 by reacting 1-(4-chlorobutyl)-4-phenylpyrimidin-2(1H)-one from Example 24.3 (1.13 mmol, 0.3 g) with 2-tert-butyl-4-piperazin-1-yl-6-propylpyrimidine (1.13 mmol, 0.3 g; prepared as described in DE 19735410).
ESI-MS: 490.4, 489.4, 245.1.

Example 50

1-{4-[4-(2-tert-Butyl-6-propylpyrimidin-4-yl)piperazin-1-yl]butyl}-4-furan-2-yl-1H-pyrimidin-2-one 50.1 2-Chloro-4-furan-2-ylpyrimidine 3.87 g of 2-chloro-4-furan-2-ylpyrimidine were obtained in analogy to Example 24.1 by reacting 2,4-dichloropyrimidine (33.56 mmol, 5.00 g) with furan-2-boronic acid (33.56 mmol, 3.76 g).
ESI-MS: 183.1, [M+H$^+$]=181.1.

50.2 4-Furan-2-ylpyrimidin-2-ol 4.16 g of 4-furan-2-ylpyrimidin-2-ol were obtained in analogy to Example 24.2 from 2-chloro-4-furan-2-ylpyrimidine from Example 50.1 (21.43 mmol, 3.87 g).
ESI-MS: [2M+Na$^+$]=347.0, [M+H$^+$]=163.1.

50.3 1-(4-Chlorobutyl)-4-furan-2-yl-1H-pyrimidin-2-one 0.61 g of 1-(4-chlorobutyl)-4-furan-2-yl-1H-pyrimidin-2-one was obtained in analogy to Example 24.3 from 4-furan-2-ylpyrimidin-2-ol from Example 50.2 (12.83 mmol, 2.08 g).
ESI-MS: 255.1, [M+H$^+$]=253.1.

50.4 1-{4-[4-(2-tert-Butyl-6-propylpyrimidin-4-yl)piperazin-1-yl]butyl}-4-furan-2-yl-1H-pyrimidin-2-one 0.14 g of the title compound was obtained in analogy to Example 5.2.2 by reacting 1-(4-chlorobutyl)-4-furan-2-yl-1H-pyrimidin-2-one from Example 50.3 (1.19 mmol, 0.30 g) with 2-tert-butyl-4-piperazin-1-yl-6-propylpyrimidine (1.19 mmol, 0.31 g; prepared as described in DE 19735410).
ESI-MS: [M+H$^+$]=479.4, 240.1.

Example 51

1-{4-[4-(2-tert-Butyl-6-trifluoromethylpyrimidin-4-yl)piperazin-1-yl]butyl}-4-furan-2-yl-1H-pyrimidin-2-one 0.29 g of the title compound was obtained in analogy to Example 5.2.2 by reacting 1-(4-chlorobutyl)-4-furan-2-yl-1H-pyrimidin-2-one from Example 50.3 (1.19 mmol, 0.30 g) with 2-tert-butyl-4-piperazin-1-yl-6-trifluoromethylpyrimidine (1.18 mmol, 0.34 g; prepared as described in DE 19735410).
ESI-MS: 506.2, [M+H$^+$]=505.2, 253.1.

Example 52

1-{4-[4-(2-tert-Butyl-6-trifluoromethylpyrimidin-4-yl)piperazin-1-yl]butyl}-5-chloro-1H-pyrimidine-2,4-dione 52.1 5-Chloro-1-(4-chlorobutyl)-1H-pyrimidine-2,4-dione 1.75 g of the title compound were obtained in analogy to Example 18.1 from 5-chlorouracil (34.12 mmol, 5.00 g) and 1-bromo-4-chlorobutane.
ESI-MS: 239.1, [M+H$^+$]=237.1.

52.2 1-{4-[4-(2-tert-Butyl-6-trifluoromethylpyrimidin-4-yl)piperazin-1-yl]butyl}-5-chloro-1H-pyrimidine-2,4-dione 0.10 g of the title compound was obtained in analogy to Example 5.2.2 by reacting 5-chloro-1-(4-chlorobutyl)-1H-pyrimidine-2,4-dione from Example 52.1 (0.84 mmol, 0.20 g) with 2-tert-butyl-4-piperazin-1-yl-6-trifluoromethylpyrimidine (0.85 mmol, 0.25 g; prepared as described in DE 19735410).
ESI-MS: 492.3, [M+H$^+$]=489.2, 245.1.

Example 53

1-{4-[4-(2-tert-Butyl-6-propylpyrimidin-4-yl)piperazin-1-yl]butyl}-5-fluoro-1H-pyrimidine-2,4-dione 0.50 g of the title compound was obtained in analogy to Example 5.2.2 by reacting 1-(4-chlorobutyl)-5-fluoro-1H-pyrimidine-2,4-dione from Example 16.1 (2.27 mmol, 0.50 g) with 2-tert-butyl-4-piperazin-1-yl-6-propylpyrimidine (2.27 mmol, 0.60 g; prepared as described in DE 19735410).
$^1$H NMR (400 MHz, DMSO-d$_6$) δ (ppm: 8.08 (1H, d), 6.41 (1H, s), 3.63 (2H, t), 3.56 (4H, s br.), 2.46 (2H, t), 2.38 (4H, s br.), 2.30 (2H, t), 1.60 (4H, m), 1.43 (2H, m), 1.24 (9H, s), 0.89 (3H, t).

Example 54

1-{4-[4-(2-tert-Butyl-6-trifluoromethylpyrimidin-4-yl)piperazin-1-yl]pentyl}-5-methyl-1H-pyrimidine-2,4-dione 0.29 g of the title compound was obtained in analogy to Example 5.2.2 by reacting 1-(4-bromopentyl)-5-methyl-1H-pyrimidine-2,4-dione (1.82 mmol, 0.50 g; prepared in analogy to Example 6.2 from thymine and 1,4-dibromopentane) with 2-tert-butyl-4-piperazin-1-yl-6-trifluoromethylpyrimidine (1.73 mmol, 0.50 g; prepared as described in DE 19735410).
ESI-MS: 484.2, [M+H$^+$]=483.3, 242.1.

Example 55

1-{4-[4-(2-tert-Butyl-6-trifluoromethylpyrimidin-4-yl)piperazin-1-yl]butyl}-5-trifluoromethyl-1H-pyrimidine-2,4-dione 55.1 1-(4-Chlorobutyl)-5-trifluoromethyl-1H-pyrimidine-2,4-dione 0.42 g of 1-(4-chlorobutyl)-5-trifluoromethyl-1H-pyrimidine-2,4-dione was obtained in analogy to Example 18.1 by reacting 5-trifluoromethyl-1H-pyrimidine-2,4-dione (5.28 mmol, 0.98 g) with 1-bromo-4-chlorobutane.
ESI-MS: 311.0, [M+K$^+$]=309.0, 273.0, [M+H$^+$]=271.0.

55.2 1-{4-[4-(2-tert-Butyl-6-trifluoromethylpyrimidin-4-yl)piperazin-1-yl]butyl}-5-trifluoromethyl-1H-pyrimidine-2,4-dione 75.0 mg of the title compound were obtained in analogy to Example 5.2.2 by reacting 1-(4-chlorobutyl)-5-trifluoromethyl-1H-pyrimidine-2,4-dione from Example 55.1 (0.55 mmol, 0.15 g) with 2-tert-butyl-4-piperazin-1-yl-6-trifluoromethylpyrimidine (0.53 mmol, 0.15 g; prepared as described in DE 19735410).

ESI-MS: 524.3, [M+H$^+$]=523.2, 262.1.

Example 56

1-{4-[4-(2-tert-Butyl-6-propylpyrimidin-4-yl)piperazin-1-yl]butyl}-5-trifluoromethyl-1H-pyrimidine-2,4-dione 40.0 mg of the title compound were obtained in analogy to Example 5.2.2 by reacting 1-(4-chlorobutyl)-5-trifluoromethyl-1H-pyrimidine-2,4-dione from Example 55.1 (0.55 mmol, 0.15 g) with 2-tert-butyl-4-piperazin-1-yl-6-propylpyrimidine (0.53 mmol, 0.14 g; prepared as described in DE 19735410).

ESI-MS: 498.2, [M+H$^+$]=497.2, 249.1.

Example 57

4-(2-tert-Butyl-6-propylpyrimidin-4-yl)-1-[4-(2-oxo-4-(o-tolyl)-2H-pyrimidin-1-yl)butyl]-piperazin-1-ium fumarate 57.1 2-Chloro-4-(o-tolyl)pyrimidine 3.10 g of 2-chloro-4-(o-tolyl)pyrimidine were obtained in analogy to Example 24.1 from 2,4-dichloropyrimidine (13.42 mmol, 2.00 g) and o-tolueneboronic acid (13.42 mmol, 1.83 g).

57.2 4-(o-Tolyl)-1H-pyrimidin-2-one 50.0 mg of 4-(o-tolyl)-1H-pyrimidin-2-one were obtained in analogy to Example 24.2 by use of 2-chloro-4-(o-tolyl)pyrimidine from Example 57.1 (0.49 mmol, 0.10 g).

ESI-MS: [M+H$^+$]=187.1.

57.3 1-(4-Chlorobutyl)-4-(o-tolyl)-1H-pyrimidin-2-one 1.54 g of 1-(4-chlorobutyl)-4-(o-tolyl)-1H-pyrimidin-2-one were obtained in analogy to Example 24.3 by reacting 4-(o-tolyl)-1H-pyrimidin-2-one (7.30 mmol, 1.36 g) with 1-bromo-4-chlorobutane.

ESI-MS: 279.0, [M+H$^+$]=277.0.

57.4 4-(2-tert-Butyl-6-propylpyrimidin-4-yl)-1-[4-(2-oxo-4-(o-tolyl)-2H-pyrimidin-1-yl)butyl]piperazin-1-ium fumarate 0.15 g of the title compound was obtained in analogy to Example 5.2.2 by reacting 1-(4-chlorobutyl)-4-(o-tolyl)-1H-pyrimidin-2-one from Example 57.3 (0.72 mmol, 0.20 g) with 2-tert-butyl-4-piperazin-1-yl-6-propylpyrimidine (0.69 mmol, 0.18 g; prepared as described in DE 19735410).

ESI-MS: [M+H$^+$]=503.4, 252.1.

Example 58

1-{4-[4-(2-tert-Butyl-6-trifluoromethylpyrimidin-4-yl)piperazin-1-yl]butyl}-4-(m-tolyl)-1H-pyrimidin-2-one 58.1 2-Chloro-4-(m-tolyl)pyrimidine 4.70 g of 2-chloro-4-(m-tolyl)pyrimidine were obtained in analogy to Example 24.1 by reacting 2,4-dichloropyrimidine (20.14 mmol, 3.00 g) with 4-m-tolylboronic acid (20.14 mmol, 2.74 g).

58.2 4-(m-Tolyl)-1H-pyrimidin-2-one 1.34 g of 4-(m-tolyl)-1H-pyrimidin-2-one were obtained in analogy to Example 24.2 starting from 2-chloro-4-(m-tolyl)pyrimidine from Example 58.1 (14.66 mmol, 3.00 g).

ESI-MS: [M+H$^+$]=187.1.

58.3 1-(4-Chlorobutyl)-4-(m-tolyl)-1H-pyrimidin-2-one 1.17 g of the title compound were obtained in analogy to Example 24.3 by reacting 4-(m-tolyl)-1H-pyrimidin-2-one (6.98 mmol, 1.30 g) with 1-bromo-4-chlorobutane.

ESI-MS: 279.0, [M+H$^+$]=277.0;

58.4 1-{4-[4-(2-tert-Butyl-6-trifluoromethylpyrimidin-4-yl)piperazin-1-yl]butyl}-4-(m-tolyl)-1H-pyrimidin-2-one 0.12 g of the title compound was obtained in analogy to Example 5.2.2 by reacting 1-(4-chlorobutyl)-4-(m-tolyl)-1H-pyrimidin-2-one from Example 58.3 (0.54 mmol, 0.15 g) with 2-tert-butyl-4-piperazin-1-yl-6-trifluoromethylpyrimidine (0.40 mmol, 0.14 g; prepared as described in DE 19735410).

ESI-MS: 530.3, [M+H$^+$]=529.3, 265.1.

Example 59

1-{4-[4-(2-tert-Butyl-6-propylpyrimidin-4-yl)piperazin-1-yl]butyl}-4-(m-tolyl)-1H-pyrimidin-2-one 0.15 g of 1-{4-[4-(2-tert-butyl-6-propylpyrimidin-4-yl)piperazin-1-yl]butyl}-4-(m-tolyl)-1H-pyrimidin-2-one was obtained in analogy to Example 5.2.2 by reacting 1-(4-chlorobutyl)-4-(m-tolyl)-1H-pyrimidin-2-one from Example 58.3 (0.54 mmol, 0.15 g) with 2-tert-butyl-4-piperazin-1-yl-6-propylpyrimidine (0.49 mmol, 0.13 g; prepared as described in DE 19735410).

ESI-MS: [M+H$^+$]=503.4, 252.2.

Example 60

4-(2-tert-Butyl-6-trifluoromethylpyrimidin-4-yl)-1-[4-(2-oxo-4-(o-tolyl)-2H-pyrimidin-1-yl)butyl]piperazin-1-ium fumarate 0.21 g of the title compound was obtained in analogy to Example 5.2.2 by reacting 1-(4-chlorobutyl)-4-(o-tolyl)-1H-pyrimidin-2-one from Example 57.3 (0.72 mmol, 0.20 g) with 2-tert-butyl-4-piperazin-1-yl-6-trifluoromethylpyrimidine (0.69 mmol, 0.20 g; prepared as described in DE 19735410)

ESI-MS: [M+H$^+$]=529.3, 265.1..

Example 61

4-(2-tert-Butyl-6-propylpyrimidin-4-yl)-1-[4-(2,4-dioxo-3,4-dihydro-2H-pyrimidin-1-yl)-1-methylbutyl]piperazin-1-ium fumarate

61.1 1-(4-Bromopentyl)-1H-pyrimidine-2,4-dione 1.07 g of the title compound were obtained in analogy to Example 6.2 by reacting uracil (28.55 mmol, 3.20 g) with 1,4-dibromopentane (29.35 mmol, 6.75 g).
ESI-MS: 263.0, [M+H$^+$]=261.0.

61.2 4-(2-tert-Butyl-6-propylpyrimidin-4-yl)-1-[4-(2,4-dioxo-3,4-dihydro-2H-pyrimidin-1-yl)-1-methylbutyl]piperazin-1-ium fumarate 0.10 g of the title compound was obtained in analogy to Example 5.2.2 by reacting 1-(4-bromopentyl)-1H-pyrimidine-2,4-dione from Example 61.1 (1.15 mmol, 0.30 g) with 2-tert-butyl-4-piperazin-1-yl-6-propylpyrimidine (1.09 mmol, 0.29 g; prepared as described in DE 19735410).
ESI-MS: 444.4, [M+H$^+$]=443.4, 222.1.

Example 62

1-{4-[4-(2-tert-Butyl-6-trifluoromethylpyrimidin-4-yl)piperazin-1-yl]pentyl}-1H-pyrimidine-2,4-dione 0.07 g of the title compound was obtained in analogy to Example 5.2.2 by reacting 1-(4-bromopentyl)-1H-pyrimidine-2,4-dione from Example 61.1 (1.15 mmol, 0.30 g) with 2-tert-butyl-4-piperazin-1-yl-6-trifluoromethylpyrimidine (1.09 mmol, 0.31 g; prepared as described in DE 19735410).
ESI-MS: 470.2, [M+H$^+$]=469.2, 235.1.

Example 63

(+)-1-{4-[4-(2-tert-Butyl-6-propylpyrimidin-4-yl)piperazin-1-yl]pentyl}-5-methyl-1H-pyrimidine-2,4-dione For racemate resolution, a solution of 4-(2-tert-butyl-6-propylpyrimidin-4-yl)-1-[1-methyl-4-(5-methyl-2,4-dioxo-3,4-dihydropyrimidin-1 (2H)-yl)butyl]piperazin-1-ium chloride from Example 38 (200 mg) in 3 ml of hexane/isopropanol (9:1 (V/V)) was loaded onto a chiral column (DAICEL ChiralPAK AD, length: 50 cm, internal diameter: 5 cm, particle size: 20µ); eluent: hexane/ethanol/triethylamine (85:15:0.1 (V/V)). 0.08 g of the title compound was obtained after concentration of the resulting filtrate.
ESI-MS: 458.4, [M+H$^+$]=457.4, 229.1;
α (20° C., c=2 mg/ml, CHCl$_3$, l=1 dm): +10°.

Example 64

(−)-1-{4-[4-(2-tert-Butyl-6-trifluoromethylpyrimidin-4-yl)piperazin-1-yl]-2-methylbutyl}-5-methyl-1H-pyrimidine-2,4-dione For racemate resolution, a solution of 1-(4-{4-[2-tert-butyl-6-(trifluoromethyl)pyrimidin-4-yl]piperazin-1-yl}-2-methylbutyl)-5-methylpyrimidine-2,4(1H,3H)-dione (200 mg) from Example 37 in 3 ml of hexane/isopropanol (9:1 (V/V)) was loaded onto an optical column (DAICEL ChiralPAK AD, length: 50 cm, internal diameter: 5 cm, particle size: 20µ, eluent: hexane/ethanol/triethylamine (85:15:0, 1 (V/V)). 0.08 g of the title compound was obtained after concentration of the resulting filtrate.
ESI-MS: [M+H$^+$]=483.3, 242.1;
α (20° C., c=2 mg/ml, CHCl$_3$, l=1 dm): −25.5°.

Example 65

1-(2E)-{4-[4-(2-tert-Butyl-6-trifluoromethylpyrimidin-4-yl)piperazin-1-yl]-2-methylbut-2-enyl}-5-methyl-1H-pyrimidine-2,4-dione 0.16 g of the title compound was obtained in analogy to Example 5.2.2 by reacting 5-methyl-1H-pyrimidine-2,4-dione (0.60 mmol, 0.08 g) and 4-(2-tert-butyl-6-trifluoromethylpyrimidin-4-yl)-1-(4-chloro-3-methylbut-2-enyl)piperazin-1-ium chloride (0.60 mmol, 0.22 g; prepared as described in DE 19735410).
ESI-MS: 456.4, [M+H$^+$]=455.4, 228.1.

Example 66

4-(2-tert-Butyl-6-trifluoromethylpyrimidin-4-yl)-1-[4-(2-oxo-4-(p-tolyl)-2H-pyrimidin-1-yl)butyl]piperazin-1-ium fumarate

66.1 2-Chloro-4-(p-tolyl)pyrimidine 3.19 g of 2-chloro-4-(p-tolyl)pyrimidine were obtained in analogy to Example 24.1 by reacting 2,4-dichloropyrimidine (13.42 mmol, 2.00 g) with p-tolylboronic acid (13.42 mmol, 1.83 g).

66.2 4-(p-Tolyl)-1H-pyrimidin-2-one 1.95 g of the title compound were obtained in analogy to Example 24.2 from 2-chloro-4-(p-tolyl)pyrimidine (15.59 mmol, 3.19 g) from Example 66.1.
ESI-MS: [M+H$^+$]=187.1.

66.3 1-(4-Chlorobutyl)-4-(p-tolyl)-1H-pyrimidin-2-one 2.47 g of 1-(4-chlorobutyl)-4-(p-tolyl)-1H-pyrimidin-2-one were obtained in analogy to Example 24.3 by reacting 4-(p-tolyl)-1H-pyrimidin-2-one from Example 66.2 (10.47 mmol, 1.95 g) with 1-bromo-4-chlorobutane.
ESI-MS: 279.1, [M+H$^+$]=277.0.

66.4 4-(2-tert-Butyl-6-trifluoromethylpyrimidin-4-yl)-1-[4-(2-oxo-4-(p-tolyl)-2H-pyrimidin-1-yl)butyl]piperazin-1-ium fumarate 0.27 g of the title compound was obtained in analogy to Example 5.2.2 by reacting 1-(4-chlorobutyl)-4-(p-tolyl)-1H-pyrimidin-2-one from Example 66.3 (0.90 mmol, 0.25 g) with 2-tert-butyl-4-piperazin-1-yl-6-trifluoromethylpyrimidine (0.81 mmol, 0.23 g; prepared as described in DE 19735410).
ESI-MS: [M+H$^+$]=529.3, 265.1.

Example 67

4-(2-tert-Butyl-6-trifluoromethylpyrimidin-4-yl)-1-{4-[4-(2-fluorophenyl)-2-oxo-2H-pyrimidin-1-yl]butyl}piperazin-1-ium fumarate

67.1 2-Chloro-4-(2-fluorophenyl)pyrimidine 1.10 g of 2-chloro-4-(2-fluorophenyl)pyrimidine were obtained in analogy to Example 24.1 by reacting 2,4-dichloropyrimidine (13.42 mmol, 2.00 g) with 2-fluorophenylboronic acid (13.42 mmol, 1.88 g).
ESI-MS: 211.1, [M+H$^+$]=209.1.

67.2 4-(2-Fluorophenyl)pyrimidin-2-ol 1.10 g of 4-(2-fluorophenyl)pyrimidin-2-ol were obtained in analogy to Example 24.2 from 2-chloro-4-(2-fluorophenyl)pyrimidine from Example 67.1 (5.27 mmol, 1.10 g).
ESI-MS: [M+H$^+$]=191.1.

67.3 1-(4-Chlorobutyl)-4-(2-fluorophenyl)-1H-pyrimidin-2-one 0.48 g of the title compound was obtained in analogy to Example 24.3 by reacting 4-(2-fluorophenyl)pyrimidin-2-ol (5.52 mmol, 1.05 g) from Example 67.2 with 1-bromo-4-chlorobutane.

67.4 4-(2-tert-Butyl-6-trifluoromethylpyrimidin-4-yl)-1-{4-[4-(2-fluorophenyl)-2-oxo-2H-pyrimidin-1-yl]butyl}piperazin-1-ium fumarate 0.33 g of the title compound was obtained in analogy to Example 5.2.2 by reacting 1-(4-chlorobutyl)-4-(2-fluorophenyl)-1H-pyrimidin-2-one from Example 67.3 (0.61 mmol, 0.20 g) with 2-tert-butyl-4-piperazin-1-yl-6-trifluoromethylpyrimidine (0.64 mmol, 0.18 g; prepared as described in DE 19735410).
ESI-MS: 534.2, [M+H$^+$]=533.3, 267.1.

Example 68

(+)-1-{4-[4-(2-tert-Butyl-6-trifluoromethylpyrimidin-4-yl)piperazin-1-yl]-2-methylbutyl}-5-methyl-1H-pyrimidine-2,4-dione For racemate resolution, a solution of 1-(4-{4-[2-tert-butyl-6-(trifluoromethyl)pyrimidin-4-yl]piperazin-1-yl}-2-methylbutyl)-5-methylpyrimidine-2,4(1H,3H)-dione from Example 37 (200 mg) in 1.5 ml of isopropanol, 1.5 ml of hexane and 80 μl of methanol was loaded onto a chiral column (DAICEL ChiralPAK AD, length: 50 cm, internal diameter: 5 cm, particle size: 20μ); eluent: hexane/ethanol/triethylamine (85:15:0.1 (V/V)). 0.08 g of the title compound was obtained after concentration of the resulting filtrate.
ESI-MS: [M+H$^+$]=483.3, 242.1;
α (20° C., c=2 mg/ml, CHCl$_3$, l=1 dm): +17°.

Example 69

1-{4-[4-(2-tert-Butyl-6-propylpyrimidin-4-yl)piperazin-1-yl]butyl}-4-methyl-1H-pyrimidin-2-one 0.23 g of the title compound was obtained in analogy to Example 5.2.2 by reacting 1-(4-chlorobutyl)-4-(2-fluorophenyl)-1H-pyrimidin-2-one from Example 67.3 (0.61 mmol, 0.20 g) with 2-tert-butyl-4-piperazin-1-yl-6-propylpyrimidine (0.64 mmol, 0.17 g; prepared as described in DE 19735410).
ESI-MS: [M+H$^+$]=507.4, 254.1.

Example 70

1-{4-[4-(2-tert-Butyl-6-propylpyrimidin-4-yl)piperazin-1-yl]-2-methylbutyl}-5-methyl-1H-pyrimidine-2,4-dione 7.5 mg of the title compound were obtained in analogy to Example 37 from 1-{4-[4-(2-tert-butyl-6-propylpyrimidin-4-yl)piperazin-1-yl]-2-methylbut-2-enyl}-5-methyl-1H-pyrimidine-2,4-dione from Example 65 (0.06 mmol, 25.0 mg).
ESI-MS: 458.4, [M+H$^+$]=457.4, 229.1.

Example 71

1-{4-[4-(2-tert-Butyl-6-trifluoromethylpyrimidin-4-yl)piperazin-1-yl]butyl}-4-cyclobutyl-1H-pyrimidin-2-one

71.1 1-Cyclobutyl-3,3-dimethoxypropan-1-one 11.00 g of the title compound were obtained in analogy to Helv. Chim. Acta 2002, 85, 2926-29 (Example 6, p. 2928) by reacting 1-cyclobutylethanone (152.83 mmol, 15.00 g) with methyl formate (308.16 mmol, 18.51 g).

71.2 4-Cyclobutyl-1H-pyrimidin-2-one 0.75 g of 4-cyclobutyl-1H-pyrimidin-2-one was obtained in analogy to Example 8.1 by reacting 1-cyclobutyl-3,3-dimethoxypropan-1-one (63.87 mmol, 11.00 g) from Example 71.1 with urea.

71.3 1-(4-Chlorobutyl)-4-cyclobutyl-1H-pyrimidin-2-one 0.38 g of the title compound was obtained in analogy to Example 5.2.1 by reacting 4-cyclobutyl-1H-pyrimidin-2-one from Example 71.2 (4.99 mmol, 0.75 g) with 1-bromo-4-chlorobutane.
ESI-MS: 243.1 [M+H$^+$]=241.1.

71.4 1-{4-[4-(2-tert-Butyl-6-trifluoromethylpyrimidin-4-yl)piperazin-1-yl]butyl}-4-cyclobutyl-1H-pyrimidin-2-one 0.19 g of the title compound was obtained in analogy to Example 5.2.2 by reacting 1-(4-chlorobutyl)-4-cyclobutyl-1H-pyrimidin-2-one from Example 71.3 (0.75 mmol, 0.18 g) with 2-tert-butyl-4-piperazin-1-yl-6-trifluoromethylpyrimidine (0.67 mmol, 0.19 g; prepared as described in DE 19735410).
ESI-MS: [M+H$^+$]=493.4, 247.1.

Example 72

4-(2-tert-Butyl-6-propylpyrimidin-4-yl)-1-{4-[4-(3-fluorophenyl)-2-oxo-2H-pyrimidin-1-yl]butyl}piperazin-1-ium fumarate

72.1 2-Chloro-4-(3-fluorophenyl)pyrimidine 1.00 g of 2-chloro-4-(3-fluorophenyl)pyrimidine was obtained in analogy to Example 24.1 by reacting 2,4-dichloropyrimidine (13.42 mmol, 2.00 g) with 3-fluorophenylboronic acid (13.42 mmol, 1.88 g).
ESI-MS: 210.9, [M+H$^+$]=208.9.

72.2 4-(3-Fluorophenyl)pyrimidin-2-ol 1.06 g of 4-(3-fluorophenyl)pyrimidin-2-ol were obtained in analogy to Example 24.2 from 2-chloro-4-(3-fluorophenyl)pyrimidine from Example 72.1 (4.79 mmol, 1.00 g).
ESI-MS: [M+H$^+$]=191.1.

72.3 1-(4-Chlorobutyl)-4-(3-fluorophenyl)-1H-pyrimidin-2-one 0.34 g of the title compound was obtained in analogy to Example 24.3 by reacting 4-(3-fluorophenyl)pyrimidin-2-ol from Example 72.2 (5.26 mmol, 1.00 g) with 1-bromo-4-chlorobutane.
ESI-MS: 283.0, [M+H$^+$]=281.0.

72.4 4-(2-tert-Butyl-6-propylpyrimidin-4-yl)-1-{4-[4-(3-fluorophenyl)-2-oxo-2H-pyrimidin-1-yl]butyl}piperazin-1-ium fumarate 0.11 g of the title compound was obtained in analogy to Example 5.2.2 by reacting 1-(4-chlorobutyl)-4-(3-fluorophenyl)-1H-pyrimidin-2-one from Example 72.3 (0.61 mmol, 0.17 g) with 2-tert-butyl-4-piperazin-1-yl-6-propylpyrimidine (0.55 mmol, 0.14 g; prepared as described in DE 19735410).
ESI-MS: [M+H$^+$]=507.4, 254.2.

Example 73

4-(2-tert-Butyl-6-trifluoromethylpyrimidin-4-yl)-1-{4-[4-(3-fluorophenyl)-2-oxo-2H-pyrimidin-1-yl]butyl}piperazin-1-ium fumarate 0.16 g of the title compound was obtained in analogy to Example 5.2.2 by reacting 1-(4-chlorobutyl)-4-(3-fluorophenyl)-1H-pyrimidin-2-one from Example 72.3 (0.61 mmol, 0.17 g) with 2-tert-butyl-4-piperazin-1-yl-6-trifluoromethylpyrimidine (0.55 mmol, 0.16 g; prepared as described in DE 19735410).
ESI-MS: [M+Na$^+$]=555.3, 534.3, [M+H$^+$]=533.3, 267.3.

Example 74

1-{4-[4-(2-tert-Butyl-6-propylpyrimidin-4-yl)piperazin-1-yl]butyl}-4-cyclobutyl-1H-pyrimidin-2-one 0.12 g of the title compound was obtained in analogy to Example 5.2.2 by reacting 1-(4-chlorobutyl)-4-cyclobutyl-1H-pyrimidin-2-one from Example 71.3 (0.75 mmol, 0.18 g) with 2-tert-butyl-4-piperazin-1-yl-6-propylpyrimidine (0.67 mmol, 0.18 g; prepared as described in DE 19735410).
ESI-MS: [M+H$^+$]=467.4, 234.1.

Example 75

4-(2-tert-Butyl-6-propylpyrimidin-4-yl)-1-[4-(2-oxo-4-(p-tolyl)-2H-pyrimidin-1-yl)butyl]piperazine 1-fumarate 0.18 g of the title compound was obtained in analogy to Example 5.2.2 by reacting 1-(4-chlorobutyl)-4-(p-tolyl)-1H-pyrimidin-2-one from Example 66.3 (0.90 mmol, 0.25 g) with 2-tert-butyl-4-piperazin-1-yl-6-propylpyrimidine (0.81 mmol, 0.21 g; prepared as described in DE 19735410).
ESI-MS: [M+H$^+$]=503.4, 252.1.

Example 76

(−)-1-{4-[4-(2-tert-Butyl-6-propylpyrimidin-4-yl)piperazin-1-yl]pentyl}-5-methyl-1H-pyrimidine-2,4-dione For racemate resolution, a solution of 4-(2-tert-butyl-6-propylpyrimidin-4-yl)-1-[1-methyl-4-(5-methyl-2,4-dioxo-3,4-dihydropyrimidin-1(2H)-yl)butyl]piperazin-1-ium chloride from Example 38 (200 mg) in 3 ml of hexane/isopropanol (9:1 (V/V)) was loaded onto a chiral column (DAICEL ChiralPAK AD, length: 50 cm, internal diameter: 5 cm, particle size: 20μ); eluent: hexane/ethanol/triethylamine (85:15: 0.1 (V/V)). 0.08 g of the title compound was obtained after concentration of the resulting filtrate.
ESI-MS: 458.4, [M+H$^+$]=457.4, 229.1;
α (20° C., c=2 mg/ml, CHCl$_3$, l=1 dm): −22°.

Example 77

4-(2-tert-Butyl-6-propylpyrimidin-4-yl)-1-[4-(5-chloro-2,4-dioxo-3,4-dihydro-2H-pyrimidin-1-yl)butyl]piperazin-1-ium acetate 65.0 mg of the title compound were obtained in analogy to Example 5.2.2 by reacting 5-chloro-1-(4-chlorobutyl)-1H-pyrimidine-2,4-dione from Example 52.1 (0.83 mmol, 0.20 g) with 2-tert-butyl-4-piperazin-1-yl-6-propylpyrimidine (0.86 mmol, 0.23 g; prepared as described in DE 19735410).
$^1$H NMR (400 MHz, DMSO-d$_6$) δ (ppm): 8.16 (1H, s), 6.43 (1H, s), 3.69 (2H, t), 3.57 (4H, s br.), 2.46 (2H, t), 2.39 (4H, s br.), 2.30 (2H, t), 1.64 (4H, m), 1.44 (2H, quint.), 1.27 (9H, s), 0.88 (3H, t).

Example 78

1-{4-[4-(2,3-Dichlorophenyl)piperazin-1-yl]butyl}-1H-pyrimidine-2,4-dione 0.21 g of the title compound was obtained in analogy to Example 5.2.2 by reacting 1-(4-chlorobutyl)-1H-pyrimidine-2,4-dione (prepared as described in J. Am. Chem. Soc. 1993, 115, 7636) (0.74 mmol, 0.15 g) with 1-(2,3-dichlorophenyl)piperazine (0.66 mmol, 0.15 g).
ESI-MS: 399.0, [M+H$^+$]=397.0.

Example 79

1-{4-[4-(2,3-Dichlorophenyl)piperazin-1-yl]butyl}-5-fluoro-1H-pyrimidine-2,4-dione 0.21 g of the title compound was obtained in analogy to Example 5.2.2 by reacting 1-(4-chlorobutyl)-5-fluoro-1H-pyrimidine-2,4-dione from Example 16.1 (0.91 mmol, 0.20 g) with 1-(2,3-dichlorophenyl)piperazine (0.82 mmol, 0.19 g).
ESI-MS: 417.3, [M+H$^+$]=415.3.

Example 80

1-{4-[4-(2,3-Dichlorophenyl)piperazin-1-yl]butyl}-4-methyl-1H-pyrimidin-2-one 70.0 mg of the title compound were obtained in analogy to Example 5.2.2 by reacting 1-(4-chlorobutyl)-4-methyl-1H- pyrimidin-2-one from Example 8.2 (0.37 mmol, 75.0 mg) with 1-(2,3-dichlorophenyl)piperazine (0.34 mmol, 77.73 mg).
ESI-MS: 397.1, 395.1.

Example 81

4-(2,3-Dichlorophenyl)-1-[4-(2-oxo-4-phenyl-2H-pyrimidin-1-yl)butyl]piperazin-1-ium fumarate 0.16 g of the title compound was obtained in analogy to Example 5.2.2 by reacting 1-(4-chlorobutyl)-4-phenyl-1H-pyrimidin-2-one from Example 24.3 (0.76 mmol, 0.20 g) with 1-(2,3-dichlorophenyl)piperazine (0.69 mmol, 0.16 g).
ESI-MS: 459.0, [M+H$^+$]=458.1, 457.1, 229.1.

Example 82

1-{4-[4-(2,3-Dichlorophenyl)piperazin-1-yl]butyl}-5-methyl-1H-pyrimidine-2,4-dione 0.17 g of the title compound was obtained in analogy to Example 5.2.2 by reacting 1-(4-chlorobutyl)-5-methyl-1H-pyrimidine-2,4-dione from Example 5.2.1 (0.69 mmol, 0.15 g) with 1-(2,3-dichlorophenyl)piperazine (0.62 mmol, 0.14 g).
ESI-MS: 427.15, 425.15.

Example 83

4-(2-tert-Butyl-6-trifluoromethylpyrimidin-4-yl)-1-[4-(5-ethyl-2,4-dioxo-3,4-dihydro-2H-pyrimidin-1-yl)butyl]piperazine 1-fumarate

83.1
1-(4-Chlorobutyl)-5-ethyl-1H-pyrimidine-2,4-dione 0.21 g of 1-(4-chlorobutyl)-5-ethyl-1H-pyrimidine-2,4-dione was obtained in analogy to Example 18.1 by reacting 5-ethyl-1H-pyrimidine-2,4-dione (6.42 mmol, 0.90 g) with 1-bromo-4-chlorobutane.
ESI-MS: 233.1, [M+H$^+$]=231.1.

83.2 4-(2-tert-Butyl-6-trifluoromethylpyrimidin-4-yl)-1-[4-(5-ethyl-2,4-dioxo-3,4-dihydro-2H-pyrimidin-1-yl)butyl]piperazine 1-fumarate 0.14 g of the title compound was obtained in analogy to Example 5.2.2 by reacting 1-(4-chlorobutyl)-5-ethyl-1H-pyrimidine-2,4-dione from Example 83.1 (0.35 mmol, 0.08 g) with 2-tert-butyl-4-piperazin-1-yl-6-trifluoromethylpyrimidine (0.36 mmol, 0.11 g; prepared as described in DE 19735410).
ESI-MS: 484.2, [M+H$^+$]=483.3, 242.1.

Example 84

4-(2-tert-Butyl-6-propylpyrimidin-4-yl)-1-[4-(5-ethyl-2,4-dioxo-3,4-dihydro-2H-pyrimidin-1-yl)butyl]piperazin-1-ium fumarate 0.07 g of the title compound was obtained in analogy to Example 5.2.2 by reacting 1-(4-chlorobutyl)-5-ethyl-1H-pyrimidine-2,4-dione from Example 83.1 (0.35 mmol, 0.08 g) with 2-tert-butyl-4-piperazin-1-yl-6-propylpyrimidine (0.36 mmol, 0.10 g; prepared as described in DE 19735410)
ESI-MS: 458.4, [M+H$^+$]=457.4, 229.1..

Example 85

4-(2-tert-Butyl-6-trifluoromethylpyrimidin-4-yl)-1-[4-(4-ethoxy-2-oxo-2H-pyrimidin-1-yl)butyl]piperazin-1-ium fumarate

85.1
1-(4-Chlorobutyl)-4-ethoxy-1H-pyrimidin-2-one 0.21 g of 1-(4-chlorobutyl)-4-ethoxy-1H-pyrimidin-2-one was obtained in analogy to Example 5.2.1 by reacting 4-ethoxy-1H-pyrimidin-2-one (4.17 mmol, 0.59 g) with 1-bromo-4-chlorobutane.
ESI-MS: [M+K$^+$]=269.0, 233.1, 232.1, [M+H$^+$]=231.1.

85.2 4-(2-tert-Butyl-6-trifluoromethylpyrimidin-4-yl)-1-[4-(4-ethoxy-2-oxo-2H-pyrimidin-1-yl)butyl]piperazin-1-ium fumarate 0.13 g of the title compound was obtained in analogy to Example 5.2.2 by reacting 1-(4-chlorobutyl)-4-ethoxy-1H-pyrimidin-2-one from Example 85.1 (0.56 mmol, 0.13 g) with 2-tert-butyl-4-piperazin-1-yl-6-trifluoromethylpyrimidine (0.57 mmol, 0.17 g; prepared as described in DE 19735410).
ESI-MS: [M+K$^+$]=521.3, [M+H$^+$]=484.2, 483.3.

Example 86

4-(2-tert-Butyl-6-propylpyrimidin-4-yl)-1-[4-(4-ethoxy-2-oxo-2H-pyrimidin-1-yl)butyl]piperazin-1-ium fumarate 0.14 g of the title compound was obtained in analogy to Example 5.2.2 by reacting 1-(4-chlorobutyl)-4-ethoxy-1H-pyrimidin-2-one from Example 85.1 (0.56 mmol, 0.13 g) with 2-tert-butyl-4-piperazin-1-yl-6-propylpyrimidine (0.57 mmol, 0.15 g; prepared as described in DE 19735410).
ESI-MS: [M+Na$^+$]=495.2, 459.4, 458.4, [M+H$^+$]=457.4.

Example 87

1-{4-[4-(2-tert-Butyl-6-propylpyrimidin-4-yl)piperazin-1-yl]butyl}-4-thiophen-2-yl-1H-pyrimidin-2-one

87.1 2-Chloro-4-thiophen-2-ylpyrimidine 5.16 g of 2-chloro-4-thiophen-2-ylpyrimidine were obtained in analogy to Example 24.1 by reacting 2,4-dichloropyrimidine (33.56 mmol, 5.00 g) with thiophene-2-boronic acid (33.56 mmol, 4.29 g).
ESI-MS: 198.9, [M+H$^+$]=196.9.

87.2 4-Thiophen-2-ylpyrimidin-2-ol 5.40 g of 4-thiophen-2-ylpyrimidin-2-ol were obtained in analogy to Example 24.2 from 2-chloro-4-thiophen-2-ylpyrimidine from Example 87.1 (26.24 mmol, 5.16 g).
ESI-MS: [M+H$^+$]=179.1.

87.3 1-(4-Chlorobutyl)-4-thiophen-2-yl-1H-pyrimidin-2-one 4.48 g of 1-(4-chlorobutyl)-4-thiophen-2-yl-1H-pyrimidin-2-one were obtained in analogy to Example 24.3 by reacting 4-thiophen-2-ylpyrimidin-2-ol from Example 87.2 (16.83 mmol, 3.00 g) with 1-bromo-4-chlorobutane.

ESI-MS: 271.0, [M+H$^+$]=269.0.

87.4 1-{4-[4-(2-tert-Butyl-6-propylpyrimidin-4-yl)piperazin-1-yl]butyl}-4-thiophen-2-yl-1H-pyrimidin-2-one 0.21 g of the title compound was obtained in analogy to Example 5.2.2 by reacting 1-(4-chlorobutyl)-4-thiophen-2-yl-1H-pyrimidin-2-one from Example 87.3 (1.86 mmol, 0.50 g) with 2-tert-butyl-4-piperazin-1-yl-6-propylpyrimidine (1.87 mmol, 0.49 g; prepared as described in DE 19735410).

$^1$H NMR (400 MHz, DMSO-d$_6$) δ (ppm: 8.22 (1H, d), 8.04 (1H, d), 7.88 (1H, d), 7.24 (1H, t), 7.01 (1H, d), 6.41 (1H, s), 3.87 (2H, t), 3.57 (4H, s br.), 2.45 (2H, t), 2.39 (4H, s br.), 2.34 (2H, t), 1.76-1.55 (4H, m), 1.46 (2H, quint.), 1.25 (9H, s), 0.89 (3H, t).

Example 88

1-{4-[4-(2-tert-Butyl-6-trifluoromethylpyrimidin-4-yl)piperazin-1-yl]butyl}-4-thiophen-2-yl-1H-pyrimidin-2-one 0.21 g of the title compound was obtained in analogy to Example 5.2.2 by reacting 1-(4-chlorobutyl)-4-thiophen-2-yl-1H-pyrimidin-2-one from Example 87.3 (1.86 mmol, 0.50 g) with 2-tert-butyl-4-piperazin-1-yl-6-trifluoromethylpyrimidine (1.87 mmol, 0.54 g; prepared as described in DE 19735410).

$^1$H NMR (400 MHz, DMSO-d$_6$) δ (ppm: 8.23 (1H, d), 8.03 (1H, s), 7.88 (1H, d), 7.23 (1H, s), 7.02 (2H, s), 3.87 (2H, t), 3.70 (4H, s br.), 2.41 (4H, s br.), 2.33 (2H, t), 1.74 (2H, quint.), 1.44 (2H, quint.), 1.28 (9H, s).

Example 89

1-[4-(4-Azetidin-1-yl-2-oxo-2H-pyrimidin-1-yl)butyl]-4-(2-tert-butyl-6-trifluoromethylpyrimidin-4-yl)piperazin-1-ium fumarate

89.1 1-{4-[4-(2-tert-Butyl-6-trifluoromethylpyrimidin-4-yl)piperazin-1-yl]butyl}-4-thioxo-3,4-dihydro-1H-pyrimidin-2-one The title compound was obtained in the manner described in J. Med. Chem. 1984, 27, 1470-80, p. 1478, Example 8b, starting from 1-(4-{4-[2-tert-butyl-6-(trifluoromethyl)-pyrimidin-4-yl]piperazin-1-yl}butyl)-4-hydroxypyrimidin-2(1H)-one from Example 13.

89.2 1-[4-(4-Azetidin-1-yl-2-oxo-2H-pyrimidin-1-yl)butyl]-4-(2-tert-butyl-6-trifluoromethylpyrimidin-4-yl)piperazin-1-ium fumarate 0.07 g of the title compound was obtained in analogy to Example 48 by reacting 1-{4-[4-(2-tert-butyl-6-trifluoromethylpyrimidin-4-yl)piperazin-1-yl]butyl}-4-thioxo-3,4-dihydro-1H-pyrimidin-2-one (0.21 mmol, 0.12 g) with azetidine (5.25 mmol, 0.30 g).

ESI-MS: [M+K$^+$]=532.3, 495.2, [M+H$^+$]=494.2.

Example 90

4-(2-tert-Butyl-6-trifluoromethylpyrimidin-4-yl)-1-[4-(2-oxo-4-pyrrolidin-1-yl-2H-pyrimidin-1-yl)butyl]piperazin-1-ium fumarate 0.05 g of the title compound was obtained in analogy to 48 by reacting 1-{4-[4-(2-tert-butyl-6-trifluoromethylpyrimidin-4-yl)piperazin-1-yl]butyl}-4-thioxo-3,4-dihydro-1H-pyrimidin-2-one from Example 89.1 (0.21 mmol, 0.12 g) with pyrrolidine (5.20 mmol, 0.37 g).

ESI-MS: [M+H$^+$]=508.3, 254.6.

Example 91

4-(2-tert-Butyl-6-trifluoromethylpyrimidin-4-yl)-1-[4-(2-oxo-4-piperidin-1-yl-2H-pyrimidin-1-yl)butyl]piperazin-1-ium fumarate 0.06 g of the title compound was obtained in analogy to Example 48 by reacting 1-{4-[4-(2-tert-butyl-6-trifluoromethylpyrimidin-4-yl)piperazin-1-yl]butyl}-4-thioxo-3,4-dihydro-1H-pyrimidin-2-one (0.21 mmol, 0.12 g) with piperidine (5.05 mmol, 0.43 g).

ESI-MS: [M+Na$^+$]=544.3, 523.3, [M+H$^+$]=522.3, 261.6.

Example 92

4-(2-tert-Butyl-6-trifluoromethylpyrimidin-4-yl)-1-[4-(2-oxo-4-thiophen-3-yl-2H-pyrimidin-1-yl)butyl]piperazin-1-ium fumarate

92.1 2-Chloro-4-thiophen-3-ylpyrimidine 1.25 g of 2-chloro-4-thiophen-3-ylpyrimidine were obtained in analogy to Example 24.1 by reacting 2,4-dichloropyrimidine (7.82 mmol, 1.16 g) with thiophene-3-boronic acid (7.82 mmol, 1.00 g).

ESI-MS: [M+H$^+$]=196.9.

92.2 4-Thiophen-3-yl-1H-pyrimidin-2-one 1.30 g of 4-thiophen-3-yl-1H-pyrimidin-2-one were obtained in analogy to Example 24.2 from 2-chloro-4-thiophen-3-ylpyrimidine from Example 92.1 (5.26 mmol, 1.15 g).

ESI-MS: [M+H$^+$]=179.1.

92.3 1-(4-Chlorobutyl)-4-thiophen-3-yl-1H-pyrimidin-2-one 0.25 g of 1-(4-chlorobutyl)-4-thiophen-3-yl-1H-pyrimidin-2-one was obtained in analogy to Example 24.3 by reacting 4-thiophen-3-yl-1H-pyrimidin-2-one from Example 92.2 (5.81 mmol, 1.15 g) with 1-bromo-4-chlorobutane.

ESI-MS: [M+H$^+$]=269.0.

92.4 4-(2-tert-Butyl-6-trifluoromethylpyrimidin-4-yl)-1-[4-(2-oxo-4-thiophen-3-yl-2H-pyrimidin-1-yl)butyl]piperazin-1-ium fumarate 0.12 g of the title compound was obtained in analogy to Example 5.2.2 by reacting 1-(4-chlorobutyl)-4-thiophen-3-yl-1H-pyrimidin-2-one from Example 92.3 (0.37 mmol, 0.11 g) with 2-tert-butyl-4-piperazin-1-yl-6-trifluoromethylpyrimidine (0.38 mmol, 0.11 g; prepared as described in DE 19735410).

ESI-MS: 522.2, [M+H$^+$]=521.3, 261.1.

Example 93

1-{4-[4-(2-tert-Butyl-6-propylpyrimidin-4-yl)piper-azin-1-yl]butyl}-4-thiophen-3-yl-1H-pyrimidin-2-one 0.08 g of the title compound was obtained in analogy to Example 5.2.2 by reacting 1-(4-chlorobutyl)-4-thiophen-3-yl-1H-pyrimidin-2-one from Example 92.3 (0.40 mmol, 0.12 g) with 2-tert-butyl-4-piperazin-1-yl-6-propylpyrimidine (0.42 mmol, 0.11 g; prepared as described in DE 19735410).
ESI-MS: [M+H$^+$]=495.4, 248.1.

Example 94

4-(2-tert-Butyl-6-trifluoromethylpyrimidin-4-yl)-1-[4-(4-cyclopropyl-2-oxo-2H-pyrimidin-1-yl)butyl]piperazin-1-ium acetate

94.1 1-Cyclopropyl-3,3-dimethoxypropan-1-one 6.50 g of 1-cyclopropyl-3,3-dimethoxypropan-1-one were obtained in analogy to Helv. Chim. Acta 2002, 85, 2926-29 (Example 6, p. 2928) by reacting 1-cyclopropyl methyl ketone (149.79 mmol, 12.60 g) with methyl formate (300.0 mmol, 18.02 g).

94.2 4-Cyclopropyl-1H-pyrimidin-2-one 0.11 g of 4-cyclopropyl-1H-pyrimidin-2-one was obtained in analogy to Example 8.1 from 1-cyclopropyl-3,3-dimethoxypropan-1-one from Example 94.1 (12.64 mmol, 2.00 g) with urea.

94.3 1-(4-Chlorobutyl)-4-cyclopropyl-1H-pyrimidin-2-one 0.05 g of 1-(4-chlorobutyl)-4-cyclopropyl-1H-pyrimidin-2-one was obtained in analogy to Example 5.2.1 by reacting 4-cyclopropyl-1H-pyrimidin-2-one from Example 94.2 (0.81 mmol, 0.11 g) with 1-bromo-4-chlorobutane.

94.4 4-(2-tert-Butyl-6-trifluoromethylpyrimidin-4-yl)-1-[4-(4-cyclopropyl-2-oxo-2H-pyrimidin-1-yl)butyl]piperazin-1-ium acetate 0.02 g of the title compound was obtained in analogy to Example 5.2.2 by reacting 1-(4-chlorobutyl)-4-cyclopropyl-1H-pyrimidin-2-one (0.22 mmol, 50.0 mg) with 2-tert-butyl-4-piperazin-1-yl-6-trifluoromethylpyrimidine (0.21 mmol, 0.06 g; prepared as described in DE 19735410).
ESI-MS: [M+Na$^+$]=501.2, 480.2, [M+H$^+$]=479.2, 240.1.

Example 95

4-(2-tert-Butyl-6-trifluoromethylpyrimidin-4-yl)-1-[4-(4-ethyl-2-oxo-2H-pyrimidin-1-yl)butyl]piperazin-1-ium fumarate

95.1 1,1-Dimethoxypentan-3-one 6.60 g of 1,1-dimethoxypentan-3-one were obtained in analogy to Helv. Chim. Acta 2002, 85, 2926-29 (Example 6, p. 2928) by reacting ethyl methyl ketone (161.98 mmol, 11.68 g) with methyl formate (324.66 mmol, 19.50 g).

95.2 4-Ethyl-1H-pyrimidin-2-one 2.90 g of 4-ethyl-1H-pyrimidin-2-one were obtained in analogy to Example 8.1 by reacting 1,1-dimethoxy-pentan-3-one from Example 95.1 (29.55 mmol, 4.80 g) with urea.
ESI-MS: [M+H$^+$]=125.1.

95.3 1-(4-Chlorobutyl)-4-ethyl-1H-pyrimidin-2-one 0.22 g of 1-(4-chlorobutyl)-4-ethyl-1H-pyrimidin-2-one was obtained in analogy to Example 5.2.1 by reacting 4-ethyl-1H-pyrimidin-2-one from Example 95.2 (23.36 mmol, 2.90 g) with 1-bromo-4-chlorobutane.
ESI-MS: [M+H$^+$]=215.1.

95.4 4-(2-tert-Butyl-6-trifluoromethylpyrimidin-4-yl)-1-[4-(4-ethyl-2-oxo-2H-pyrimidin-1-yl)butyl]piperazin-1-ium fumarate 0.09 g of the title compound was obtained in analogy to Example 5.2.2 by reacting 1-(4-chlorobutyl)-4-ethyl-1H-pyrimidin-2-one from Example 95.3 (0.47 mmol, 0.10 g) with 2-tert-butyl-4-piperazin-1-yl-6-trifluoromethylpyrimidine (0.47 mmol, 0.14 g; prepared as described in DE 19735410).
ESI-MS: [M+H$^+$]=467.3, 234.1.

Example 96

4-(2-tert-Butyl-6-propylpyrimidin-4-yl)-1-[4-(4-ethyl-2-oxo-2H-pyrimidin-1-yl)butyl]piperazin-1-ium fumarate 12.0 mg of the title compound were obtained in analogy to Example 5.2.2 by reacting 1-(4-chlorobutyl)-4-ethyl-1H-pyrimidin-2-one from Example 95.3 (0.33 mmol, 0.07 g) with 2-tert-butyl-4-piperazin-1-yl-6-propylpyrimidine (0.34 mmol, 0.09 g; prepared as described in DE 19735410).
ESI-MS: [M+H$^+$]=441.4, 221.1.

Example 97

4-(2-tert-Butyl-6-trifluoromethylpyrimidin-4-yl)-1-[4-(4-isopropyl-2-oxo-2H-pyrimidin-1-yl)butyl]piperazin-1-ium fumarate

97.1 1,1-Dimethoxy-4-methylpentan-3-one 7.80 g of the title compound were obtained in analogy to Helv. Chim. Acta 2002, 85, 2926-29 (Example 6, p. 2928) by reacting 3-methylbutan-2-one (186.68 mmol, 16.08 g) with methyl formate (373.04 mmol, 22.40 g).

97.2 4-Isopropyl-1H-pyrimidin-2-one 3.30 g of 4-isopropyl-1H-pyrimidin-2-one were obtained in analogy to Example 8.1 from 1,1-dimethoxy-4-methylpentan-3-one from Example 97.1 (43.69 mmol, 7.00 g) with urea.
ESI-MS: [M+H$^+$]=139.1.

97.3 1-(4-Chlorobutyl)-4-isopropyl-1H-pyrimidin-2-one 0.90 g of 1-(4-chlorobutyl)-4-isopropyl-1H-pyrimidin-2-one was obtained in analogy to Example 5.2.1 by reacting 4-isopropyl-1H-pyrimidin-2-one from Example 97.2 (14.47 mmol, 2.00 g) with 1-bromo-4-chlorobutane.
ESI-MS: 231.1, [M+H$^+$]=229.1.

97.4 4-(2-tert-Butyl-6-trifluoromethylpyrimidin-4-yl)-1-[4-(4-isopropyl-2-oxo-2H-pyrimidin-1-yl)butyl]piperazin-1-ium fumarate 0.27 g of the title compound was obtained in analogy to Example 5.2.2 by reacting 1-(4-chlorobutyl)-4-isopropyl-1H-pyrimidin-2-one from Example 97.3 (1.09 mmol, 0.25 g) with 2-tert-butyl-4-piperazin-1-yl-6-trifluoromethylpyrimidine (1.09 mmol, 0.32 g; prepared as described in DE 19735410).
ESI-MS: [M+H$^+$]=481.2, 241.1.

Example 98

4-(2-tert-Butyl-6-propylpyrimidin-4-yl)-1-[4-(4-isopropyl-2-oxo-2H-pyrimidin-1-yl)butyl]piperazine 1-fumarate 0.35 g of the title compound was obtained in analogy to Example 5.2.2 by reacting 1-(4-chlorobutyl)-4-isopropyl-1H-pyrimidin-2-one from Example 97.3 (1.09 mmol, 0.25 g) with 2-tert-butyl-4-piperazin-1-yl-6-propylpyrimidine (1.11 mmol, 0.29 g; prepared as described in DE 19735410).
ESI-MS: [M+H$^+$]=455.4, 228.1.

Example 99

4-(2-tert-Butyl-6-trifluoromethylpyrimidin-4-yl)-1-[4-(4-cyclohexyl-2-oxo-2H-pyrimidin-1-yl)butyl]piperazin-1-ium fumarate 99.1 1-Cyclohexyl-3,3-dimethoxypropan-1-one 1.50 g of the title compound were obtained in analogy to Helv. Chim. Acta 2002, 85, 2926-29 (Example 6, p. 2928) by reacting 1-cyclohexylethanone (150.55 mmol, 19.00 g) with methyl formate (300.05 mmol, 18.02 g).

99.2 4-Cyclohexyl-1H-pyrimidin-2-one 0.62 g of the title compound was obtained in analogy to Example 8.1 by reacting 1-cyclohexyl-3,3-dimethoxypropan-1-one from Example 99.1 (6.99 mmol, 1.40 g) with urea.
ESI-MS: [M+H$^+$]=179.1.

99.3 1-(4-Chlorobutyl)-4-cyclohexyl-1H-pyrimidin-2-one 0.65 g of 1-(4-chlorobutyl)-4-cyclohexyl-1H-pyrimidin-2-one was obtained in analogy to Example 5.2.1 by reacting 4-cyclohexyl-1H-pyrimidin-2-one from Example 99.2 (2.55 mmol, 0.46 g) with 1-bromo-4-chlorobutane.
ESI-MS: 271.1, [M+H$^+$]=269.1.

99.4 4-(2-tert-Butyl-6-trifluoromethylpyrimidin-4-yl)-1-[4-(4-cyclohexyl-2-oxo-2H-pyrimidin-1-yl)butyl]piperazin-1-ium fumarate 0.40 g of the title compound was obtained in analogy to Example 5.2.2 by reacting 1-(4-chlorobutyl)-4-cyclohexyl-1H-pyrimidin-2-one from Example 99.3 (1.12 mmol, 0.30 g) with 2-tert-butyl-4-piperazin-1-yl-6-trifluoromethylpyrimidine (1.14 mmol, 0.33 g; prepared as described in DE 19735410).
ESI-MS: [M+H$^+$]=521.3, 261.1.

Example 100

4-(2-tert-Butyl-6-propylpyrimidin-4-yl)-1-[4-(4-cyclohexyl-2-oxo-2H-pyrimidin-1-yl)butyl]piperazin-1-ium fumarate 0.23 g of the title compound was obtained in analogy to Example 5.2.2 by reacting 1-(4-chlorobutyl)-4-cyclohexyl-1H-pyrimidin-2-one from Example 99.3 (0.82 mmol, 0.22 g) with 2-tert-butyl-4-piperazin-1-yl-6-propylpyrimidine (0.82 mmol, 0.22 g; prepared as described in DE 19735410).
ESI-MS: [M+H$^+$]=495.4, 248.3.

Example 101

1-{4-[4-(2-tert-Butyl-6-trifluoromethylpyrimidin-4-yl)piperazin-1-yl]butyl}-5-phenyl-1H-pyrimidin-2-one 101.1 5-Phenyl-1H-pyrimidin-2-one 40.0 mg of 5-phenyl-1H-pyrimidin-2-one were obtained in analogy to the method in Tetrahedron 1997, 53, 14437-50 from 5-bromo-1H-pyrimidin-2-one (2.29 mmol, 0.40 g).
ESI-MS: [M+H$^+$]=173.1.

101.2 1-(4-Chlorobutyl)-5-phenyl-1H-pyrimidin-2-one 0.03 g of 1-(4-chlorobutyl)-5-phenyl-1H-pyrimidin-2-one was obtained in analogy to Example 5.2.1 by reacting 5-phenyl-1H-pyrimidin-2-one from Example 101.1 (0.23 mmol, 0.04 g) with 1-bromo-4-chlorobutane.
ESI-MS: [M+H$^+$]=263.1.

101.3 1-{4-[4-(2-tert-Butyl-6-trifluoromethylpyrimidin-4-yl)piperazin-1-yl]butyl}-5-phenyl-1H-pyrimidin-2-one 8.0 mg of the title compound were obtained in analogy to Example 5.2.2 by reacting 1-(4-chlorobutyl)-5-phenyl-1H-pyrimidin-2-one from Example 101.3 (0.10 mmol, 0.03 g) with 2-tert-butyl-4-piperazin-1-yl-6-trifluoromethylpyrimidine (0.09 mmol, 0.03 g; prepared as described in DE 19735410).
ESI-MS: [M+H$^+$]=515.3, 258.2.

Example 102

1-{4-[4-(3,4-Dimethoxyphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,4-dimethoxyphenyl)-piperazine.
ESI-MS: [M+H$^+$]=403.2.

Example 103

1-{4-[4-(2-Fluorophenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(2-fluorophenyl)piperazine.
ESI-MS: [M+H$^+$]=361.1.

Example 104

1-{4-[4-(4-Fluorophenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(4-fluorophenyl)piperazine.
ESI-MS: [M+H$^+$]=361.0.

Example 105

1-{4-[4-(2-Methoxyphenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(2-methoxyphenyl)piperazine.
ESI-MS: [M+H$^+$]=373.0.

Example 106

1-{4-[4-(4-Methoxyphenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(4-methoxyphenyl)piperazine.
ESI-MS: [M+H$^+$]=373.1.

Example 107

1-{4-[4-(2-Ethoxyphenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(2-ethoxyphenyl)piperazine.
ESI-MS: [M+H$^+$]=387.0, 234.9.

Example 108

2-{4-[4-(5-Methyl-2,4-dioxo-3,4-dihydro-2H-pyrimidin-1-yl)butyl]piperazin-1-yl}nicotinonitrile The title compound was obtained in analogy to Example 5.2.2 by reacting 1-(4-chlorobutyl)-4-hydroxy-5-methylpyrimidin-2(1H)-one with 2-piperazin-1-ylnicotinonitrile.
ESI-MS: [2M+H$^+$]=737.2, [M+H$^+$]=369.1.

Example 109

1-{4-[4-(2,4-Dimethoxyphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,4-dimethoxyphenyl)piperazine.
ESI-MS: [M+H$^+$]=403.2.

Example 110

1-{4-[4-(3,4-Difluorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,4-difluorophenyl)piperazine.
ESI-MS: [2M+H$^+$]=757.1, [M+H$^+$]=379.0.

Example 111

5-Methyl-1-[4-(4-(o-tolyl)piperazin-1-yl)butyl]-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(o-tolyl)piperazine.
ESI-MS: [M+H$^+$]=357.1.

Example 112

5-Methyl-1-{4-[4-(6-methylpyridin-2-yl)piperazin-1-yl]butyl}-1H-pyrimidine-2,4-dione The title compound was obtained in analogy to Example 5.2.2 by reacting 1-(4-chlorobutyl)-4-hydroxy-5-methylpyrimidin-2(1H)-one with 1-(6-methylpyridin-2-yl)piperazine.
ESI-MS: [2M+H$^+$]=715.2, [M+H$^+$]=358.0, 134.9.

Example 113

1-{4-[4-(2,5-Dimethoxyphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,5-dimethoxyphenyl)piperazine.
ESI-MS: [M+H$^+$]=417.2, 264.9, 151.2.

Example 114

5-Methyl-1-{4-[4-(3-methylpyridin-2-yl)piperazin-1-yl]butyl}-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3-methylpyridin-2-yl)piperazine.
ESI-MS: [M+H$^+$]=358.1.

Example 115

5-Methyl-1-{4-[4-(4-methylpyridin-2-yl)piperazin-1-yl]butyl}-1H-pyrimidine-2,4-dione The title compound was obtained in analogy to Example 5.2.2 by reacting 1-(4-chlorobutyl)-4-hydroxy-5-methylpyrimidin-2(1H)-one with 1-(4-methylpyridin-2-yl)piperazine.
ESI-MS: [M+H$^+$]=358.0, 134.9.

Example 116

4-{4-[4-(5-Methyl-2,4-dioxo-3,4-dihydro-2H-pyrimidin-1-yl)butyl]piperazin-1-yl}benzonitrile The title compound was obtained in analogy to Example 5.2.2 by reacting 1-(4-chlorobutyl)-4-hydroxy-5-methylpyrimidin-2(1H)-one with 4-piperazin-1-ylbenzonitrile.
ESI-MS: [2M+H$^+$]=735.1, [M+H$^+$]=368.1.

Example 117

1-{4-[4-(5-Chloro-2-methoxyphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(5-chloro-2-methoxyphenyl)piperazine.
ESI-MS: [M+H$^+$]=407.0, 226.8.

Example 118

1-{4-[4-(4-tert-Butylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(4-tert-butylphenyl)piperazine.
ESI-MS: [M+H$^+$]=399.3, 218.9.

Example 119

1-{4-[4-(3,5-Dichlorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,5-dichlorophenyl)piperazine.
ESI-MS: [M+H$^+$]=411.2, 230.8.

Example 120

2-{4-[4-(5-Methyl-2,4-dioxo-3,4-dihydro-2H-pyrimidin-1-yl)butyl]piperazin-1-yl}benzonitrile The title compound was obtained in analogy to Example 5.2.2 by reacting 1-(4-chlorobutyl)-4-hydroxy-5-methylpyrimidin-2(1H)-one with 2-(piperazin-1-yl)benzonitrile.
ESI-MS: [M+H$^+$]=368.1, 187.9.

Example 121

1-{4-[4-(4-Chloro-3-trifluoromethylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(4-chloro-3-trifluoromethylphenyl)piperazine.
ESI-MS: [M+H$^+$]=445.0, 403.0, 292.8, 264.8.

Example 122

1-{4-[4-(2,6-Dimethylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,6-dimethylphenyl)piperazine.
ESI-MS: [M+H$^+$]=371.0, 190.9, 147.9.

Example 123

1-{4-[4-(2,4-Dichlorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,4-dichlorophenyl)piperazine.
ESI-MS: [M+H$^+$]=411.0, 230.8, 187.7.

Example 124

5-Methyl-1-{4-[4-(3-trifluoromethylpyridin-2-yl)piperazin-1-yl]butyl}-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3-trifluoromethylpyridin-2-yl)piperazine.
ESI-MS: [M+H$^+$]=412.2, 259.9, 231.8, 188.8.

Example 125

1-{4-[4-(3,5-Bis-trifluoromethylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,5-bis-trifluoromethylphenyl)piperazine.
ESI-MS: [M+H$^+$]=479.0, 340.2, 298.8.

Example 126

5-Methyl-1-[4-(4-(p-tolyl)piperazin-1-yl)butyl]-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(p-tolyl)piperazine (1-(4-methylphenyl)piperazine).
ESI-MS: [M+H$^+$]=357.0, 204.9, 176.9.

Example 127

1-{4-[4-(2-Chlorophenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(2-chlorophenyl)piperazine.
ESI-MS: [M+H$^+$]=376.9, 196.8.

Example 128

1-{4-[4-(2,3-Dimethylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,3-dimethylphenyl)piperazine.
ESI-MS: [M+H$^+$]=371.0, 190.9.

Example 129

5-Methyl-1-{4-[4-(3-trifluoromethylphenyl)piperazin-1-yl]butyl}-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3-trifluoromethylphenyl)piperazine.
ESI-MS: [M+H$^+$]=411.1, 271.9, 230.8.

Example 130

1-{4-[4-(4-Chlorophenyl)piperazin-1-yl]butyl}-5-methyl-1H-pyrimidine-2,4-dione

The title compound was obtained in analogy to Example 5.2.2 by reacting 1-(4-chlorobutyl)-4-hydroxy-5-methylpyrimidin-2(1H)-one with 1-(4-chlorophenyl)piperazine.
ESI-MS: [M+H$^+$]=376.9, 196.8, 153.8.

Example 131

1-{4-[4-(2,4-Difluorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,4-difluorophenyl)piperazine.
ESI-MS: [M+H$^+$]=379.0, 198.9.

Example 132

1-{4-[4-(3,5-Dimethylphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,5-dimethylphenyl)piperazine.
ESI-MS: [2M+H$^+$]=741.2, [M+H$^+$]=371.0, 190.9, 147.9.

Example 133

1-{4-[4-(4-Chloro-2-fluorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(4-chloro-2-fluorophenyl)piperazine.
ESI-MS: [M+H$^+$]=395.0, 214.8.

Example 134

1-{4-[4-(3,5-Dimethoxyphenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(3,5-dimethoxyphenyl)piperazine.
ESI-MS: [M+H$^+$]=403.2, 222.9.

Example 135

1-{4-[4-(2,3-Dichlorophenyl)piperazin-1-yl]butyl}-5-methyl-1H-pyrimidine-2,4-dione The title compound was obtained in analogy to Example 5.2.2 by reacting 1-(4-chlorobutyl)-4-hydroxy-5-methylpyrimidin-2(1H)-one with 1-(2,3-dichlorophenyl)piperazine.
ESI-MS: [M+H$^+$]=410.9, 230.8.

Examples of pharmaceutical administration forms

| A) Tablets |
| --- |
| Tablets of the following composition are compressed in a tablet press in a conventional way: |

| | |
| --- | --- |
| 40 mg | of substance of example 2 |
| 120 mg | of corn starch |
| 13.5 mg | of gelatin |
| 45 mg | of lactose |
| 2.25 mg | of Aerosil ® (chemically pure silica in submicroscopically fine distribution) |
| 6.75 mg | of potato starch (as 6% strength paste) |

| B) Sugar-coated tablets |  |
| --- | --- |
| 20 mg | of substance of example 2 |
| 60 mg | of core composition |
| 70 mg | of sugar-coating composition |

The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

Biological Investigations—Receptor Binding Studies:
The substance to be tested was dissolved either in methanol/Chremophor® (BASF-AG) or in dimethyl sulfoxide and then diluted with water to the desired concentration.

Dopamine D$_3$ Receptor:
The mixture (0.250 ml) is composed of membranes from ~10$^6$ HEK-293 cells with stably expressed human dopamine D3 receptors, 0.1 nM [$^{125}$I]-iodosulpride and incubation buffer (total binding) or with additional test substance (inhibition plot) or 1 µM spiperone (nonspecific binding). Triplicate mixtures were carried out.

The incubation buffer contained 50 mM Tris, 120 mM NaCl, 5 mM KCl, 2 mM CaCl$_2$, 2 mM MgCl$_2$ and 0.1% bovine serum albumin, 10 µM quinolone, 0.1% ascorbic acid (prepared fresh each day). The buffer was adjusted to pH 7.4 with HCl.

Dopamine D$_{2L}$ Receptor:
The mixture (1 ml) was composed of membranes from ~10$^6$ HEK-293 cells with stably expressed human dopamine D$_{2L}$ receptors (long isoform) and 0.01 nM [$^{125}$I]-iodospiperone and incubation buffer (total binding) or with additional test substance (inhibition plot) or 1 µM haloperidol (nonspecific binding). Triplicate mixtures were carried out.

The incubation buffer contained 50 mM Tris, 120 mM NaCl, 5 mM KCl, 2 mM CaCl$_2$, 2 mM MgCl$_2$ and 0.1% bovine serum albumin. The buffer was adjusted to pH 7.4 with HCl.

Measurement and Evaluation:
After incubation at 25° C. for 60 minutes, the mixtures were filtered under vacuum through Whatman GF/B glass fiber filters using a cell harvester. The filters were transferred by a filter transfer system into scintillation vials. After addition of 4 ml of Ultima Gold® (Packard), the samples were shaken for one hour and then the radioactivity was calculated in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the Statistical Analysis System (SAS) similar to the "LIGAND" program described by Munson and Rodbard.

In these assays, the inventive compounds show very good affinities for the $D_3$ receptor (<100 nM, frequently <50 nM) and bind selectively to the $D_3$ receptor. The results of the binding assays are indicated in table 2.

TABLE 2

| Example | $K_i$ ($D_3$) [nM] | Selectivity $D_3$ vs. $D_2L$* |
|---|---|---|
| 2 | 3.23 | 88 |
| 5 | 1.30 | 246 |
| 6 | 31.2 | 35 |
| 8 | 4.4 | 71 |
| 9 | 0.74 | 53 |
| 10 | 1.75 | 97 |
| 11 | 3.14 | 65 |
| 12 | 3.44 | 63 |
| 13 | 1.88 | 104 |
| 14 | 2.62 | 82 |
| 15 | 14.5 | 64 |
| 16 | 2.99 | 201 |
| 17 | 0.71 | 134 |
| 18 | 4.78 | 99 |
| 19 | 1.44 | 96 |
| 20 | 1.87 | 108 |
| 21 | 1.94 | 96 |
| 22 | 1.16 | 77 |
| 23 | 1.51 | 63 |
| 24 | 1.38 | 122 |
| 25 | 10.40 | 34 |
| 26 | 8.10 | 55 |
| 27 | 11.8 | 52 |
| 29 | 7.64 | 67 |
| 33 | 0.70 | 42 |
| 35 | 4.96 | 116 |
| 36 | 3.82 | 209 |
| 37 | 3.24 | 126 |
| 38 | 5.33 | 103 |
| 39 | 6.09 | 66 |
| 40 | 2.12 | 67 |
| 41 | 5.78 | 62 |
| 44 | 0.63 | 158 |
| 45 | 4.99 | 37 |
| 46 | 5.41 | 43 |
| 47 | 4.87 | 51 |
| 49 | 0.54 | 86 |
| 50 | 0.72 | 77 |
| 52 | 2.28 | 97 |
| 53 | 2.32 | 56 |
| 54 | 9.25 | 52 |
| 55 | 5.44 | 119 |
| 56 | 1.02 | 134 |
| 57 | 0.96 | 111 |
| 59 | 1.80 | 44 |
| 60 | 4.33 | 91 |
| 61 | 5.84 | 28 |
| 62 | 11.0 | 49 |
| 63 | 2.97 | 65 |
| 64 | 2.57 | 57 |
| 65 | 3.31 | 62 |
| 66 | 13.5 | 37 |
| 67 | 10.1 | 39 |
| 69 | 1.80 | 54 |
| 70 | 10.0 | 30 |
| 71 | 7.44 | 37 |
| 72 | 1.49 | 54 |
| 73 | 9.30 | 31 |
| 74 | 1.52 | 53 |
| 75 | 2.30 | 80 |
| 76 | 3.03 | 103 |
| 77 | 0.74 | 150 |
| 78 | 0.32 | 48 |
| 79 | 0.86 | 30 |
| 81 | 2.56 | 94 |
| 82 | 0.31 | 54 |
| 83 | 1.66 | 89 |
| 84 | 0.75 | 63 |
| 85 | 7.36 | 35 |
| 86 | 2.44 | 43 |
| 87 | 0.97 | 31 |
| 92 | 4.56 | 31 |
| 93 | 0.65 | 40 |
| 94 | 4.28 | 36 |
| 95 | 6.53 | 45 |
| 97 | 4.26 | 58 |
| 98 | 1.62 | 59 |
| 99 | 4.82 | 57 |
| 100 | 1.38 | 51 |
| 111 | 6.80 | 30 |
| 119 | 0.46 | 65 |
| 125 | 6.8 | 63 |
| 127 | 1.5 | 45 |
| 128 | 2.4 | 55 |
| 129 | 1.3 | 48 |
| 131 | 25.7 | 30 |
| 132 | 5.5 | 34 |
| 134 | 13.1 | 55 |
| 135 | 0.27 | 87 |

*$K_i(D_3)/K_i(D_{2L})$

Inhibition of Mitochondrial Respiration:

The inhibition of mitochondrial respiration by the compounds of the invention was ascertained by determining the oxygen consumption of mitochondria associated with the production of ATP in a manner known per se (see Donelly et al. Arch. Toxicol. 1994. 68. p. 110. Wong et al. Toxicol. Lett. 2000. 116(3). p. 171-81. Devi et al. Life Sci. 1997. 60(11). p. 849-55).

The investigation was carried out using a Strathkelvin measuring instrument to determine dissolved $O_2$, using the recording and analysis software belonging thereto.

For this purpose, initially the $O_2$ electrodes of the measuring instrument were equilibrated in Hudson's buffer (140 mM KCl/5 mM $KH_2PO_4$/20 mM MOPS/pH=7.2) and then with aqueous sodium sulfite solution (20 g/l). The electrodes were rinsed with water (double-distilled) after equilibration before each measurement.

In a reaction vessel with 6 separate chambers, each equipped with magnetic stirring bars and thermostated at 37° C., 1.4 ml of Hudson's buffer and then 7.5 µl of a solution of the active substance in dimethyl sulfoxide (normally in a concentration range from 0.8 to 40 mM) were put into chambers 2 to 6 of the investigation vessel, and 7.5 µl of DMSO without active substance were put into chamber 1. A suspension of freshly isolated functional mitochondria was put into each chamber in an amount of 1.5 mg of total protein (per chamber). The electrode was then inserted into the respective chamber, the electrodes were allowed to equilibrate for 30-60 s, and then 25 µL of succinic acid solution (300 mM) were added and equilibrated for 60-120 s. 2 µL of adenosine diphosphate solution (200 mM) were added thereto and equilibrated for some minutes, and then 1 µL of 2,4-dinitrophenol solution (300 mM) was added and at least one further minute was allowed to elapse. The oxygen concentration was then recorded. The concentration necessary to inhibit oxygen uptake ($IC_{50}$ value) was ascertained therefrom.

The compounds of the invention inhibit mitochondrial respiration only at a high concentration ordinarily above 50 µM, in particular >100 µM ($IC_{50}$ values) and specifically >200 µM.

Investigation of the Nonselective Protein Binding 2 concentrations of the substance to be tested in plasma are investigated. 100 µl of a stock solution (1 mg/ml) are spiked in 4.9 ml of plasma for the 20 000 ng/ml concentration, and 25 µl of the stock solution in 4.975 ml of plasma for the 5000 ng/ml concentration. In each case, 1 ml portions of the spiked plasma of each concentration are weighed into ultracentrifugation tubes for a triplicate determination, and centrifuged at 80 000×g and 15° C. for 18 h. 5 samples each of 100 µl of the respective supernatant is taken directly from the surface of each tube, pipetted into Eppendorf tubes, mixed with 100 µl of acetonitrile/water mixture (1:1) and frozen at −20° C. until analyzed. The remaining 500 µl of plasma with the pellet are taken up in 500 µl of acetonitrile/water mixture (1:1) and frozen until analyzed.

Analysis takes place by LC/MS/MS. For the evaluation, the concentrations of the first 2×100 µl of the plasma supernatant are related to the total concentration recovered.

The compounds of the invention are distinguished by a comparatively low protein binding. They therefore show a higher free concentration in the plasma and ought to show better tolerability because of a more uniform plasma level (less release from plasma protein binding, e.g. through physical activity or medicament interaction).

The invention claimed is:

1. A pyrimidin-2-one compound of the formula I, or a tautomer thereof,

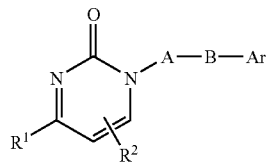

in which
A is —$(CH_2)_n$—, in which n is 4, 5, or 6, or is trans-$CH_2$—CH=CH—$CH_2$—, trans-$CH_2$—C($CH_3$)=CH—$CH_2$—, —$CH_2$—CH($CH_3$)—$CH_2$—$CH_2$—, or —$CH_2$—$CH_2$—$CH_2$—CH($CH_3$)—,
B is a radical of the formula:

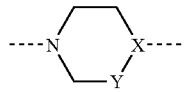

in which X is $CH_2$ or N, and Y is $CH_2$ or $CH_2CH_2$, or X—Y together may also be C=CH, C=CH—$CH_2$ or CH—CH=CH,
$R^1$ is selected from $OR^{3a}$, $NR^4R^5$, $SR^6$, $C_3$-$C_6$-cycloalkyl, $C_1$-$C_4$-alkyl which is optionally substituted by OH, $C_1$-$C_4$-alkoxy, halogen or phenyl,
5- or 6-membered aromatic heterocyclyl having 1, 2 or 3 heteroatoms selected from O, S and N, which may be substituted by one or two radicals which are selected independently of one another from $C_1$-$C_4$-alkyl, $C_1$-$C_4$-alkoxy, $NR^4R^5$, CN, OH, $C_1$-$C_2$-fluoroalkyl or halogen, and
phenyl which may be substituted by one or two radicals which are selected independently of one another from $C_1$-$C_4$-alkyl, $C_1$-$C_4$-alkoxy, $NR^4R^5$, OH, CN, $C_1$-$C_2$-fluoroalkyl or halogen
$R^2$ is selected from H, $C_1$-$C_4$-alkyl, halogen, $C_1$-$C_2$-fluoroalkyl and cyano,
Ar is an aromatic radical which is selected from phenyl, pyridyl, pyrimidinyl and triazinyl, where the aromatic radical may have 1, 2 or 3 substituents which are selected independently of one another from $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_3$-$C_6$-cycloalkyl, $C_5$-$C_{10}$-bicycloalkyl, $C_6$-$C_{10}$-tricycloalkyl, where the last three groups mentioned may optionally be substituted by halogen or $C_1$-$C_4$-alkyl, or halogen, CN, $OR^{3c}$, $NR^4R^5$, $NO_2$, $SR^6$, $SO_2R^6$, $SO_2NR^4R^5$, $COOR^7$, $COR^8$, 5- or 6-membered heterocyclyl having 1, 2 or 3 heteroatoms selected from O, S and N, and phenyl, where phenyl and heterocyclyl optionally have one or two substituents which are selected independently of one another from $C_1$-$C_4$-alkyl, $C_1$-$C_4$-alkoxy, $NR^4R^5$, CN, $C_1$-$C_2$-fluoroalkyl and halogen, and where 2 substituents bonded to adjacent C atoms of the aromatic radical may together be $C_3$- or $C_4$-alkylene, or may together with the C atoms to which they are bonded be a fused-on, unsaturated 5 or 6-membered carbocycle or a 5- or 6-membered heterocycle having 1 or 2 nitrogen atoms as ring members,
$R^3$, $R^{3a}$, $R^{3b}$, $R^{3c}$, $R^{3d}$, $R^4$, $R^5$, $R^6$, $R^7$ and $R^8$ are independently of one another H, $C_1$-$C_6$-alkyl which is optionally substituted by OH, $C_1$-$C_4$-alkoxy or phenyl, or $C_1$-$C_6$-haloalkyl or phenyl, where $R^5$ may also be a group $COR^9$ where $R^9$ is hydrogen, $C_1$-$C_4$-alkyl or phenyl which is optionally substituted by one or two radicals which are selected independently of one another from $C_1$-$C_4$-alkyl, $C_1$-$C_4$-alkoxy, $NR^4R^5$, CN, $C_1$-$C_2$-fluoroalkyl or halogen, where
$R^4$ with $R^5$ may also form together with the nitrogen atom to which they are bonded a 4-, 5- or 6-membered saturated or unsaturated heterocycle which may optionally have a further heteroatom selected from O, S and $NR^{10}$ as ring member, where $R^{10}$ is hydrogen or $C_1$-$C_4$-alkyl, and where the heterocycle may optionally carry 1, 2, 3 or 4 $C_1$-$C_4$-alkyl groups,
or a physiologically tolerated salt thereof.

2. A pyrimidinone compound as claimed in claim 1, in which Ar is selected from a radical of the general formula:

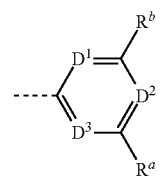

in which at least one of the variables $D^1$ to $D^3$ is N and the other variables $D^1$ to $D^3$ are CH, and $R^a$ and $R^b$ have independently of one another the following meanings: $OR^{3c}$, $NR^4R^5$, CN, $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_3$-$C_6$-cycloalkyl, $C_5$-$C_{10}$-bicycloalkyl, $C_6$-$C_{10}$-tricycloalkyl, where the last three groups mentioned may optionally be substituted by halogen or $C_1$-$C_4$-alkyl, or halogen, CN, $C_1$-$C_4$-alkoxy, 5- or 6-membered heterocyclyl having 1, 2 or 3 heteroatoms selected from O, S and N, and phenyl, where phenyl and heterocyclyl optionally have one or two substituents which are selected independently of one another from $C_1$-$C_4$-alkyl, $C_1$-$C_4$-alkoxy, $NR^4R^5$, CN, $C_1$-$C_2$-fluoroalkyl and halogen.

3. A pyrimidinone compound as claimed in claim 2, in which $R^a$ is $C_1$-$C_6$-alkyl and $R^b$ is selected from $C_1$-$C_6$-alkyl, $C_3$-$C_6$-cycloalkyl and $C_1$-$C_2$-fluoroalkyl.

4. A pyrimidinone compound as claimed in claim 1, in which $R^1$ is $OR^{3a}$ in particular OH.

5. A pyrimidinone compound as claimed in claim 1, in which $R^2$ is selected from H, $C_1$-$C_4$-alkyl, halogen or cyano.

6. A pyrimidinone compound as claimed in claim 1, in which A is a group of the formula —$(CH_2)_n$— in which n is 4.

7. A pyrimidinone compound as claimed in claim 1, in which B in formula I is selected from bivalent radicals of the general formulae:

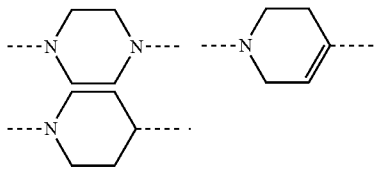

8. A pyrimidinone compound of the formula I.1, or a tautomer thereof,

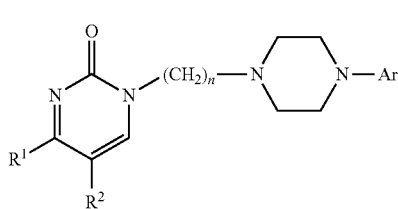

in which Ar, $R^1$ and $R^2$ have the meanings stated in claim 1, n is 4, 5 or 6,
or a physiologically tolerated acid addition salt thereof.

9. A pyrimidinone compound as claimed in claim 8, in which Ar is selected from a radical of the general formula:

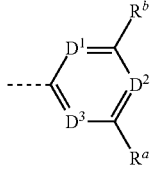

in which at least one of the variables $D^1$ to $D^3$ is N and the other variables $D^1$ to $D^3$ are CH, $R^b$ is $C_1$-$C_6$-alkyl, and $R^a$ is selected from $C_1$-$C_6$-alkyl, $C_3$-$C_6$-cycloalkyl and $C_1$-$C_2$-fluoroalkyl.

10. A pyrimidinone compound as claimed in claim 9, in which $D^1$ and $D^2$ are N and $D^3$ is CH.

11. A pyrimidinone compound as claimed in claim 8, in which $R^1$ is selected from $C_1$-$C_4$-alkyl, $C_3$-$C_6$-cycloalkyl, $OR^{3a}$, in which $R^{3a}$ has the aforementioned meanings, and phenyl which may be substituted by one or two radicals which are selected independently of one another from $C_1$-$C_4$-alkyl, $C_1$-$C_4$-alkoxy, OH, CN, $C_1$-$C_2$-fluoroalkyl or halogen.

12. A pyrimidinone compound as claimed in claim 11, in which $R^1$ is $OR^{3a}$ and in particular OH.

13. A pyrimidinone compound as claimed in claim 11, in which $R^1$ is $C_1$-$C_4$-alkyl and in particular methyl.

14. A pharmaceutical composition comprising at least one compound as claimed in claim 1 and/or the acid addition salt thereof, where appropriate together with physiologically acceptable carriers and/or excipients.

15. A method of treating Parkinson's disease, anxiety states, or addiction in a patient in need thereof comprising administering an effective amount of at least one compound of claim 1.

16. A method of treating schizophrenia and/or depression in a patient in need thereof comprising administering an effective amount of at least one compound of claim 1.

17. A compound of claim 1 having the general formula I.1a,

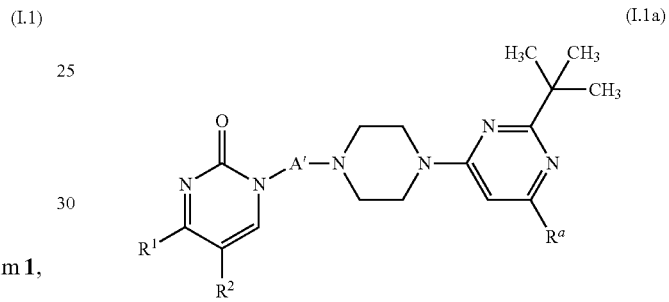

wherein
$R^1$ is OH, $R^2$ is H, $R^a$ is $CHF_2$ and A' is $(CH_2)_4$, or
$R^1$ is OH, $R^2$ is H, $R^a$ is $CF_3$ and A' is $(CH_2)_4$, or
$R^1$ is OH, $R^2$ is $CH_3$, $R^a$ is $CF_3$ and A' is $(CH_2)_4$, or
$R^1$ is OH, $R^2$ is F, $R^a$ is $CF_3$ and A' is $(CH_2)_4$ or
$R^1$ is OH, $R^2$ is H, $R^a$ is $CH_2CH_2CH_3$ and A' is $(CH_2)_4$ or
$R^1$ is OH, $R^2$ is $CH_3$, $R^a$ is $CH_2CH_2CH_3$ and A' is $(CH_2)_4$.

18. A pharmaceutical composition comprising at least one compound as claimed in claim 17 and/or the acid addition salt thereof, where appropriate together with physiologically acceptable carriers and/or excipients.

19. A method of treating Parkinson's disease, anxiety states, or addiction in a patient in need thereof comprising administering an effective amount of at least one compound of claim 17.

20. A method of treating schizophrenia and/or depression in a patient in need thereof comprising administering an effective amount of at least one compound of claim 17.

* * * * *